United States Patent
Lattuada et al.

(10) Patent No.: US 10,781,188 B2
(45) Date of Patent: Sep. 22, 2020

(54) CONTRAST AGENTS

(71) Applicant: BRACCO IMAGING S.P.A., Milan (IT)

(72) Inventors: Luciano Lattuada, Cassina de'Pecchi (IT); Roberta Napolitano, Albiano d'Ivrea (IT); Valeria Boi, Strambino (IT); Massimo Visigalli, Settala (IT); Silvio Aime, Carignano (IT); Giovanni Battista Giovenzana, Novara (IT); Alberto Fringuello Mingo, Envie (IT)

(73) Assignee: BRACCO IMAGING S.P.A., Milan (IT)

( * ) Notice: Subject to any disclaimer, the term of this patent is extended or adjusted under 35 U.S.C. 154(b) by 96 days.

(21) Appl. No.: 16/060,577

(22) PCT Filed: Dec. 12, 2016

(86) PCT No.: PCT/EP2016/080592
§ 371 (c)(1),
(2) Date: Jun. 8, 2018

(87) PCT Pub. No.: WO2017/098038
PCT Pub. Date: Jun. 15, 2017

(65) Prior Publication Data
US 2018/0362476 A1   Dec. 20, 2018

(30) Foreign Application Priority Data

Dec. 10, 2015  (EP) .................................. 15199220
May 24, 2016  (EP) .................................. 16170953
Oct. 20, 2016  (EP) .................................. 16194814

(51) Int. Cl.
*C07D 257/02* (2006.01)
*A61K 49/10* (2006.01)
*C07D 401/06* (2006.01)

(52) U.S. Cl.
CPC .......... *C07D 257/02* (2013.01); *A61K 49/108* (2013.01); *C07D 401/06* (2013.01)

(58) Field of Classification Search
CPC ... C07D 257/02; C07D 401/06; A61K 49/108
See application file for complete search history.

(56) References Cited

U.S. PATENT DOCUMENTS

| 4,647,447 | A | 3/1987 | Gries et al. |
| 4,885,363 | A | 12/1989 | Tweedle et al. |
| 4,916,246 | A | 4/1990 | Felder et al. |
| 5,132,409 | A | 7/1992 | Felder et al. |
| 5,277,895 | A | 1/1994 | Platzek et al. |
| 5,876,698 | A | 3/1999 | Schmitt-Willich et al. |
| 5,980,864 | A | 11/1999 | Platzek et al. |
| 6,149,890 | A | 11/2000 | Uggeri et al. |
| 7,208,140 | B2 | 4/2007 | Schirmer et al. |
| 2011/0177002 | A1 | 7/2011 | Zitzmann-Kolbe et al. |
| 2013/0296539 | A1 | 11/2013 | Bhushan |
| 2014/0086846 | A1 | 3/2014 | Grimmond et al. |
| 2015/0065711 | A1 | 3/2015 | Davis |

FOREIGN PATENT DOCUMENTS

| CN | 102727911 B | 7/2013 | |
| DE | 19849465 A1 | 4/2000 | |
| DE | 10117242 C1 * | 5/2002 | ......... A61K 49/0002 |
| DE | 10117242 C1 | 5/2002 | |
| EP | 0230893 A2 | 8/1987 | |
| EP | 0512661 A1 | 11/1992 | |
| EP | 0872479 A1 | 10/1998 | |
| WO | 9848844 A2 | 11/1998 | |
| WO | WO-9848844 A2 * | 11/1998 | ............. A61K 49/06 |
| WO | 9856775 A1 | 12/1998 | |
| WO | 2008126034 A2 | 10/2008 | |

OTHER PUBLICATIONS

Bechara, G. et al . "Polyazamacrocycles based on a tetraaminoacetate moiety and a (poly)pyridine intracyclic unit: direct synthesis and application to the photosensitization of Eu(III) and Tb(III) ions in aqueous solutions," Tetrahedron 2010 66:8594-8604.

Bordunov et al. "Synthesis of New Pyridinoazacrown Ethers Containing Aromatic and Heteroaromatic Proton Ionizable Substituents" J. Org. Chem. 1995, 60, 6097-6102.

Caravan et al., "Gadolinium (III) Chelates as MRI Contrast Agents: Structure, Dynamics, and Applications," Chem. Rev. 1999, 99, 2293-2352.

Douglass, et al., "Intramolecular Hydrophosphination/Cyclization of Phosphinoalkenes and Phosphinoalkynes Catalyzed by Organolanthanides: Scope, Selectivity, and Mechanism" J. Am. Chem. Soc. 2001, 123, 10221-10238.

Formanovsky, et al., "One Stage Monosubstitution in Cyclen-Two Novel Examples" Synthetic Communications, 1996 26(8), 1595-1603.

Fulton, D. et al, "Efficient relaxivity enhancement in dendritic gadolinium complexes: effective motional coupling in medium molecular weight conjugates," Chem. Comm. 2005, 474-476.

Geant et al., "Highly Enantioselective Access to α-Dibenzylamino Ketones from Chiral Nonracemic α-Bromo α'-Sulfinyl Ketones by Dynamic Kinetic Resolution: Synthesis of (2R,1'S)-2-[1-(Dibenzylamino)alkyl]oxiranes" Eur. J. Org. Chem. 2011, 1300-1309.

Glogard, et al., "Novel radical-responsive MRI contrast agent based on paramagnetic liposomes" Magnetic Resonance in Chemistry 2003, vol. 41, 585-588.

Greene et al. (Eds.), Protective Groups in Organic Synthesis, John Wiley & Sons, Inc., Chapter 5, pp. 152-179 (1981).

(Continued)

*Primary Examiner* — Michael G. Hartley
*Assistant Examiner* — Leah H Schlientz
(74) *Attorney, Agent, or Firm* — Vivicar Law, PLLC

(57) ABSTRACT

The present invention relates to new class of functionalized macrocycles capable of chelating paramagnetic metal ions, their chelated complexes with metal ions and the use thereof as contrast agents, particularly suitable for Magnetic Resonance Imaging (MRI) analysis.

40 Claims, No Drawings

(56) References Cited

OTHER PUBLICATIONS

Greene et al. (Eds.), Protective Groups in Organic Synthesis, Third Edition, John Wiley & Sons, Inc., Chapter 7, pp. 494-653 (1999).
Hovland et al., "Gadolinium DO3A derivatives mimicking phospholipids; preparation and in vitro evaluation as pH responsive MRI contrast agents" J. Chem. Soc. Perkin Trans. 2, 2001; 929-933.
Maeda et al., "Intramolecular Cyclization of N,N-di(oligooxyethylene)amines: A New Synthesis of Monoaza Crown Ethers" Tetrahedron 1982, vol. 38, No. 22, 3359-3362.
Manning et al., "Expeditious synthesis of 'P'-protected macrocycles en route to lanthanide chelate metal complexes" Tetrahedron Letters 46, (2005) 4707-4710.
Moore, "Selective Trialkylation of Cyclen with tert-Butyl Bromoacetate [1,4,7,10-Tetraazacyclododecane-1,4,7-triacetic acid, Tri-tert-butyl Ester Hydrobromide]" Org. Synth. 2008, 85,10-14.
PCT Search Report and Written Opinion for PCT/EP2016/080592, dated Jan. 23, 2017.
PCT Search Report and Written Opinion for PCT/EP2016/080621, dated Feb. 7, 2017.
Pinsker et al., "A Highly Efficient Type I β-Turn Mimetic Simulating an Asx-Pro-Turn-Like Structure." Organic Letters 2011; vol. 13, No. 13: 3502-3505.
Placidi, et al., "Aryl-phosphonate lanthanide complexes and their fluorinated derivatives: investigation of their unusual relaxometric behavior and potential application as dual frequency 1H/19F MRI probes" Chem. Eur. J. 2013, 19, 11644-11660.
Tei, et al., "Thermodynamic stability, kinetic inertness, and relaxometric properties of monoamide derivatives of lanthanide(III) DOTA complexes" Dalton Transactions, 2015 vol. 44, 5467-5478.
Wyatt, et al., "An enantioselective synthesis of (R)-2-amino-1-hydroxyethylphosphonic acid by hydrolytic kinetic resolution of (±)-diethyl oxiranephosphonate" Tetrahedron Letters 40 (1999) 6481-6483.
Yuan et al., "Studies on Organophosphorus Compounds 91: A Novel Synthesis of 1-Hydrazinoalkylphosphonic Acids and Derivatives Thereof" 1996, 507-510.
PubMed Entry, 6-bromohexane-1,2,3,4,5-pentol (Dec. 12, 2007).

* cited by examiner

CONTRAST AGENTS

CROSS-REFERENCE TO RELATED APPLICATIONS

This application is the national stage application of corresponding international application number PCT/EP2016/080592, filed Dec. 12, 2016, which claims priority to and the benefit of European application no. 15199220.3, filed Dec. 10, 2015, European application no. 16170953.0, filed May 24, 2016, and European application no. 1619481 4.6, filed Oct. 20, 2016, all of which are hereby incorporated by reference in their entirety.

FIELD OF THE INVENTION

The present invention relates to the field of diagnostic imaging and to novel contrast agents possessing improved relaxivity. More in particular, it relates to functionalized macrocycles capable of chelating paramagnetic metal ions, their chelated complexes with metal ions and the use thereof as contrast agents in Magnetic Resonance Imaging (MRI).

STATE OF THE ART

Magnetic Resonance Imaging (MRI) is a renowned diagnostic imaging technique increasingly used in clinical diagnostics for growing number of indications.

The undisputed success of this technique is determined by the advantages it offers, including a superb temporal and spatial resolution, the outstanding capacity of differentiating soft tissues and its safety, due to its non-invasiveness and the absence of any ionizing radiation, in contrast to, for instance, X-ray, PET and SPECT.

In MRI imaging the contrast is basically due to differences existing in the longitudinal T1 and the transverse T2 relaxation times of the water protons in the different body organs and tissues, which allows the in-vivo acquisition of high-resolution, three-dimensional images of the distribution of water.

The intensity of the signal recorded in MRI imaging stems, essentially, from the local value of the longitudinal relaxation rate 1/T1, and the transverse rate, 1/T2 of water protons, and increases with increasing of the 1/T1 value (of the longitudinal relaxation rate of water protons) while decreases with the increase of 1/T2. In other words, the shorter is T1, the higher is the intensity of the recorded signal in MRI, the better is the diagnostic image.

The strong expansion of medical MRI has further benefited from the development of a class of compounds, the MRI contrast agents, that act by causing a dramatic variation of nearby water proton relaxation rates in the tissues/organs/fluids wherein they distribute, thus adding relevant physiological information to the impressive anatomical resolution commonly obtained in the uncontrasted MRI images.

Contrast agents for use in the MRI imaging technique typically include a paramagnetic metal ion which is complexed with a cyclic or acyclic chelating ligand, more typically a polyaminopolycarboxylic chelator. The most important class of MRI contrast agents is represented by the Gd(III) chelates which are currently used in about ⅓ of the clinical tests. Indeed, Gd(III) is highly paramagnetic with seven unpaired electron and a long electronic relaxation time, making it an excellent candidate as a relaxation agent. By contrast, the free metal ion $[Gd(H_2O)_8]^{3+}$ is extremely toxic for living organism even at low doses (10-20 micromol/Kg). Thus, in order for it to be considered as a potentially valuable MRI contrast agent, a Gd(III) complex shall display a high thermodynamic (and possibly kinetic) stability ensuring against the release of toxic metal ion.

Preferred MRI contrast agent should furthermore display optimal relaxivity. Relaxivity ($r_{1p}$, $r_{2p}$), expressed in $mM^{-1}s^{-1}$ and usually measured at 298K and 20 MHz (approx. 0.5 T), is the intrinsic property of a paramagnetic complex which characterizes its capability to increase the nuclear magnetic relaxation rate, longitudinal ($1/T_1$) and transverse ($1/T_2$) respectively, of vicinal water protons and, thus, its efficacy as MRI contrast enhancing agent. In general terms, the higher the relaxivity of an MRI contrast agent, the greater its contrast enhancing capability and the stronger the contrast provided in recorded MRI images.

A number of complexes of paramagnetic metal ions are known in the art (see for instance: Caravan P. et al. Chem. Rev. 1999, 99, 2293-2352 and U.S. Pat. Nos. 4,647,447, 4,885,363; 4,916,246; 5,132,409; 6,149,890; DE19849465 and U.S. Pat. No. 5,980,864).

DO3A derivatives mimicking phospholipids forming supramolecular structures are for instance disclosed in J. Chem. Soc. Perkin Trans. 2, 2001; 929-933.

Examples of commercially available MRI contrast agents include the complex compound of the $Gd^{3+}$ ion with the DTPA ligand, marketed as MAGNEVIST®; the $Gd^{3+}$ complex of the DTPA-BMA ligand, marketed ad OMNISCAN®; the $Gd^{3+}$ complex of BOPTA, known as gadobenate Dimeglumine and marketed as MultiHance™; the $Gd^{3+}$ complex of the DOTA ligand, marketed as DOTAREM®; the $Gd^{3+}$ complex of the hydroxylated tetraaza macrocyclic ligand known as HPDO3A, long time marketed as Pro-Hance® and that of the corresponding butyl-triol derivative, known as Gadobutrol and marketed ad Gadavist®. All the above contrast agents are Non-Specific Agents (NSA), designed for a general use.

While known compounds generally provide a quality of the imaging capable of meeting and satisfying the present needs of radiologists resulting in accurate and detailed diagnostic information, there is nevertheless still the need for new compounds with improved contrast imaging features, such as increased relaxivity.

In particular, compounds with improved relaxivity could reduce the required dose of the paramagnetic contrast agent and possibly shorten the acquisition time of the imaging process.

SUMMARY OF THE INVENTION

The present invention generally relates to novel macrocyclic chelating ligands useful for the preparation of paramagnetic complexes having particularly favorable characteristics, among others in terms of improved relaxivity.

In general terms, an aspect of the present invention relates to novel tetraaza macrocyclic ligands having a pendant arm bound to a nitrogen atom of the chelating cage comprising a hydroxyl residue and suitable substituent group(s). In particular, the choice of suitable substituents on the pendant arm provides chelated complexes having improved relaxivity.

The invention further relates to respective chelated complexes of said chelating ligands with a paramagnetic metal ion and, especially, with $Gd^{3+}$, or of a physiologically acceptable salt thereof.

A further aspect of the invention relates to the use of such chelated complexes as contrast agents, in particular for the diagnostic imaging of a human or animal body organ or tissue by use of the MRI technique.

In a further aspect the invention relates to a manufacturing process for the preparation of the provided ligands, their complex compounds with a paramagnetic metal ion, and the pharmaceutical acceptable salt thereof and their use in the preparation of a diagnostic agent.

According to another aspect, the invention relates to a pharmaceutically acceptable composition comprising at least one paramagnetic complex compound of the invention, or a pharmaceutical salt thereof, in admixture with one or more physiologically acceptable carriers or excipients. Said compositions are useful in particular as MRI contrast media, to provide diagnostically useful images of human or animal body organs or tissues.

Therefore, in another aspect, the present invention refers to a method for the diagnostic imaging of a body organ, tissue or region by use of MRI technique that comprises the use of an effective dose of a compound of the invention.

DETAILED DESCRIPTION OF THE INVENTION

The present invention relates to chelating ligands of formula (I)

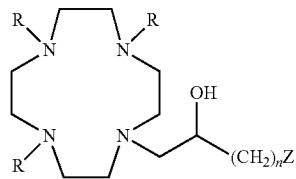

(I)

where:
R is —CH($R_1$)—COOH, where:
$R_1$ is H or a $C_1$-$C_3$ alkyl chain that is optionally substituted by a $C_1$-$C_3$ alkoxy or $C_1$-$C_3$ hydroxyalkoxy group;
n is 1 or 2;
Z is an amine derivative selected from —N($R_2$)($R_3$) and —NHR$_4$; wherein:
$R_2$ is selected from the group consisting of: an aryl ring, a cycloalkyl ring, and a $C_1$-$C_{10}$ alkyl optionally interrupted by one or more oxygen atoms and/or optionally substituted by one or more hydroxyl groups, or by an aryl or cycloalkyl ring;
$R_3$ is selected from the group consisting of: a $C_5$-$C_{12}$ hydroxyalkyl comprising at least 2 hydroxyl groups; a $C_2$-$C_{10}$ hydroxyalkoxyalkylene of formula —(CH$_2$)$_r$—[(O—(CH$_2$)$_r$]$_m$(CH$_2$)$_s$OH; and a group of formula —(CH$_2$)$_s$CH($R_5$)-G; where
s is 0, 1 or 2;
each r is independently 1 or 2;
m is 1, 2 or 3; and where
$R_5$ is H, or an arylalkylene or cycloalkyl-alkylene having up to 3 carbon atoms in the alkylene chain;
G is a group selected from —PO(O$R_6$)$_2$, —PO($R_7$)(O$R_6$) and —COOH; in which
$R_6$ independently of one another is H or $C_1$-$C_5$ alkyl;
$R_7$ is an aryl or cycloalkyl ring, or $C_1$-$C_5$ alkyl which is optionally substituted by an aryl or cycloalkyl ring;
or
$R_2$ and $R_3$ together with the connecting nitrogen atom form a substituted five- or six-membered heterocyclic ring;

$R_4$ is selected from the group consisting of: a cycloalkyl ring; a cycloalkyl-alkylene having up to 3 carbon atom in the alkylene chain; a $C_5$-$C_{12}$ hydroxyalkyl comprising at least 2 hydroxyl groups; a $C_2$-$C_{10}$ hydroxyalkoxyalkylene of formula —(CH$_2$)$_r$—[(O—(CH$_2$)$_r$]$_m$(CH$_2$)$_s$OH; —(CH$_2$)$_m$PO(O$R_6$)$_2$; —(CH$_2$)$_m$PO($R_7$)(O$R_6$); and —(CH$_2$)$_s$CH($R_8$)G; where:
$R_8$ is an arylalkylene or cycloalkyl-alkylene having up to 3 carbon atoms in the alkylene chain; and
m, r, s, $R_6$, $R_7$ and G are as above defined.

Preferably in the above compounds of formula (I) $R_1$ is H.

In the present description, and unless otherwise provided, the expression alkyl comprises within its meaning any linear or branched hydrocarbon chain derived from the corresponding hydrocarbon by removal of one hydrogen atom, preferably comprising up to 12 carbon atoms. In particular "$C_1$-$C_{10}$ alkyl" comprises within its meaning a linear or branched hydrocarbon chain comprising from 1 to 10 carbon atoms such as: methyl, ethyl, propyl, iso-propyl, butyl, iso-butyl, tert-butyl, pentyl, iso-pentyl, tert-pentyl, hexyl, iso-hexyl, heptyl, iso-heptyl, octyl, and the like. Similarly, the term "$C_1$-$C_3$ alkyl" comprises within its meaning a linear or branched hydrocarbon chain comprising from 1 to 3 carbon atoms such as, for instance, methyl, ethyl, propyl and iso-propyl; the term "$C_1$-$C_5$ alkyl" comprises within its meaning a linear or branched hydrocarbon chain comprising from 1 to 5 carbon atoms such as: methyl, ethyl, propyl, iso-propyl, butyl, iso-butyl, tert-butyl, pentyl and the like; and the term "$C_5$-$C_7$ alkyl" comprises within its meaning any linear or branched hydrocarbon chain comprising from 5 to 7 carbon atoms such as pentyl, iso-pentyl, tert-pentyl, hexyl, iso-hexyl, tert-hexyl, heptyl, iso-heptyl and tert-heptyl.

By analogy, the expression "alkylene" comprises within its meaning a bivalent linear or branched hydrocarbon chain derived from any of the corresponding hydrocarbon chains by removal of two hydrogen atoms from different carbon atoms, including $C_1$-$C_5$ alkylene such as for instance a methylene, ethylene, (iso)propylene and so on.

The term "hydroxyalkyl" comprises within its meaning any of the above corresponding alkyl moiety wherein one or more hydrogen atoms are replaced by hydroxyl groups. Suitable examples include $C_1$-$C_3$ hydroxyalkyl such as hydroxymethyl (—CH$_2$OH), hydroxyethyl (—CH$_2$CH$_2$OH), hydroxypropyl (—CH$_2$CH$_2$CH$_2$OH), dihydroxypropyl, (—CH(CH$_2$OH)$_2$ and CH$_2$CH$_2$OHCH$_2$OH) and the like, and polyhydroxyalkyls or "polyols", as used herein interchangeably, in which at least two and, preferably, three or more hydrogen atoms of the hydrocarbon chain are replaced by hydroxyl groups.

For instance, and unless otherwise provided, the expression "$C_5$-$C_{12}$ polyol" (or "$C_5$-$C_{12}$ polyhydroxyalkyl") comprises within its meaning any of the corresponding $C_5$-$C_{12}$ alkyl moiety in which 2 or more, e.g. from 2 to 11 hydrogen atoms have been replaced by hydroxyl groups. Among them, $C_5$-$C_{10}$ polyols are preferred, and $C_5$-$C_7$ polyols are particularly preferred. Examples of $C_5$-$C_7$ polyols include pentyl-polyols (or polyhydroxypentyls) such as pentyl-diols, pentyl-triols, pentyl-tetraols and pentyl-pentaol, respectively comprising from 2, 3, 4 and 5 hydroxyl groups on a $C_5$ alkyl chain; hexyl-polyols (or polyhydroxyhexyls) analogously comprising from 2 to 6 hydroxyl groups on a $C_6$ alkyl chain; and heptyl-polyols (or polyhydroxyheptyls) comprising from 2 to 7 hydroxyl groups on a $C_7$ alkyl chain.

The term "alkoxy" comprises within its meaning an alkyl moiety as above defined further comprising one or more oxygen atoms; examples include, for instance, alkyl-oxy (or —Oalkyl) groups such as methoxy, ethoxy, n-propoxy, isopropoxy and the like, an alkyl-(poly)oxy in which the alkyl chain is interrupted by one or more, e.g. up to three, oxygen atoms.

The term "hydroxyalkoxy" comprises within its meaning any of the above alkoxy residues further comprising one or more hydroxyl (—OH) in the alkyl chain such as, for example, —OCH$_2$OH, —OCH$_2$CH$_2$OH, —OCH$_2$CH$_2$CH$_2$OH, —OCH$_2$OCH$_2$OH, —OCH$_2$CH$_2$OCH$_2$CH$_2$OH, —OCH$_2$CH(OH)CH$_2$—OCH$_2$CH$_2$OH, and the like.

The term "hydroxyalkoxyalkylene" (or "hydroxyalkoxy-alkylene") comprises within its meaning any of the above hydroxyalkoxy where the linking group of the residue is an alkylene chain —(CH$_2$)$_r$—, including C$_2$-C$_{10}$ hydroxyalkoxy-alkylenes of formula —(CH$_2$)$_r$—[(O—(CH$_2$)$_r$]$_m$(CH$_2$)$_s$OH, where m, r, and s are as above defined.

The term "aminopolyol" (or "aminopolyhydroxyalkyl" or "polyhydroxy-aminoalkyl", as herein used interchangeably) comprises within its meaning a C$_5$-C$_{12}$ hydrocarbon chain, e.g. comprising from 5 to 12 carbon atoms, which is substituted by 2 or more, for instance from 2 to 11 hydroxyl groups, and comprises an amino group bridging the polyhydroxylated chain, or polyol, with the rest of the macrocyclic molecule. Preferred are C$_5$-C$_7$ aminopolyols, e.g. comprising a hydrocarbon chain including 5, 6 or 7 carbon atoms, which is substituted by 2 or more, for instance 2, 3, 4, 5, or 6 hydroxyl groups, and a bridging amino group as above said. Preferably, the amino group is linked to the 1-C carbon atom of the polyhydroxylated chain (polyol), thereby leading to corresponding 1-amino(C$_5$-C$_{12}$)polyols. The amino group can be either a secondary amino group, i.e. —NH—[(C$_5$-C$_{12}$)polyol], or a tertiary amino group, where the nitrogen atom is, in addition, preferably bound to an alkyl chain, preferably a C$_1$-C$_3$ alkyl, i.e. an aminoalkyl-polyol of formula —N[alkyl][(C$_5$-C$_{12}$)polyol].

Suitable examples of aminopolyols according to the invention thus include polyhydroxylated aminoalkyl groups of formula —N(R$_9$)(R$_{10}$) in which:

R$_9$ is H or a C$_1$-C$_3$ alkyl e.g. propyl, ethyl or, preferably, methyl; and R$_{10}$ is a C$_5$-C$_{12}$ polyol.

Preferred according to the invention are aminopolyols of the above general formula in which R$_{10}$ is a C$_5$-C$_7$ polyol selected from pentyl(poly)ols (or polyhydroxypentyls) comprising at least 2, and preferably from 2 to 4 hydroxyl groups on the C$_5$ alkyl chain; hexyl(poly)ols comprising at least 2, and preferably from 2 to 5 hydroxyl groups on the C$_6$ alkyl chain; and heptyl(poly)ols comprising at least 2 and, and preferably from 3 to 6 hydroxyl groups on the C$_7$ alkyl chain, and R$_9$ is H or a methyl group.

Particularly preferred according to the invention are aminopolyols selected from the group consisting of 1-amino-1-deoxy-pentitols of formula

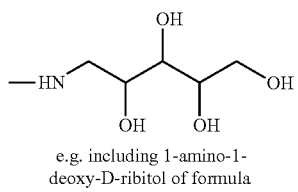

e.g. including 1-amino-1-deoxy-D-ribitol of formula

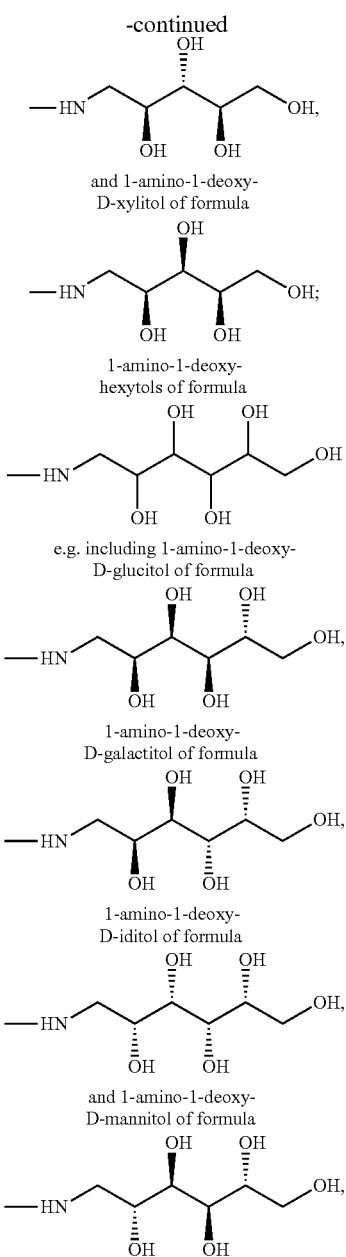

and 1-amino-1-deoxy-D-xylitol of formula 1-amino-1-deoxy-hexytols of formula e.g. including 1-amino-1-deoxy-D-glucitol of formula 1-amino-1-deoxy-D-galactitol of formula 1-amino-1-deoxy-D-iditol of formula and 1-amino-1-deoxy-D-mannitol of formula as well as the respective aminoalkyl-polyols where the hydrogen atom bound to nitrogen is replaced by R$_9$ with the above meanings.

The expression "carboxyl" comprises within its meaning a residue of formula —COOH, or comprising said —COOH residue, such as the groups of formula —(CH$_2$)$_s$—COOH or —[O(CH$_2$)$_n$]$_s$—COOH, where s and n are as above defined.

The term "aryl" or "aryl ring" refers to an aromatic hydrocarbon and, preferably, a phenyl ring. Unless otherwise specifically provided, aryls according to the invention can be either unsubstituted or substituted with one or more, equal or different, substituent groups, for instance selected from hydroxyl (OH), halogen, C$_1$-C$_3$ alkyl, C$_1$-C$_3$ alkoxy, C$_1$-C$_3$ hydroxyalkyl, carboxy, carbamoyl, nitro, —NH$_2$, and C$_1$-C$_3$ alkyl- or dialkylamino; preferably from hydroxyl, halogen, C$_1$-C$_3$ alkyl or alkoxy, and carboxy and, more preferably, from C$_1$-C$_3$ alkyl or alkoxy, —CH$_2$COOH, and —COOH.

The term "cycloalkyl ring" as used herein refers to a cycloaliphatic ring, and, preferably, a $C_5$-$C_7$ carbocyclic ring e.g. a cyclohexyl ring. Unless otherwise specifically provided, cycloalkyls according to the invention can be either unsubstituted or substituted with one or more, equal or different, substituent groups for instance selected from hydroxyl halogen, $C_1$-$C_3$ alkyl, $C_1$-$C_3$ alkoxy, $C_1$-$C_3$ hydroxyalkyl, carboxyl, carbamoyl, nitro, —$NH_2$, and $C_1$-$C_3$ alkyl- or dialkylamino; preferably from hydroxyl, halogen, $C_1$-$C_3$ alkyl or alkoxy, and carboxy and, more preferably, from $C_1$-$C_3$ alkyl or alkoxy, —$CH_2COOH$, and —COOH.

The term "heterocyclic ring" (or "heterocycle") comprises within its meaning a 5- or 6-membered saturated cyclic residue comprising a nitrogen atom in the cyclic chain, and, optionally, another, equal or different, heteroatom selected e.g. from N, O and S. Suitable examples include heterocycles such as pyrrolidine, piperazine, morpholine and piperidine, wherein this last is particularly preferred. Unless otherwise specifically provided, the nitrogen-containing heterocycles according to the invention comprise one or more substituents groups linked to the carbon atom(s) of the cycle, selected e.g. from hydroxyl, $C_1$-$C_3$ hydroxyalkyl, $C_1$-$C_3$ alkoxy, $C_1$-$C_3$ hydroxyalkoxy, $C_1$-$C_3$ hydroxyalkoxy-alkyl, and carboxyl such as —$(CH_2)_s$—COOH or —$[O(CH_2)_n]_s$—COOH, as above defined.

From all the above, having defined the meaning for alkyl, alkylene, aryl and cycloalkyl, any composite-name such as alkyl-aryl, aryl-alkylene, cycloalkyl-alkylene and the like should be clear to a skilled person.

For instance the term alkylaryl (or alkyl-aryl) comprises within its meaning an aryl group further substituted by an alkyl, (e.g. p-ethyl-phenyl; $pC_2H_5$—$C_6H_5$—) while the term arylalkylene (or aryl-alkylene) or cycloalkyl-alkylene comprises within its meaning an alkyl further substituted by an aryl (e.g. phenyl-ethylene=$C_6H_5$—$C_2H_4$—) or by a cycloalkyl (e.g. cyclohexyl-ethylene=$C_6H_{11}$—$C_2H_4$—); and the like.

In the present description the term "protecting group" designates a protective group adapted for preserving the function of the group to which it is bound. Specifically, protective groups are used to preserve amino, hydroxyl or carboxyl functions. Appropriate carboxyl protective groups may thus include, for example, benzyl, alkyl e.g. tert-butyl or benzyl esters, or other substituents commonly used for the protection of such functions, which are all well known to those skilled in the art. [see, for a general reference, T. W. Green and P. G. M. Wuts; *Protective Groups in Organic Synthesis,* Wiley, N.Y. 1999, third edition].

Moreover, the terms "moiety" or "moieties", "residue" or "residues" are herewith intended to define the residual portion of a given molecule once properly attached or conjugated, either directly or through any suitable linker, to the rest of the molecule.

The compounds of the above formula (I) may have one or more asymmetric carbon atom, otherwise referred to as a chiral carbon atom, and may thus give rise to diastereomers and optical isomers. Unless otherwise provided, the present invention further includes all such possible individual diastereomers as well as their racemic mixtures, their substantially pure resolved enantiomers, all possible geometric isomers, and the pharmaceutical acceptable salts thereof.

The present invention further relates to compounds of the above formula (I) in which each of the acidic groups, either including the carboxylic groups R linked to the nitrogen atoms of the macrocycle or any other optional acidic group on the hydroxylated pendant arm, may be in the form of a pharmaceutically acceptable salt, or of a derivative in which the acidic group is suitably protected with an appropriate protecting group (Pg) as above defined, e.g., preferably, of a $C_1$-$C_5$ alkyl ester and, more preferably, of a tert-butyl ester, finding for instance application as such, or as suitable precursor or intermediate compound in the preparation of a desided compound of formula (I) or of a suitable paramagnetic complex or salt thereof.

In one embodiment, the compounds of formula (I) comprise an amine derivative Z linked to the carbon atom bearing the hydroxyl group through an alkylene chain including 1 or 2 carbon atoms.

In a preferred embodiment, the present invention relates to compounds of formula (I) in which Z is a tertiary amine derivative of formula —$N(R_2)(R_3)$.

Suitable examples includes amine derivatives of formula (II)

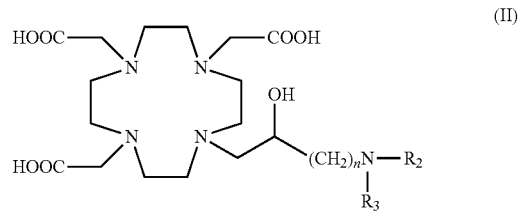

in which n is an integer from 1 to 2, and $R_2$ and $R_3$ are as defined for the compounds of formula (I).

In one embodiment the invention relates to compounds according to the above formula (II) in which $R_3$ is a group of formula —$(CH_2)_s CH(R_5)$-G.

In particular, in one embodiment the invention relates to compounds of formula (II A)

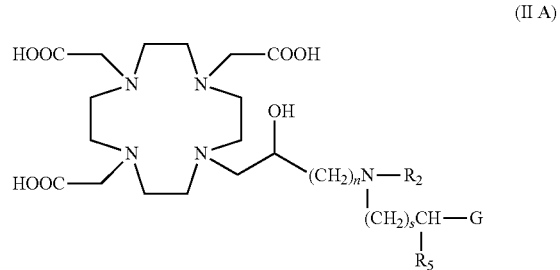

in which n is 1 or 2 and, preferably is 1, and s, G, $R_2$ and $R_5$ are as defined for the compounds of formula (I).

Suitable embodiments comprise compounds of formula (IIA) in which:

n is 1;
G is selected from the groups of formula —$PO(OR_6)_2$, —COOH and —$PO(R_7)(OR_6)$ in which $R_6$ is H or a tert-butyl and, preferably, is H; and $R_7$ is an optionally substituted phenyl or cyclohexyl ring, or a $C_1$-$C_5$ and, preferably, $C_1$-$C_3$ alkyl such as methyl, ethyl or propyl which is substituted or not by an aryl or cycloalkyl ring, e.g., preferably, a benzyl, phenyl-ethylene, cyclohexyl-methylene or cyclohexyl-ethylene group;
s is 0, 1 or 2, preferably 0 or 1;
$R_5$ is H or an arylalkylene or cycloalkyl-alkylene having up to 3 carbon atoms in the alkylene chain; and
$R_2$ is as defined for the compounds of formula (I).

Preferably in the above compounds of formula (II A) $R_2$ is an aryl or cycloalkyl ring such as a phenyl or a cyclohexyl which can be either unsubstituted or substituted by a group e.g. selected from $C_1$-$C_3$ alkyl, $C_1$-$C_3$ alkoxy and $(CH_2)_n$COOH; or is a $C_1$-$C_{10}$ alkyl which is optionally interrupted by 1, 2 or 3 oxygen atoms and/or optionally substituted by one or more hydroxyl groups, e.g. 1, 2, 3, 4 or 5 hydroxyl groups, or by an optionally substituted aryl or cycloalkyl ring.

More preferably, $R_2$ is a phenyl or a cyclohexyl ring, or a $C_1$-$C_7$ alkyl which is optionally substituted by one or more hydroxyl groups or by an optionally substituted phenyl or cyclohexyl ring, such as a methyl, ethyl, propyl, isopropyl and tert-butyl chain substituted or not by one or more hydroxyl groups, e.g. including hydroxymethyl, hydroxyethyl, hydroxypropyl, 1,3- and 2,3-dihydroxypropyl and 2-(hydroxymethyl)-1,3-dihydroxypropyl, or by an phenyl or a cycloalkyl ring, e.g. including a benzyl, phenyl-ethylene, cyclohexyl-methylene and cyclohexyl-ethylene group.

Particularly preferred are compounds of formula (II A) in which:

n is 1;

$R_2$ is selected from the group consisting of: a $C_1$-$C_7$ alkyl selected from methyl, ethyl, propyl, isopropyl and tert-butyl; the mono-, bis- and tris-hydroxyalkyl derivatives thereof e.g. including hydroxymethyl, hydroxyethyl, hydroxypropyl, 1,3- and 2,3-dihydroxypropyls and 2-(hydroxymethyl)-1,3-dihydroxypropyl; and an aryl-alkylene or a cycloalkyl-alkylene preferably including up to 3 carbon atom in the alkylene chain, such as benzyl, phenyl-ethyl, cyclohexyl-methyl and cyclohexyl-ethylene;

s is 0 or 1;

$R_5$ is H or an arylalkylene or cycloalkyl-alkylene selected from benzyl, phenyl-ethylene, cyclohexyl-methylene and cyclohexyl-ethyl; and G is —PO(OH)$_2$ or —COOH.

In another embodiment the invention relates to an amine compound according to the above formula (II) in which $R_3$ is a $C_2$-$C_{10}$ hydroxyalkoxyalkylene of formula —(CH$_2$)$_r$—[(O—(CH$_2$)$_r$]$_m$(CH$_2$)$_s$OH, and $R_2$ is as defined for the compounds of formula (I).

More particularly, in another embodiment the invention relates to amine derivatives of formula (II B)

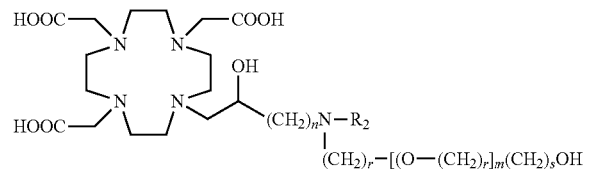

(II B)

in which:
n is 1 or 2 and, preferably, 1;
each r is independently 1 or 2;
m is 1, 2 or 3;
s is 0, 1 or 2; and
$R_2$ is as defined for the compounds of formula (I).

Suitable examples include amino derivatives of formula (II B) in which $R_2$ is a $C_1$-$C_{10}$ alkyl optionally interrupted by one or more oxygen atoms and/or optionally substituted by one or more hydroxyl groups or by an aryl or a cycloalkyl ring.

Preferably, in the above compounds of formula (II B) $R_2$ is $C_1$-$C_{10}$ alkyl chain substituted by one or more, e.g. from 1 to 3 hydroxyl groups, and optionally, interrupted by 1, 2 or 3 oxygen atoms.

In one preferred embodiment, the invention relates to amine compounds of the above formula (II B) in which $R_2$ represents a second hydroxyalkoxyalkylene chain of formula —(CH$_2$)$_r$—[(O—(CH$_2$)$_r$]$_m$(CH$_2$)$_s$OH where r, s and m are as above said. Preferably, the chains are each independently selected from groups of formula —CH$_2$(OCH$_2$CH$_2$)$_s$OCH$_2$OH, —(CH$_2$)$_r$—O(CH$_2$)$_r$OH and —CH$_2$(CH$_2$OCH$_2$)$_r$CH$_2$OH where m, r and s are as said.

More preferably, the hydroxyalkoxyalkylene chains linked to the nitrogen atom are equal to each other and are selected from the groups of formula —CH$_2$(OCH$_2$CH$_2$)$_s$OCH$_2$OH and of formula —CH$_2$(CH$_2$OCH$_2$)$_r$CH$_2$OH.

In a particularly preferred embodiment, the invention relates to amine compounds of formula (II C)

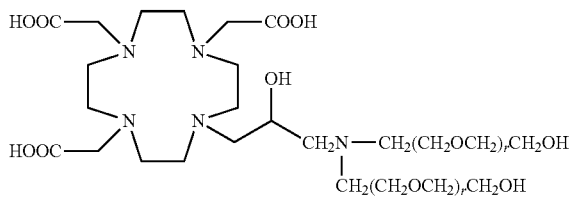

(II C)

in which r is 1 or 2 and, preferably, 1.

Compounds of formula (I) according to the invention further include amine derivatives of formula (II) in which $R_2$ and $R_3$ together with the connecting nitrogen atom form a substituted five- or six-membered saturated heterocyclic ring.

Examples of said heterocyclic rings include morpholine, pyrrolidine and, preferably, piperidine derivatives having one or more substituents groups linked to the carbon atom(s) of the cycle.

In a preferred embodiment the invention relates to amine compounds of formula (I) in which Z is a piperidine derivative.

Suitable examples include compounds of formula (III)

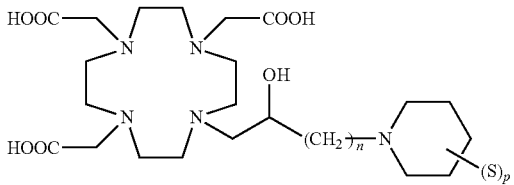

(III)

in which:
n is 1 or 2 and, preferably, 1;
p is an integer from 1 to 8; and
S is a substituent group linked to a carbon atom of the piperidine ring.

In one embodiment the invention relates to compounds of formula (III) in which p is 1, and S is a substituent group selected from the group consisting of: hydroxyl, $C_1$-$C_3$ hydroxyalkyl, $C_1$-$C_3$ alkoxy, $C_1$-$C_3$ hydroxyalkoxy, $C_1$-$C_3$ hydroxyalkoxy-alkylene, and carboxyl and, preferably, from hydroxyl, $C_1$-$C_3$ hydroxyalkyl, $C_1$-$C_3$ hydroxyalkoxy and carboxyl such as —$(CH_2)_s$—COOH or —$OCH_2$—COOH.

Among them, preferred are compounds of formula (III) in which S is a substituent group selected form hydroxyl, —$CH_2OH$, and —COOH that is linked to the C3 carbon atom of the ring.

In a preferred embodiment the invention relates to compounds of the above formula (III) where p is an integer from 2 to 8, which comprise a piperidine ring having from 2 to 8, preferably from 2 to 6 and, more preferably, from 3 to 5 e.g. 3, 4, or 5 substituent groups S linked to one or more carbon atom(s) of the ring, that are each independently selected from hydroxyl, $C_1$-$C_3$ hydroxyalkyl, $C_1$-$C_3$ alkoxy, $C_1$-$C_3$ hydroxyalkoxy, $C_1$-$C_3$ hydroxyalkoxy-alkylene, and carboxyl such as —$(CH_2)_s$—COOH or —$(OCH_2)_s$—COOH.

Preferred among them are compounds of formula (III A)

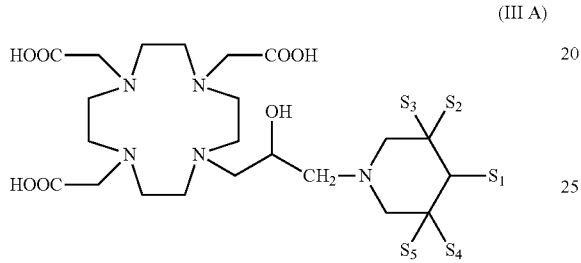

(III A)

in which the substituent groups $S_1$-$S_5$ are each independently selected from the group consisting of: H, hydroxyl, $C_1$-$C_3$ hydroxyalkyl, $C_1$-$C_3$ hydroxyalkoxy and $C_1$-$C_3$ hydroxyalkoxy-alkylene, providing that at least 3 of the $S_1$-$S_5$ substituent groups are other than H.

Suitable examples include compounds of formula (III A) in which the substituted pyridine ring is a group of formula:

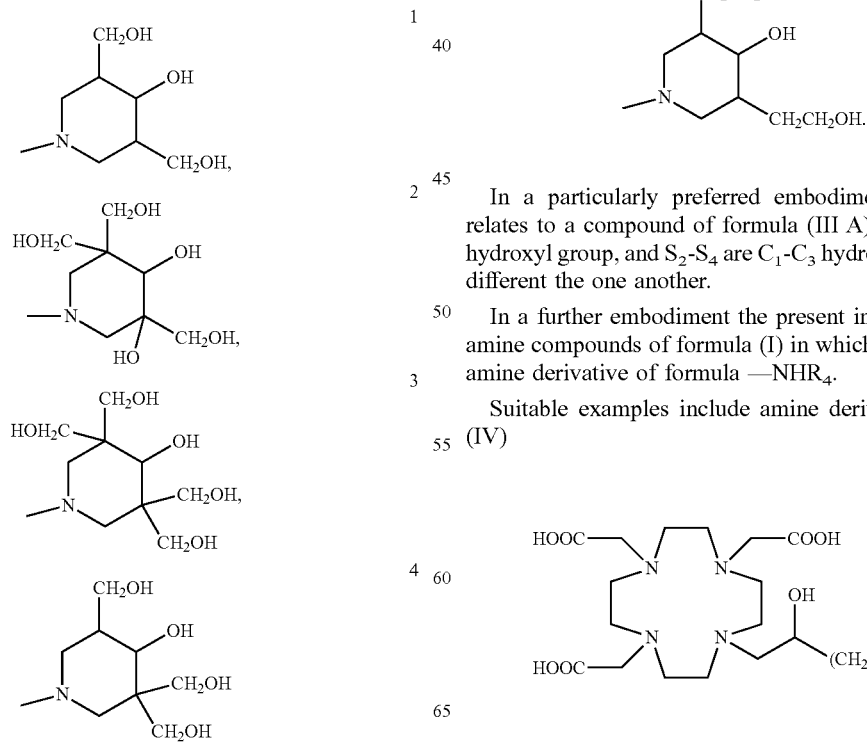

In a particularly preferred embodiment the invention relates to a compound of formula (III A) in which $S_1$ is a hydroxyl group, and $S_2$-$S_4$ are $C_1$-$C_3$ hydroxyalkyls equal or different the one another.

In a further embodiment the present invention relates to amine compounds of formula (I) in which Z is a secondary amine derivative of formula —$NHR_4$.

Suitable examples include amine derivative of formula (IV)

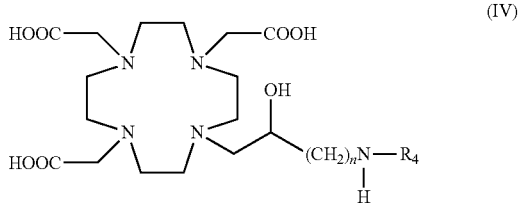

(IV)

in which n is an integer from 1 to 2, and $R_4$ is as above defined for the compounds of formula (I).

Preferably, $R_4$ is selected from: an optionally substituted cyclohexyl, or a cyclohexyl-alkylene having up to 3 carbon atoms in the alkylene chain, e.g. a cyclohexyl-methylene or cyclohexyl-ethylene; a group of formula $—(CH_2)_mPO(R_2)(OR_6)$ or $—(CH_2)_mPO(OR_8)_2$, where m is an integer from 1 to 3, $R_6$ is H or a tert-butyl and, preferably, H, and $R_7$ is an optionally substituted phenyl or cyclohexyl, or a $C_1$-$C_5$ and, preferably, $C_1$-$C_3$ alkyl such as methyl, ethyl or propyl substituted or not by an aryl or cycloalkyl ring, e.g., preferably, a benzyl, phenyl-ethylene, cyclohexyl-methylene or cyclohexyl-ethylene group; a $C_2$-$C_{10}$ hydroxyalkoxyalkylene of formula $—(CH_2)_r—[(O—(CH_2)_r]_m(CH_2)_sOH$ where r, s and m are as above said for the compounds of formula (I); and a group of formula $—(CH_2)_sCH(R_8)G$, where s is 0, 1 o 2 and, preferably, is 0 or 1, $R_8$ is an optionally substituted arylalkylene or cycloalkyl-alkylene having up to 3 carbon atoms in the alkylene chain, and G is a group selected from $—PO(OR_8)_2$, $—PO(R_7)(OR_8)$ and $—COOH$, where $R_6$ and $R_7$ are as above said.

In particular, in one preferred embodiment the invention relates to amine derivatives according to the above formula (IV) in which n is 1 and $R_4$ is a group of formula $—(CH_2)_mPO(R_2)(OR_8)$ and, more preferably, of formula $—(CH_2)_mPO(OR_8)_2$, where m is an integer from 1 to 3, and preferably is 1 or 2, $R_6$ is H and $R_7$ is an optionally substituted phenyl or cyclohexyl, or a group selected from methyl, ethyl, propyl, benzyl, phenyl-ethylene, cyclohexyl-methylene and cyclohexyl-ethylene.

In another preferred embodiment the invention relates to amine derivatives according to the above formula (IV), having the formula (IV A)

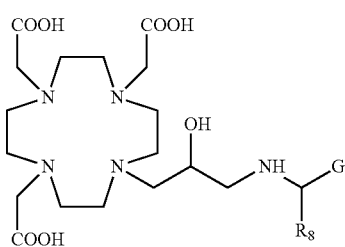

(IV A)

where $R_8$ is an optionally substituted aryl-alkylene or cyclohexyl-alkylene as above said and, preferably, selected from benzyl, phenyl-ethylene, cyclohexyl-methylene and cyclohexyl-ethylene, and G is a group selected from $—PO(OR_6)_2$, $—PO(R_7)(OR_6)$ and $—COOH$, and, more preferably, from $—PO(OR_6)_2$ and $—COOH$, where $R_6$ preferably is H.

In a preferred embodiment, the invention relates to amine derivatives according to the formula (I) in which Z is a tertiary or a secondary $C_5$-$C_{12}$ aminopolyol.

Suitable examples include compounds of the above formula (I) in which Z is an amine derivative selected from $—N(R_2)(R_3)$ or $—NHR_4$ in which $R_3$ and $R_4$ are a $C_5$-$C_{12}$ polyol and $R_2$ is as above defined for the compounds of formula (I).

Preferred among them are aminopolyol derivatives of formula (V)

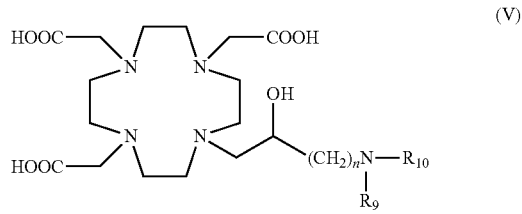

in which:
n is 1;
$R_9$ is H or a $C_1$-$C_3$ alkyl e.g. propyl, ethyl or, preferably, methyl; and
$R_{10}$ is a $C_5$-$C_{12}$ polyol.

Preferred according to the invention are aminopolyols derivatives of the above formula (V) in which $R_{10}$ is a $C_5$-$C_7$ polyol, e.g. selected from pentyl(poly)ols (or polyhydroxypentyls) comprising at least 2, and preferably from 2 to 4 hydroxyl groups on the $C_5$ alkyl chain; hexyl(poly)ols comprising at least 2, and preferably from 2 to 5 hydroxyl groups on the $C_6$ alkyl chain; and heptyl(poly)ols comprising at least 2 and, and preferably from 3 to 6 hydroxyl groups on the $C_7$ alkyl chain, and $R_9$ is H or a methyl group.

Suitable examples include penty(poly)ols such as pentyl-diols, pentyl-triols, and pentyl-tetraols; hexyl(poly)ols such as hexyl-diols, hexyl-triols, hexyl-tetraols and hexyl-pentaol; and heptyl(poly)ols such as heptyl-diols, heptyl-triols, heptyl-tetraols, heptyl-pentaol and heptyl-hexaols.

Particularly preferred according to the invention are aminopolyol derivatives of the above formula (V) in which:

$R_9$ is H or methyl; and
$R_{10}$ is selected from a pentyl-tetraol of formula

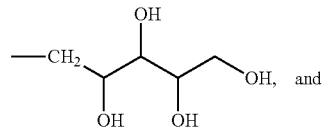, and a hexyl-pentaol of formula

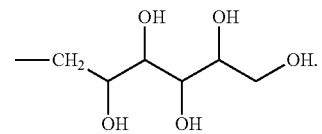.

In particular, in a preferred embodiment the invention relates to compounds according to the formula (I) in which Z is the residue of an aminopolyol selected from the group consisting of 1-amino-1-deoxy-pentitols such as 1-amino-1-deoxy ribitol, 1-amino-1-deoxy-xylitol and 1-amino-1-deoxy-arabitol; 1-amino-1-deoxy-hexitols such as 1-amino-1-deoxy-glucitol, 1-amino-deoxy-galactitol, 1-amino-1-deoxy-allitol, 1-amino-1-deoxy-mannitol and 1-amino-1-deoxy-iditol; and 1-amino-1-deoxy-heptitols such as 1-amino-1-deoxy-glycero-manno-heptitol, as well as the N—($C_1$-$C_3$)alkyl derivatives thereof, preferably N-methyl.

More preferably, Z is the residue of a 1-amino-1-deoxy-hexitol e.g. selected from the group consisting of 1-amino-1-deoxy-glucitol, 1-amino-deoxy-galactitol, 1-amino-1-deoxy-mannitol, 1-amino-1-deoxy-ditol, and the N-methyl derivatives thereof.

In a particularly preferred embodiment the invention relates to a compound of formula (I) in which Z is a 1-deoxy-1-amino-D-glucitol or, especially, a 1-deoxy-1-(methylamino)-D-glucitol residue having, respectively, the formula

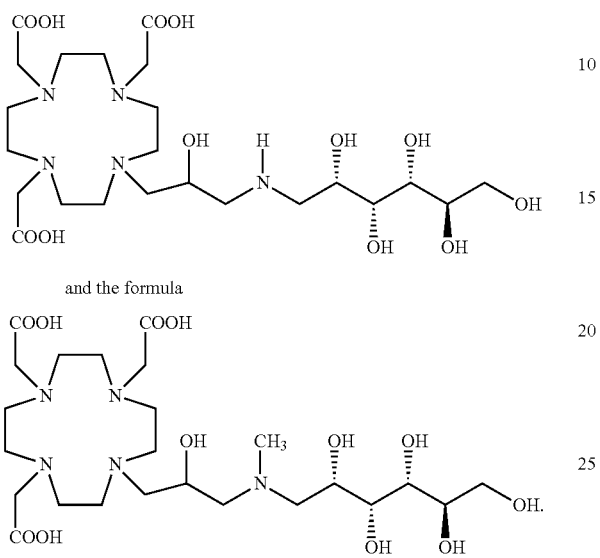

and the formula

Particularly preferred compounds are those compounds of formula (I), or salts thereof, selected from the group consisting of:

Compound 1
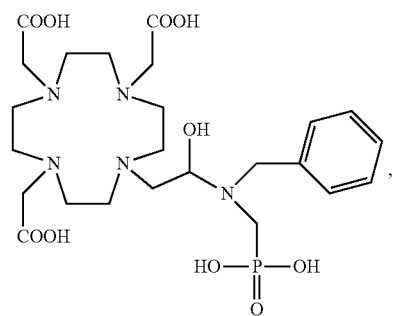

Compound 2
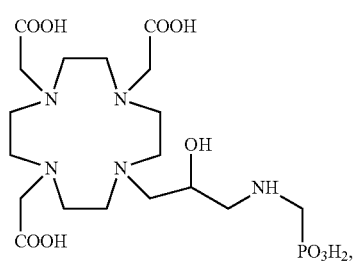

Compound 3
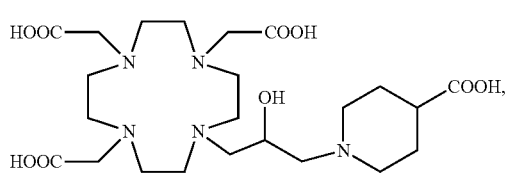

Compound 4
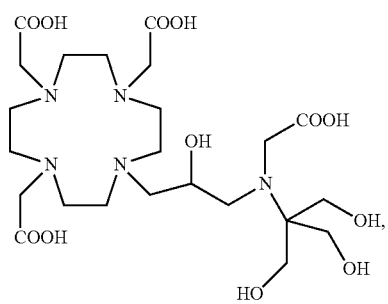

Compound 5
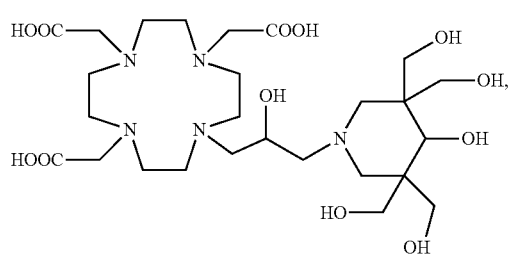

Compound 6
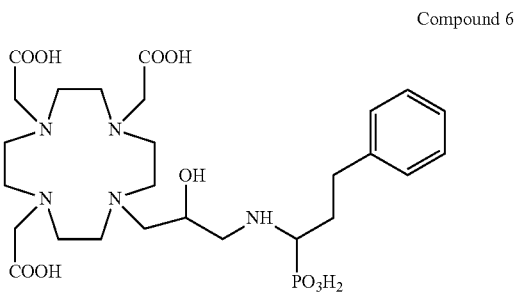

Compound 7
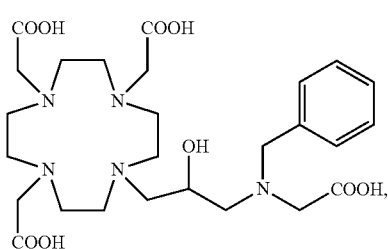

Compound 8
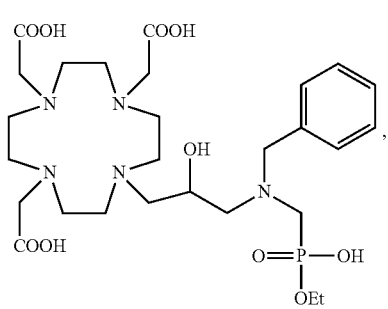

Compound 9
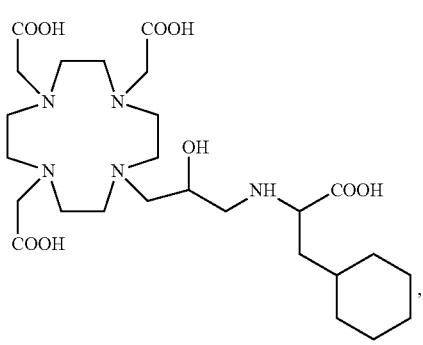
Compound 10
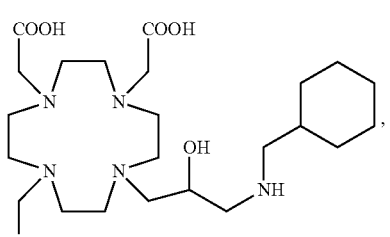
Compound 11
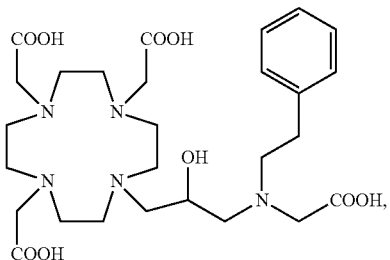
Compound 12
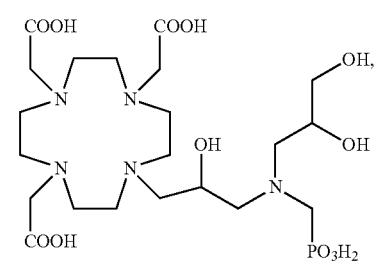
Compound 13
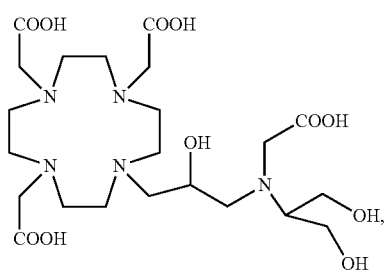
Compound 14
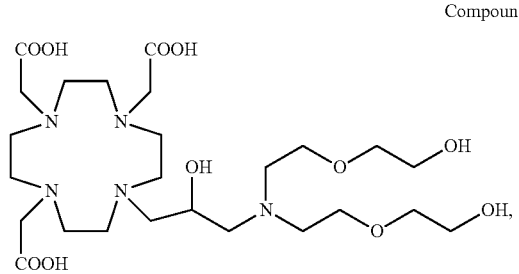
Compound 15
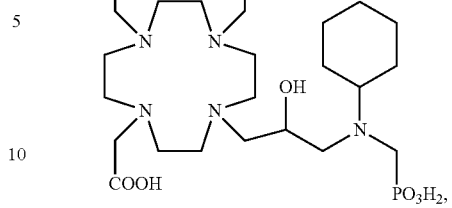
Compound 16
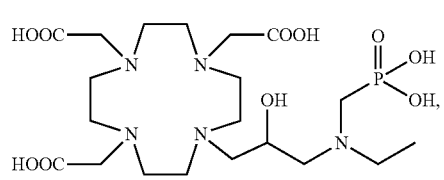
Compound 17
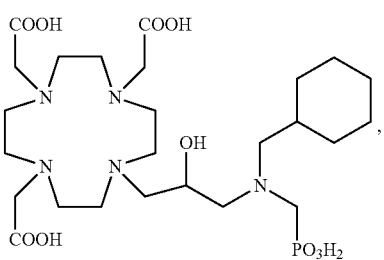
Compound 18
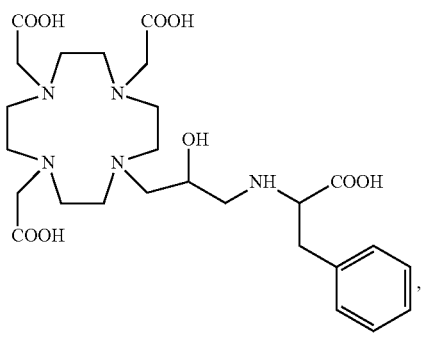
Compound 19
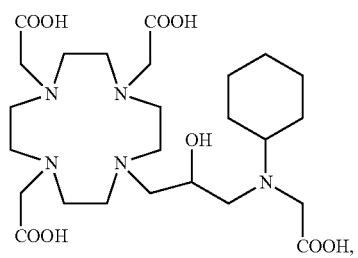
Compound 20
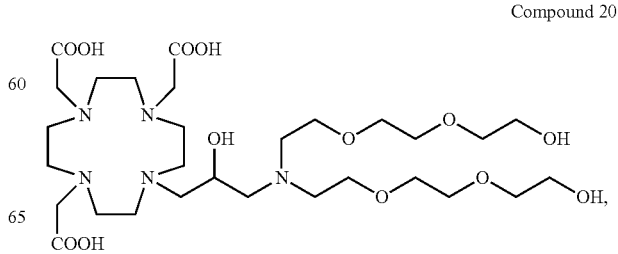

-continued

Compound 21

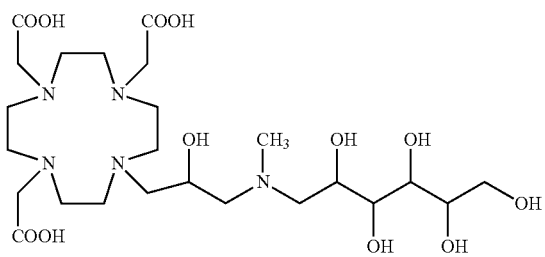

In a further aspect the invention relates to chelated complexes of the compounds of formula (I), hence encompassing those of formulae from (II) to (V), with a paramagnetic metal ion, or a radionuclide, or of a suitable salt thereof.

Preferably, the paramagnetic metal ion is selected in the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ or $Mn^{2+}$. More preferably, the paramagnetic metal ion is $Gd^{3+}$.

Preferred radionuclides according to the invention providing complexes for use in radiotherapy or radiodiagnostics include $^{105}$Rh, $^{117m}$Sn, $^{99m}$Tc, $^{94m}$Tc, $^{203}$Pb, $^{67}$Ga, $^{68}$Ga, $^{44}$Sc, $^{72}$As, $^{110}$In, $^{111}$In, $^{113}$In, $^{90}$Y, $^{97}$Ru, $^{60}$Cu, $^{62}$Cu, $^{64}$Cu, $^{52}$Fe, $^{51}$Mn, $^{140}$La, $^{175}$Yb, $^{153}$Sm, $^{166}$Ho, $^{149}$Pm, $^{177}$Lu, $^{186/188}$Re, $^{165}$Dy, $^{166}$Dy, $^{142}$Pr, $^{159}$Gd, $^{211}$Bi, $^{212}$Bi, $^{213}$Bi, $^{214}$Bi, $^{149}$Pm, $^{67}$Cu, $^{198}$Au, $^{199}$Au, $^{161}$Tb, $^{167}$Tm, and $^{51}$Cr.

Both the compounds of formula (I), thus including those of formulae (II) to (V), and the paramagnetic chelates thereof can also be in the form of a pharmaceutically acceptable salt, particularly as an addition salt with a physiologically compatible base or acid.

The term "pharmaceutically acceptable salt", as used herein, refers to derivatives of the compounds of the invention wherein the parent compound is suitably modified by converting any of the free acid or basic groups, if present, into the corresponding addition salt with any base or acid conventionally intended as being pharmaceutically acceptable.

Preferred cations of inorganic bases which can be suitably used to prepare a salt of the complexes or the ligands of the invention comprise, for instance, ions of alkali or alkaline-earth metals such as potassium, sodium, calcium or magnesium.

Preferred cations of organic bases comprise, for instance, those of primary, secondary and tertiary amines such as, for instance, ethanolamine, diethanolamine, morpholine, glucamine, N-methylglucamine, N,N-dimethylglucamine.

Preferred anions of inorganic acids which can be suitably used to prepare salts of the complexes of the invention comprise the ions of halo acids, for instance chlorides, bromides or iodides, as well as of other suitable ions such as sulfate.

Preferred anions of organic acids comprise those routinely used in pharmaceutical techniques for the salification preparation of salts of basic substances such as, for instance, acetate, succinate, citrate, fumarate, maleate or oxalate.

Preferred cations and anions of amino acids comprise, for instance, those of taurine, glycine, lysine, arginine, ornithine or of aspartic and glutamic acids.

The preparation of the chelating compounds of the invention and of the chelate complexes thereof, either as such or in the form of physiologically acceptable salts, represent a further object of the invention. Where not differently mentioned hereinafter, in particular when referring to general preparation methods, methods of use or pharmaceutical formulations, it is understood that the term "compounds of formula (I)" encompasses also the compounds of formulae (II) to (V) as well as the specific chelating compounds of the invention disclosed herein.

Compounds of formula (I), and the chelated complexes thereof, and salts thereof, may be prepared through a general synthetic process comprising the following steps:
 a) Obtaining a macrocyclic substrate 1 in a suitable protected form, e.g. in which the carboxylic groups of the substrate are protected as tert-butyl esters;
 b) Obtaining an alkylating molecule 2, in which any optional functional group(s) not involved with the coupling reaction with the substrate 1 is, optionally, suitably protected;
 c) Coupling the protected substrate 1 with the alkylating molecule 2, to give the desired compound of formula (I) in a suitably protected form or, alternatively, an intermediate thereof 3;
 d) Optionally converting the obtained intermediate in the suitably protected compound of formula (I);
 e) Removing any protecting group and isolating the chelating ligand of formula (I); and
 f) Complexing the obtained ligand with a suitable paramagnetic metal ion and isolating the chelate complex, or the salt thereof.

To this extent, and unless otherwise indicated, the term "intermediate" (e.g. with reference to the compound 3 deriving from the reaction of the macrocyclic substrate 1 with an alkylating molecule 2) refers to a molecule that requires one (or more) further reactions, e.g. a reduction, an additional alkylation and so on, to give the desired product, i.e. in the specific case of the above general scheme, in a suitably protected compound of formula (I) according to step d). The single steps of the above general process, comprehensive of any variant thereof, particularly when referring to the steps of protection/deprotection and activation of known functional groups, may be carried out according to conventional methods known in the art.

For instance, suitable substrates 1A and 1B according to the step a) of the process of the invention, of formula

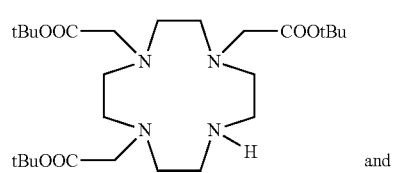

1A and

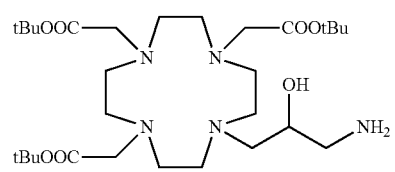

1B in which all carboxyl groups are suitably protected as tert-butyl esters, may be obtained e.g. as disclosed in Org. Synth. 2008, 85, 10 and U.S. Pat. No. 7,208,140, respectively.

Appropriate alkylating molecules 2 for the use of the invention are commercially available, or may easily be prepared according to procedures known to those skilled in the relevant art. Examples of specific procedures for the preparation of protected alkylating molecules 2, their coupling with the appropriate substrate molecule 1, and optional conversion of the obtained intermediates to the desired compound of formula (I) are provided in the experimental section, together with relevant operational details.

As a general reference on possible protecting groups, and cleavage conditions, e.g. to implement the step e) of the above general synthetic procedure, see the above cited "T. W. Green and P. G. M. Wuts; Protective groups in organic synthesis" Wiley 3$^{rd}$ Ed. Chapters 5 and 7.

The complexation of the compounds of formula (I) e.g. obtained from step f) of former general preparation scheme with a paramagnetic ion and, particularly, with gadolinium, may be performed, for instance, by stoichiometric addition of a suitable Gd(III) derivative, particularly a Gd(III) salt or oxide, to a solution of the ligand, e.g. by working according to well-known experimental methods, for instance as reported in EP 230893.

Finally, optional salification of the compounds of the invention may be carried out by properly converting any of the free acidic groups (e.g. carboxylic, phosphonic or phosphinic) or free amino groups into the corresponding pharmaceutically acceptable salts. In this case too, the operative conditions being employed for the optional salification of the compounds of the invention are all within the ordinary knowledge of the skilled person.

Exemplificative implementation of the above general procedure leading to the compounds of the formula (I) and of the chelate complexes thereof, are schematized herein below.

For instance, compounds of formula (I) may be prepared by using the synthetic procedure schematized in the following Scheme 1

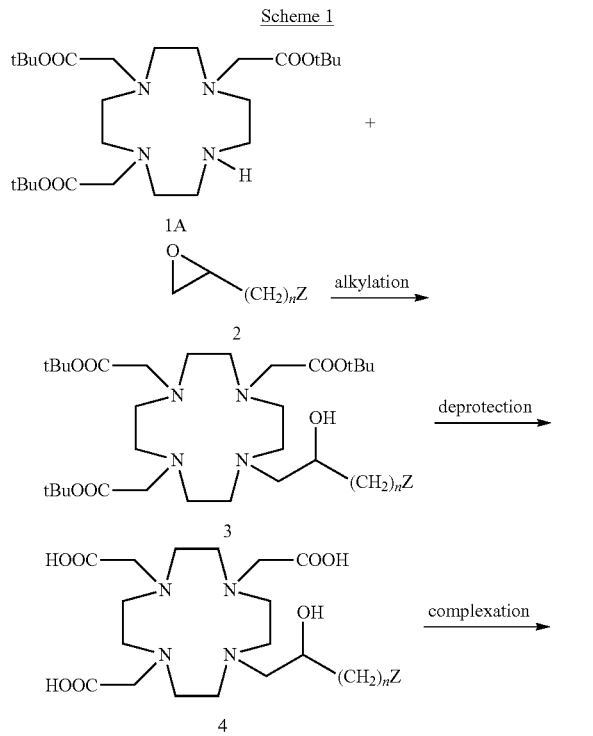

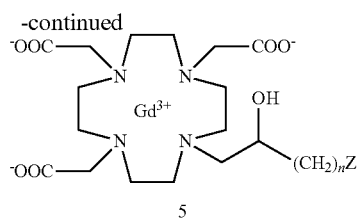

in which a suitable epoxy derivative 2 of the elected Z group is reacted with the protected DO3A substrate 1A to give the protected ligand of formula (I) that, after cleavage of protecting groups is complexed with the gadolinium metal ion to give the desired Gd complex of formula (I).

Compounds of formula (I) where Z is, for example, a suitably substituted heterocyclic ring, e.g. a piperidine derivative as in the compounds formula (III), may alternatively be obtained by using the procedure of the following general Scheme 2, in which S represents a substituent group on the heterocyclic ring

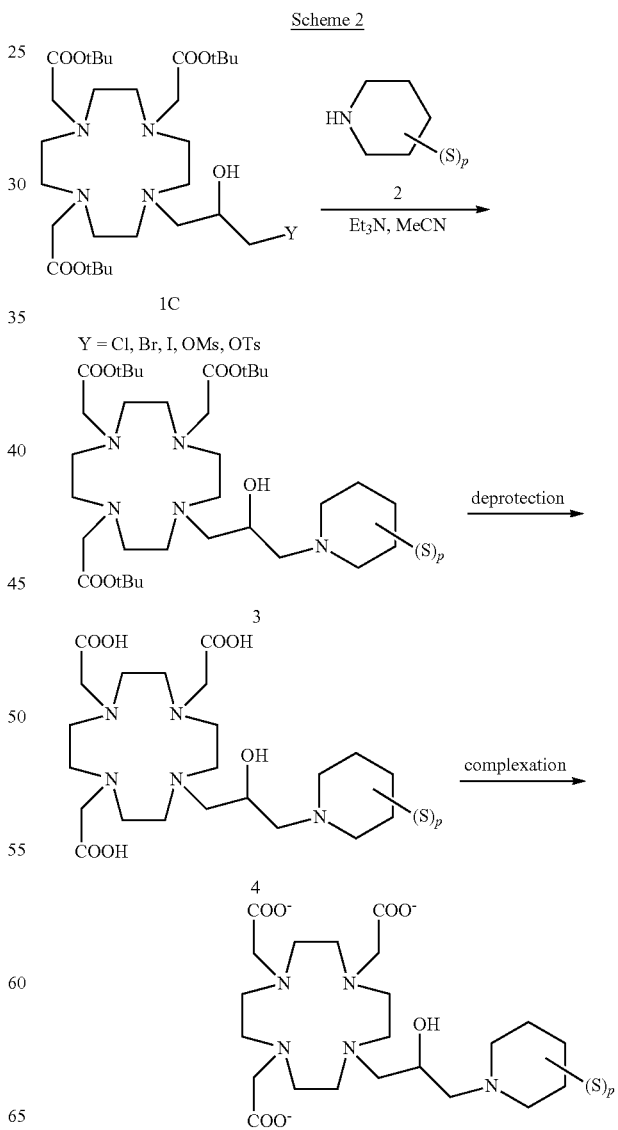

According to this approach, a suitably protected Substrate 1C is first obtained, where Y represents a leaving group for instance selected from bromine, chlorine, iodine and an aryl/alkyl sulfonic ester and, more typically, is a chlorine atom, for instance as described in details in the experimental section. An intermediate 3 is then obtained by coupling the substrate 1C with the suitable piperidine derivative 2 that, after cleavage of protecting groups is complexed with the gadolinium metal ion to give the desired Gd complex of formula (I) as above discussed.

Compounds of formula (I) according to the invention in which Z is an amine derivative of formula —N(R$_2$)(R$_3$) or —NH(R$_4$) as above discussed, may otherwise be prepared by using the procedure schematized in the following general Scheme 3 in which —CH$_2$R$_x$ is a group within R$_2$ or R$_4$ meanings.

According to this approach, a suitably protected Substrate 1B

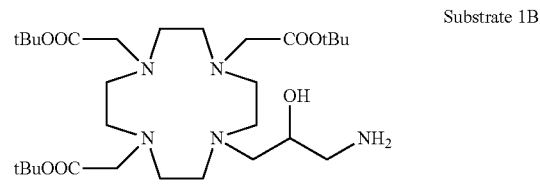

is first obtained, e.g. as described in details in the experimental section, or as disclosed in U.S. Pat. No. 7,208,140, as above said, which is then converted to the desired bis-alkylated derivatives of formula (X) by alkylation.

In particular, as shown in synthetic Scheme 3, the Substrate 1B is first reacted with an aldehyde of formula R$_x$CHO to give a corresponding imino-derivative that, upon reduction, leads to the corresponding protected ligand of formula (IV), or the mono-alkylated intermediate 3 having a R$_2$ group appended to the amine group of the substrate 1B. Then, the obtained intermediate 3 is further reacted, for instance with a suitable phosphite, e.g. tri(tert-butyl)phosphite obtained, for instance, as disclosed in *Tetrahedron Lett.* 2005, 46, 4707-4710, to give the corresponding phosphonate derivative 4 in which the acidic groups are in the protected form. By deprotection of all protected groups the compound of formula (II) is then obtained, which may be complexed with the gadolinium (Gd$^{3+}$) metal ion as above formerly discussed, and isolated as a salt, as provided in better details in the following experimental section.

Compounds of formula (II A) may, alternatively, be prepared by using the following synthetic Scheme 4

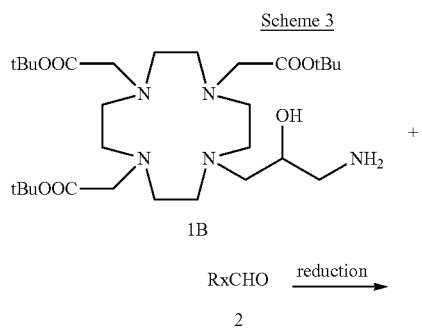

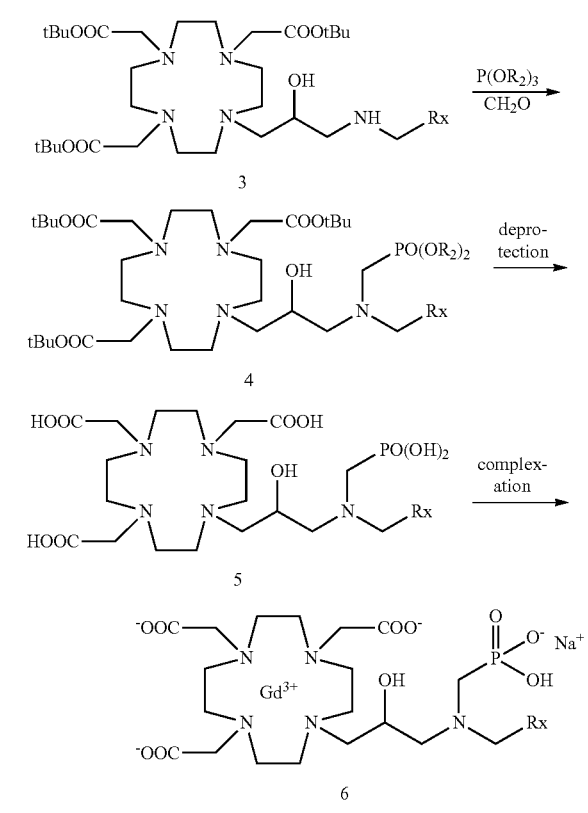

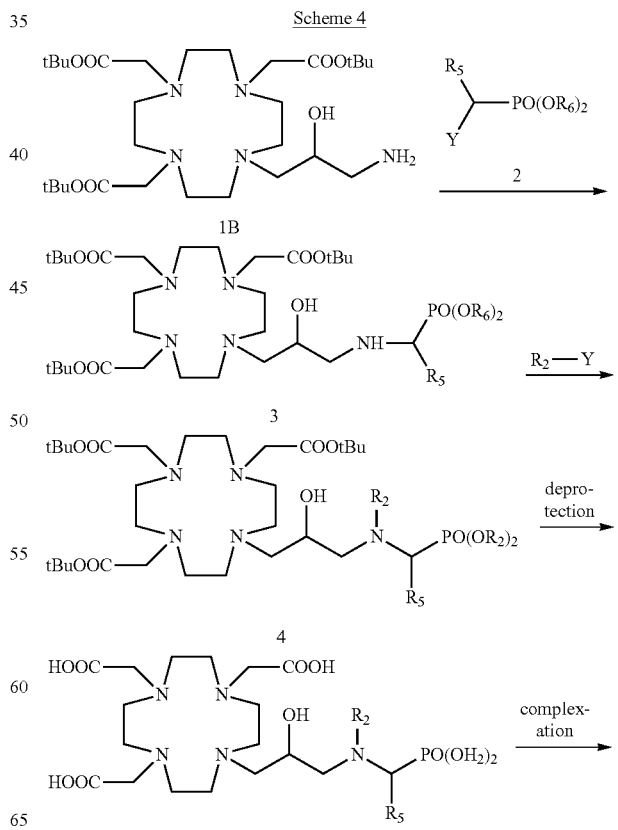

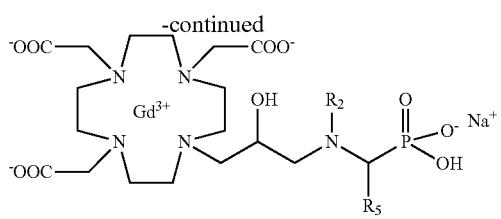

in which the Substrate 1B is first reacted with a suitably protected phosphonate of formula Y—CH(R$_5$)—PO(OR$_6$)$_2$. The obtained compound may then be further reacted with a suitable R$_2$ derivative, e.g. with Y—R$_2$ in which Y is, in both of cases, a suitable leaving group for instance selected from Cl, Br, I, OMs, OTs, as above said.

Preferred compounds according to the invention in which Z is an aminopolyol residue may otherwise be obtained e.g. by using the procedure of the following general Scheme 5

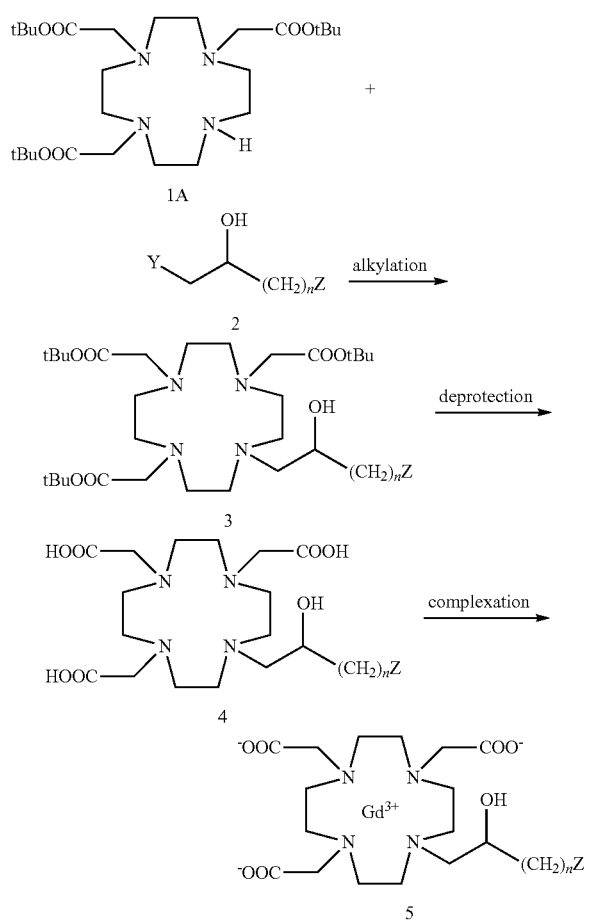

in which a suitable derivative 2 of the elected aminopolyol where Y is a leaving group as said, is reacted with the protected DO3A substrate 1A to give the corresponding protected ligand of formula (I) that, after cleavage of protecting groups is complexed with the gadolinium metal ion to give the desired Gd complex of formula (I).

Specific examples of preparation of preferred compounds of formula (I) according to the invention are moreover provided in the following experimental section, constituting a general reference to the operative conditions being employed in the above processes.

The macrocyclic compounds of formula (I) according to the present invention include an hydroxyl (OH) residue together with an amine derivative Z on a pendant arm of the macrocycle.

Although not willing to be bound by any particular theory, the Applicant considers that the relaxivity of the paramagnetic complexes of the compounds of formula (I) may be significantly improved as a result of the combined effect promoted by these peculiar structural components.

The measured relaxivity is in particular increased with respect to the relaxivity exhibited, under same conditions, by the known MRI contrast agents currently used in the diagnostic daily practice e.g. including Gd-DOTA, marketed as DOTAREM®, and Gd-HPDO3A marketed as ProHance® having analogous macrocyclic chelating ligands and comparable molecular weight. Indeed, as shown in Table A of the experimental section, the paramagnetic complex compounds of the invention show relaxivity $r_{1p}$ values which are about 1.5 and up to 2 times higher than the $r_{1p}$ values displayed by analogous macrocyclic commercial contrast agents (such as above mentioned DOTAREM® and ProHance®), which are however devoid of the combined structural components on the pendant arm of the macrocycle.

In particular, the paramagnetic complex compounds of the formula (I) of the invention display a relaxivity $r_{1p}$ value measured in human plasma, at 37° C. and approx. 1.4 T which is of at least about 5.5, preferably higher than 6, and more preferably, higher than 7 mM$^{-1}$s$^{-1}$.

This unexpected high relaxivity can be further observed, for instance, by comparing the relaxivity displayed by the gadolinium complex of formula

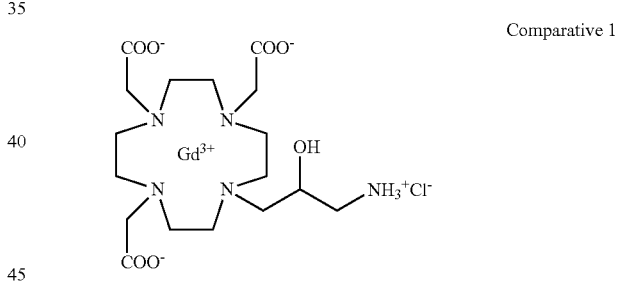

Comparative 1 obtained by deprotection and complexation of substrate 1B, and herein used as

Comparative Compound (Comparative 1), with the relaxivity measured for mono- and bis-alkylated derivative thereof according to the formula (II) of the invention. Indeed, while relaxivity $r_{1p}$ values of 5.3 mM$^{-1}$s$^{-1}$ is obtained for the Comparative 1 in human plasma at 37° C. and 1.41 T, that is in line with the values analogously measured, under the same conditions, for DOTAREM® and ProHance®, respectively of 3.6 and 4.15, a significant increase is observed for the mono-alkylated derivative (e.g. Chelate Complex 2) to a $r_{1p}$ value of 7.5 (in human plasma), that still increase for bis-alkylated derivatives e.g. up to 9.5, for the Chelate Complex 1.

Moreover, the paramagnetic complex compounds of the invention have proven to display a low if not negligible protein binding with human plasma proteins, including, for instance, the HSA.

In particular the paramagnetic complex of formula (I) typically displays a protein binding with the HSA lower than 30%, preferably than 25 and, more preferably than 20%.

These results allow to propose the paramagnetic complex compounds of the invention as Non Specific contrast agents, i.e. as MRI contrast agents suitable for a general use, as the contrast agents of the market like Dotarem®, ProHance® and Magnevist®.

In addition, the Applicant has observed that the presence of a polyol or aminopolyol residue on the hydroxylated pendant arm of the macrocyclic compounds of the invention, beside leading to complex compounds having favorable relaxivity and thermal stability, may also contribute to obtain aqueous solutions of corresponding complex paramagnetic endowed with optimized viscosity.

Advantageously, the high relaxivity displayed by the agents of the invention may further allow reducing their diagnostically effective dose, as compared to current contrast agents. Paramagnetic complexes and, especially, gadolinium complexes of the compounds of formula (I), or the pharmaceutical acceptable salt thereof, thus find advantageous use in the preparation of pharmaceutical formulations intended for a general use in the diagnostic imaging of a human or animal body organ, tissue or region either in vivo or in vitro, ex vivo.

According to a further aspect, the invention relates to the use of the compounds of formula (I) in the form complexes with a paramagnetic metal ion and, especially, gadolinium, or of a pharmaceutical acceptable salt thereof, for the preparation of a pharmaceutical formulation for use in the diagnostic imaging, either in vivo or in vitro, ex vivo, of a human or animal body organ, tissue or region or of a biological sample, including cells, biological fluids and biological tissues originating from a live mammal patient, and preferably, human patient, by use of the MRI technique.

A further aspect of the invention concerns a pharmaceutical composition for diagnostic use comprising a compound of formula (I) in the form of paramagnetic metal complex or of a pharmaceutical salt thereof, in admixture with one or more physiologically acceptable excipients, diluents or solvents. Preferably, the pharmaceutical composition is a contrast-producing composition and, more preferably, a MRI contrast producing composition comprising at least one Gd-complex according to the invention.

In an additional aspect the invention relates to a MRI contrast medium comprising an effective amount of at least one chelated compound according to the invention and, especially, of a gadolinium complex of the formula (I), or of a pharmaceutical acceptable salt thereof, in combination with one or more pharmaceutically acceptable excipients, diluents or solvents.

To this extent, and unless otherwise provided, the term "effective amount" or "effective dose", as used herein, refers to any amount of a paramagnetic chelated complex of the formula (I) according to the invention or pharmaceutical composition thereof, that is sufficient to fulfil its intended diagnostic purpose(s): i.e., for example, to ex vivo visualize a biological element including cells, biological fluids and biological tissues or the in vivo diagnostic imaging of body organs, tissues or regions of a patient.

Unless otherwise indicated, with "individual patient" or "patient" as used herein we refer to a living human or animal patient, and, preferably a human being undergoing MR diagnostic assessment.

Details concerning dosages, dosage forms, modes of administration, pharmaceutically acceptable carriers, excipients, diluents, adjuvants and the like are known in the art.

Interestingly, and as above discussed, suitable dosage of the paramagnetic complexes according to the invention, i.e. allowing to obtain a diagnostically effective visualization of the body organ, tissue or region at least comparable to that obtained in the daily practice with the MRI contrast agents of the market, may include an amount of the paramagnetic complex lower than that currently used with Non-Specific contrast agents of the market.

For instance, satisfactory diagnostic MRI images, providing a physician with adequate diagnostic support, may be obtained with doses of the gadolinium complex compounds identified by the present invention of about 90%, more preferably 80%, and up to 60% of the dose of MRI contrast agent used in the daily practice, which for adult patients commonly is of about 0.1 mmol/kg of patient body weight.

From all the foregoing it can be easily envisaged that the selection of paramagnetic complex compounds of formula (I) identified by the present invention have a wide range of applications as they can be used for intravasal, (for instance intravenous, intraarterial, intracoronaric, intraventricular administration and the like), intrathecal, intraperitoneal, intralymphatic and intracavital administrations. Furthermore, they are suitable for the oral or parenteral administration and, therefore, specifically for the imaging of the gastrointestinal tract.

For instance, for parenteral administration they can be preferably formulated as sterile aqueous solutions or suspensions, whose pH can range from 6.0 to 8.5.

These formulations can be lyophilized and supplied as they are, to be reconstituted before use.

For the gastrointestinal use or for injection in the body cavities, these agents can be formulated as a solution or suspension optionally containing suitable excipients in order, for example, to control viscosity.

For the oral administration they can be formulated according to preparation methods routinely used in the pharmaceutical technique or as coated formulations to gain additional protection against the stomach acidic pH thus preventing, in case of chelated metal ions, their release which may take place particularly at the typical pH values of gastric fluids.

Other excipients, for example including sweeteners and/or flavouring agents, can also be added, according to known techniques of pharmaceutical formulations.

The solutions or suspensions of the compounds of this invention can also be formulated as aerosol to be used in aerosol-bronchography and instillation.

For example, they can be also encapsulated into liposomes or even constitute the liposomes themselves, as set forth above, and thus can be used as uni- or multi-lamellar vesicles.

In a preferred aspect, pharmaceutical compositions according to the invention are properly formulated in isotonic sterile aqueous, optionally buffered, solutions for parenteral administration, and most preferably for intravenous or intra-arterial administration.

More preferably, the said diagnostic composition has a concentration of the paramagnetic complex of the formula (I) of from 0.002 and 1.0 M and is supplied, for instance as a bolus, or as two or more doses separated in time, or as a constant or non-linear flow infusion.

In a further aspect, the invention relates to the use of a pharmaceutical composition including a paramagnetic chelated complex of the formula (I) or pharmaceutical acceptable salt thereof for the diagnostic imaging, both in vitro (ex vivo) and in vivo, of pathological systems, including cells, biological fluids and biological tissues originating from a live mammal patient, and preferably, human patient, as well as of human body organ, regions or tissues, including tumors or cancerous tissues, inflammations, as well as for monitoring the progress and results of therapeutic treatment of the said pathologies.

In an additional aspect, the present invention concerns a method for the in vivo imaging of a body organ, tissue or region by use of the MRI technique, said method comprises enhancing the signal generated by the water protons by use of a paramagnetic chelated complex of the formula (I) according to the invention, or a physiological acceptable salt thereof.

In one embodiment, said method comprises administering to a human or animal patient to be imaged a diagnostically effective amount of a composition of the invention comprising a compound of formula (I) in the form of complex with a paramagnetic metal ion, and, preferably, with the $Gd^{3+}$ metal ion and then subjecting the administered patient to the diagnostic imaging by use of the MRI technique.

According to a particularly preferred embodiment, the above MRI method is instead performed on human or animal bodies suitably pre-administered with a diagnostically effective amount of a composition of the invention as above defined.

More particularly, according to a preferred embodiment the present invention refers to a method for the in vivo imaging a human or animal body organ or tissue by use of the MRI technique that comprises the steps of:

a) submitting a human or animal pre-administered with a composition of the invention comprising a compound of formula (I) in the form of a paramagnetic complex, or of a pharmaceutically acceptable salt thereof, and positioned in a MRI imaging system, to a radiation frequency selected to excite the non-zero proton spin nuclei of the active paramagnetic substrate; and b) recording a MR signal from said excited nuclei.

In yet another aspect the invention provides a method for the in vitro (ex vivo) imaging of biological samples, including cells, biological fluids and biological tissues originating from a live mammal patient, and preferably, human patient, by use of the MRI technique, that comprises contacting an effective amount of a paramagnetic complex compound of formula (I), or of a physiologically acceptable salt thereof, with the biological sample of interest and then obtaining MRI signals from said samples by use of the MRI technique.

Non-limiting examples of preferred compounds of the invention and intermediates for their preparation is reported in the following section, aimed to illustrate the invention in greater detail without limiting its scope.

EXPERIMENTAL PART

Example 1

Preparation of the Substrate 1B

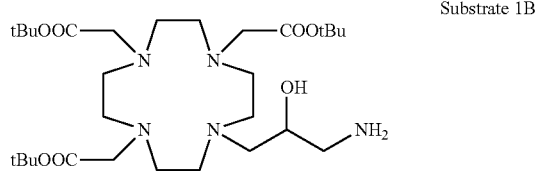

Substrate 1B

This compound was obtained by using the synthetic procedure shown in Scheme 6:

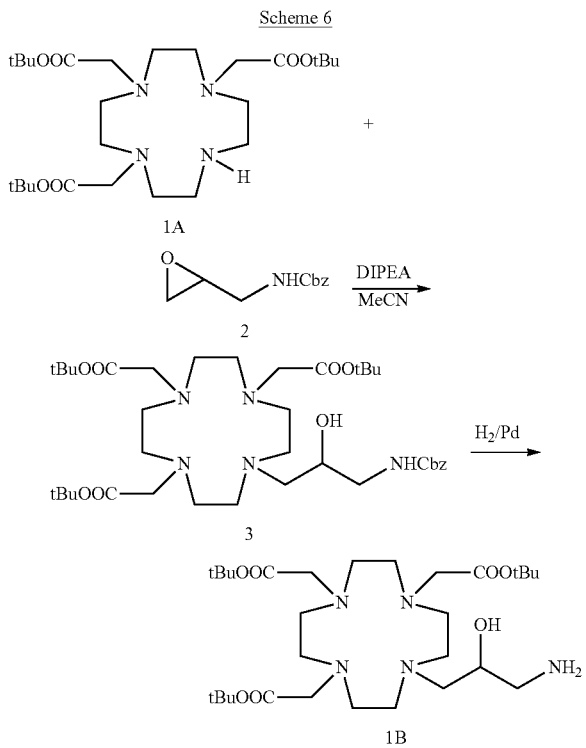

comprising:

a) Preparation of Compound 3

A solution of DO3A tris(t-butyl ester) 1 (*Org. Synth.* 2008, 85, 10) (61.7 g; 0.12 mol), intermediate 2 (obtained as reported in WO2008/126034, page 102) (30.0 g; 0.15 mol) and N,N-diisopropylethylamine (DIPEA) (61.8 g; 0.48 mol) in acetonitrile (300 mL) was stirred at 60° C. for 48 h. The mixture was evaporated to a residue which was dissolved in EtOAc (300 mL). The solution was washed with water (4×50 mL), brine (4×50 mL), filtered and evaporated to a residue that was purified by flash-chromatography (eluent: EtOAc/MeOH=1:1). Fractions containing the desired product were combined and evaporated to a residue which was treated with ethyl ether (200 mL). Intermediate 3 precipitated as a solid which was filtered (48.2 g). Yield 56%.

m. p.=168° C.

1H-NMR, 13C-NMR and mass spectrum are consistent with the expected structure b) Preparation of Substrate Compound 1B Palladium 5% carbon (wet with about 50% water) (2.5 g) was added to a solution of intermediate 3 (60 g; 77 mmol) in MeOH (280 mL). The mixture was stirred and hydrogenated at room temperature and atmospheric pressure for 5 h. The mixture was filtered and evaporated. The residue was dissolved in diethyl ether (400 mL), filtered and evaporated to give compound 1A as a glassy solid (45.2 g). Yield 91%.

1H-NMR, 13C-NMR and mass spectrum are consistent with the expected structure.

Example 2

Preparation of the Substrate 1C

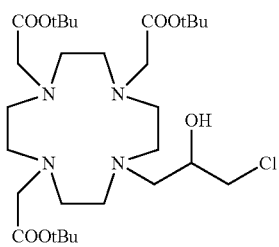

This compound was obtained by using the synthetic procedure shown in Scheme 7:

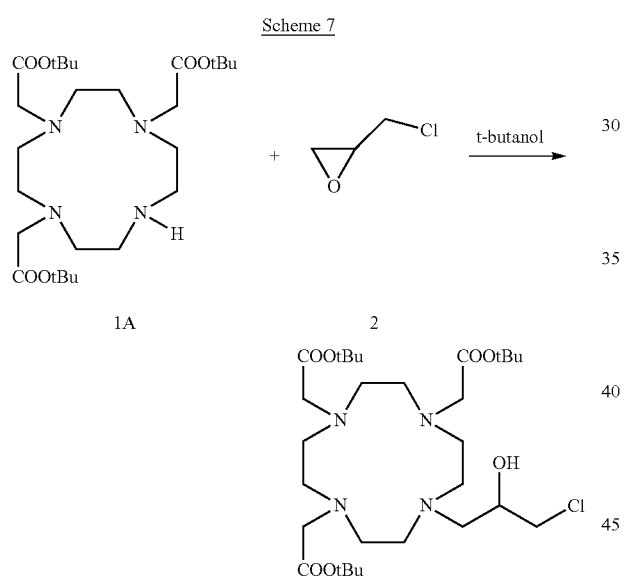

comprising:

a) Preparation of Compound 1C.

Commercially available epichloridrin 2 (10.5 mL; 137 mmol) was dissolved in acetonitrile (300 mL) and the resulting solution was slowly added at room temperature to a solution of DO3A tris-t-butyl ester 1A (*Org. Synth.* 2008, 85, 10) (14.1 g; 27.4 mmol) in acetonitrile (100 mL). The mixture was stirred for 24 h then more epichloridrin 2 (5.2 mL; 68 mmol) was added. After 24 h the mixture was evaporated and the residue purified by chromatography on silica gel (eluent: $CH_2Cl_2$/MeOH=50:1→4:1) to give compound 1C (10.6 g). Yield 64%.

1H-NMR, 13C-NMR and mass spectrum were consistent with the expected structure.

Example 3

Preparation of the Comparative Compound 1

The preparation of the Comparative Compound 1 was obtained as shown in the following Scheme 8:

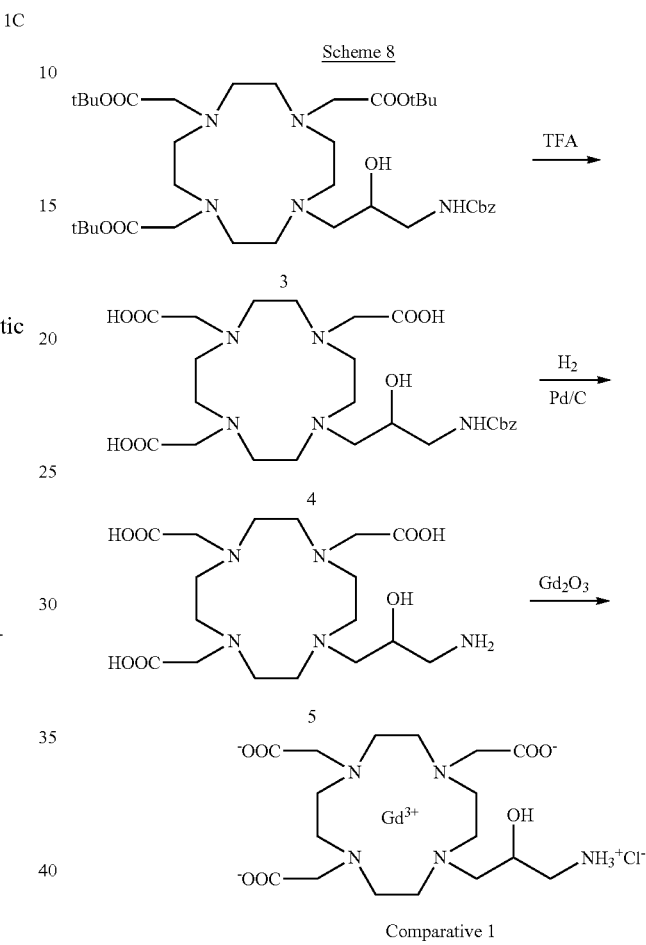

including:

a) Preparation of Intermediate 4

Trifluoroacetic acid (TFA) (130 mL) was added to the compound 3 (obtained as above described in Example 1) (48.0 g; 0.066 mol), cooled with an ice bath. After stirring the mixture for 24 h, ethyl ether (800 mL) was added to the crude reaction leading to the formation of a solid precipitate which was filtered, washed with ethyl ether and dried to give a crude product that was dissolved in water (100 mL) and purified by chromatography on Amberchrome CG161M. By concentration of the pure fractions the desired intermediate 4 was obtained as a glassy residue (20.3 g). Yield 55%.

HPLC 94% (area %)

1H-NMR, 13C-NMR and mass spectrum were consistent with the expected structure.

b) Preparation of Ligand 5

A solution of intermediate 4 (19 g; 0.034 mol) in water (100 mL) and THF (100 mL) was added with 5% palladium on carbon (wet with about 50% water) (4.0 g) and hydrogenated at room pressure and temperature for 3 h. The catalyst was filtered and the solution evaporated to a residue. This latter was then dissolved in water and evaporated twice, then lyophilized to a solid residue. This latter was dissolved in water (60 mL) and the pH of the obtained solution was corrected to 8.0 with resin Duolite 3ASFB (form OH−). The resin was then filtered, washed with water leading to an aqueous solution of ligand 5 that was freeze-dried to a solid residue (10.6 g). Yield 74%.

1H-NMR, 13C-NMR and mass spectrum were consistent with the expected structure c) Complexation Gadolinium oxide (2.72 g; 0.0075 mol) was added to a solution of ligand 5 (6.85 g; 0.016 mol) in water (100 mL) and the obtained mixture was stirred and heated to 90° C. After 1 h, the cloudy solution was filtered on Millipore HA 0.45 μm and the filtrate was brought to a neutral pH with 1 N HCl. The solution was freeze-dried leading to the desired reference Compound 1 as a solid (9.8 g). Yield 98%.

Mass spectrum and elemental analysis were consistent with the expected structure Example 4

Preparation of the Chelate Complex 1

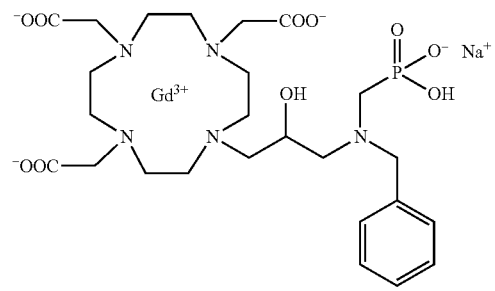

This compound was prepared using the synthetic procedure shown in the following Scheme 9:

Scheme 9

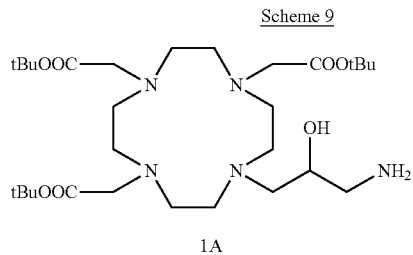

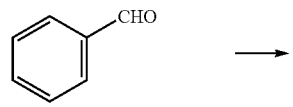

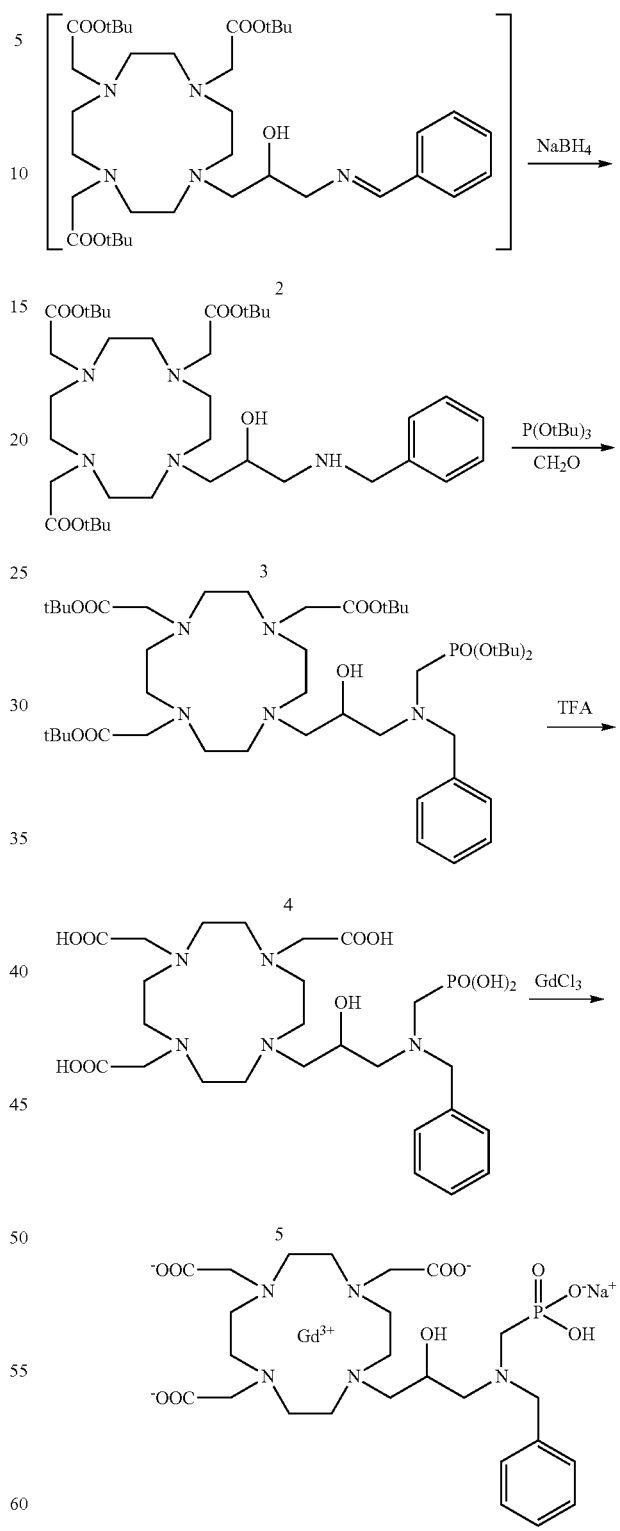

including as main steps:
a) Preparation of Intermediate 3
Benzaldehyde (3.18 g; 0.03 mol) and acetic acid (9 mL) were added to a solution of Substrate A (19.4 g; 0.03 mol) in EtOH (100 mL) and the obtained reaction mixture was stirred for 16 h. The solution was then cooled to 0-5° C. and sodium borohydride (7.5 g; 0.21 mol) was added in small portions. The reaction was maintained at room temperature for 2 h then cooled and diluted with water (200 mL). The organic solvent was evaporated and the pH of the remaining aqueous solution was increased to pH 11 with 2N NaOH (30 mL), then extracted with dichloromethane. After evaporation of the organic solvent the monoalkylated intermediate 3 was obtained as a residue (17 g). Yield 84%.

1H-NMR, 13C-NMR and mass spectrum were consistent with the expected structure.

b) Preparation of Intermediate 4

Paraformaldehyde (1.17 g; 0.039 mol) and tris(t-butyl) phosphite (10.3 g; 0.034 mol) (*Tetrahedron Lett.* 2005, 46, 4707-4710) were added to intermediate compound 3 (23.4 g; 0.034 mol) and the obtained mixture was heated at 70° C. for 3 h. During this time more tris(t-butyl) phosphite was added after 1 h (3 g) and after 2 h (1.5 g). The mixture was evaporated under vacuum to get a residue (35.3 g) that was dissolved in dichloromethane and purified by flash-chromatography (eluent:dichloromethane/MeOH=4:1) to obtain intermediate 4 (23.9 g). Yield 78%.

1H-NMR, 13C-NMR and mass spectrum were consistent with the expected structure.

c) Preparation of Ligand 5

Trifluoroacetic acid (30 mL) was added to a solution of intermediate 4 (16.3 g; 0.018 mol) in dichloromethane (150 mL). The mixture was evaporated, the residue was solubilized in TFA (60 mL), and triisopropylsilane (0.1 mL) was added. The obtained mixture was maintained under stirring for 72 h, then diluted with ethyl ether (450 mL) obtaining the precipitation of a solid that was filtered and purified by chromatography on Amberchrome CG161M column (eluent: gradient of water/MeCN) obtaining the desired ligand 5 (5.3 g). Yield 49%.

Title HPLC 97.3% (area %)

1H-NMR, 13C-NMR and mass spectrum were consistent with the expected structure.

d) Complexation

Gadolinium chloride hexahydrate (0.93 g, 2.5 mmol) was added to a solution of ligand 5 (1.6 g; 2.54 mmol) in water (20 mL) and the pH of the obtained solution was slowly increased to pH 6.5-7 with 2 N NaOH. The obtained solution was stirred at room temperature for 4 h then filtered on Millipore HA 0.45 µm, concentrated and purified by chromatography on Amberchrome CG161M column (eluent: gradient of water/MeCN) obtaining 1.55 g of the desired gadolinium complex. Yield 80%.

Title HPLC 99% (area %)

Mass spectrum and elemental analysis were consistent with the expected structure.

By application of the same synthetic strategy of Scheme 9, the Chelate Complex 17 was analogously obtained by use of cyclohexanecarboxaldehyde (commercially available, e.g. from Sigma-Aldrich).

Example 5

Preparation of the Chelate Complex 2

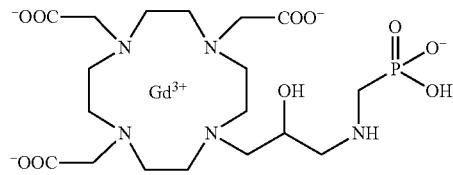

This complex compound was obtained by reduction of the Chelate Complex 1 with $H_2$ and Pd/C. In particular:

Palladium 5% on carbon (420 mg) was added to a solution of gadolinium complex 1 (1.70 g; 2.176 mmol) in water (20 mL) and tetrahydrofuran (20 mL). The hydrogenation reaction was carried out for 2 h (room temperature, 1 atm), then the catalyst was filtered and washed with water. The organic solution was concentrated to remove the organic solvent, filtered on Millipore HA 0.45 µm and lyophilized to give the complex compound 2 as a solid (1.3 g). Yield 84%.

Title HPLC 98% (area %)

Mass spectrum and elemental analysis were consistent with the expected structure.

Example 6

Preparation of the Chelate Complex 3

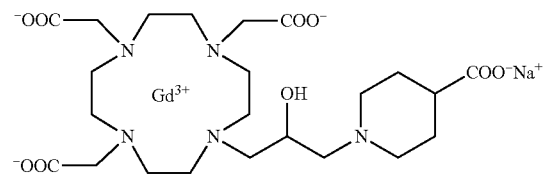

This compound was prepared using the synthetic approach shown in the following Scheme 10:

Scheme 10

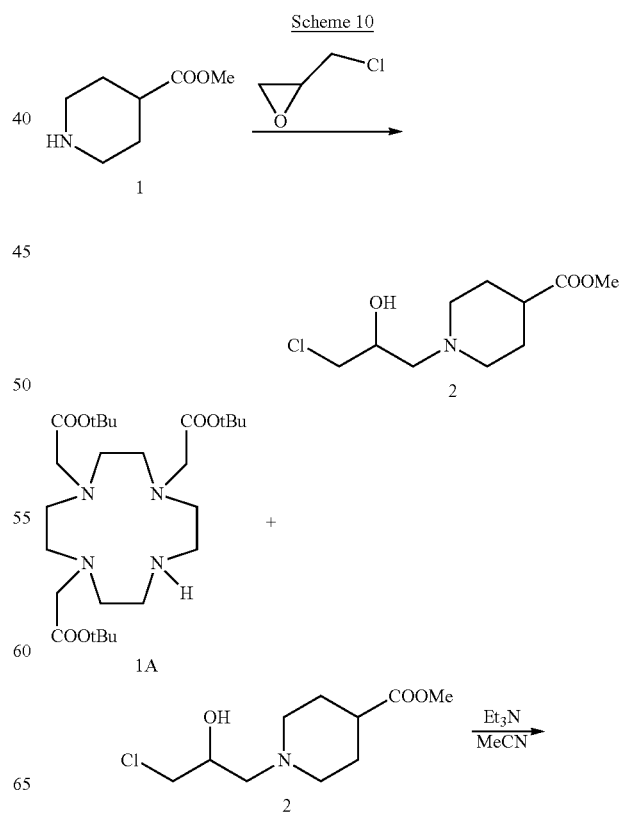

-continued

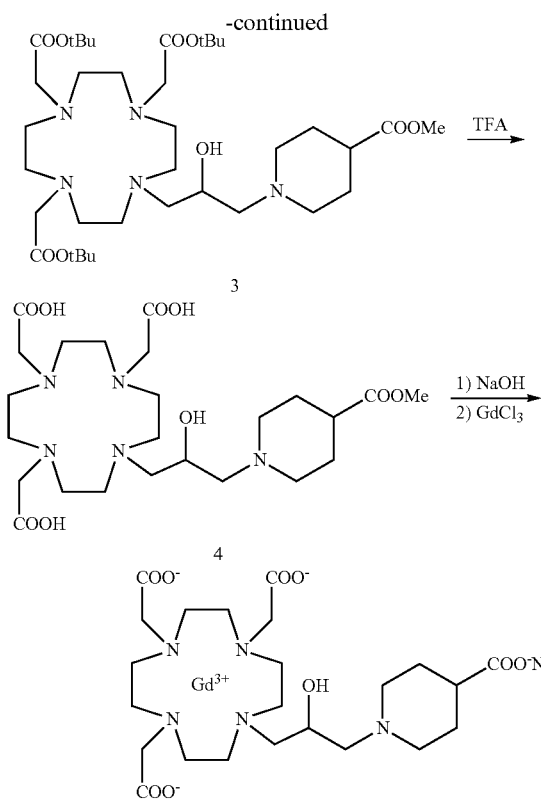

including as main steps:

a) Preparation of the Alkylating Molecule 2

Commercially available epichloridrin (2.57 g; 27.8 mmol) was added to a solution of methyl 4-piperidinecarboxylate 1 (commercially available) (2.65 g; 18.5 mmol) in MeOH (50 mL). The mixture was stirred at room temperature for 18 h then the solvent was evaporated to obtain compound 2 (4.24 g; yield: 87%) that was used without any further purification.

1H-NMR, 13C-NMR and mass spectrum were consistent with the expected structure.

b) Preparation of the Intermediate 3

A solution of DO3A tris-t-butyl ester 1A (*Org. Synth.* 2008, 85, 10) (8.15 g; 15.8 mmol), alkylating agent 2 (4.15 g; 17.6 mmol), Et$_3$N (5 mL) and acetonitrile (40 mL) was heated at 55° C. and stirred for 24 h. The mixture was evaporated and the residue dissolved in EtOAc (80 mL) and washed with water (80 mL) then with brine (4×80 mL). The organic phase was evaporated and the residue purified by chromatography on silica gel (eluent: CH$_2$Cl$_2$/MeOH=100:1→5:1). The fractions containing the pure product were pooled and evaporated to give intermediate 3 (5.2 g). Yield 46%.

1H-NMR, 13C-NMR and mass spectrum were consistent with the expected structure.

c) Preparation of the Intermediate 4

Trifluoroacetic acid (4 mL) was added to a solution of intermediate 3 (5.5 g; 7.7 mmol) in dichloromethane (20 mL). The mixture was stirred for 15 min then evaporated. The residue was dissolved in TFA (30 mL) and triisopropylsilane (0.1 mL) was added. The mixture was maintained under stirring for 40 h then evaporated and the residue purified by chromatography on Amberchrome CG161M column (eluent: gradient of water/MeCN) obtaining the intermediate compound 4 (3.1 g). Yield 74%.

1H-NMR, 13C-NMR and mass spectrum were consistent with the expected structure.

d) Hydrolysis and Complexation

Intermediate 4 (5.6 g; 10.3 mmol) was dissolved in water (100 mL) and 2 M NaOH was added until pH 10. The solution was heated to 45° C. for 8 h keeping the pH at 10. The solution was cooled to room temperature, the pH adjusted to 7 by addition of 1 M HCl and gadolinium chloride hexahydrate (3.86 g; 10.3 mmol) was added. The mixture was stirred at room temperature for 18 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (6.3 g). Yield 86%.

Mass spectrum and elemental analysis were consistent with the expected structure.

Example 7

Preparation of the Chelate Complex 4

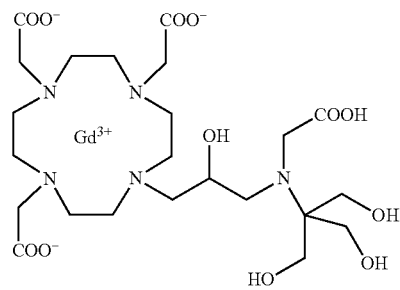

This complex compound was obtained by using the procedure shown in Scheme 11:

Scheme 11

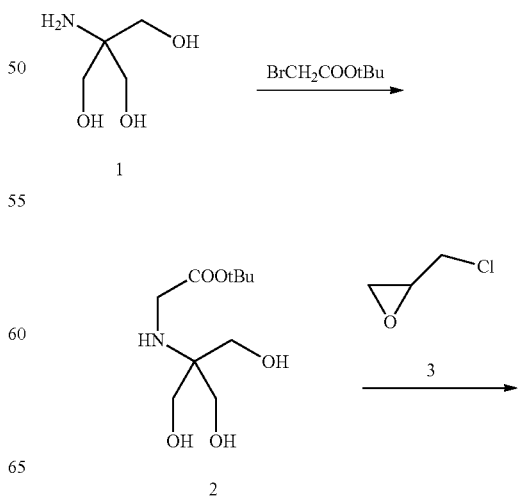

-continued

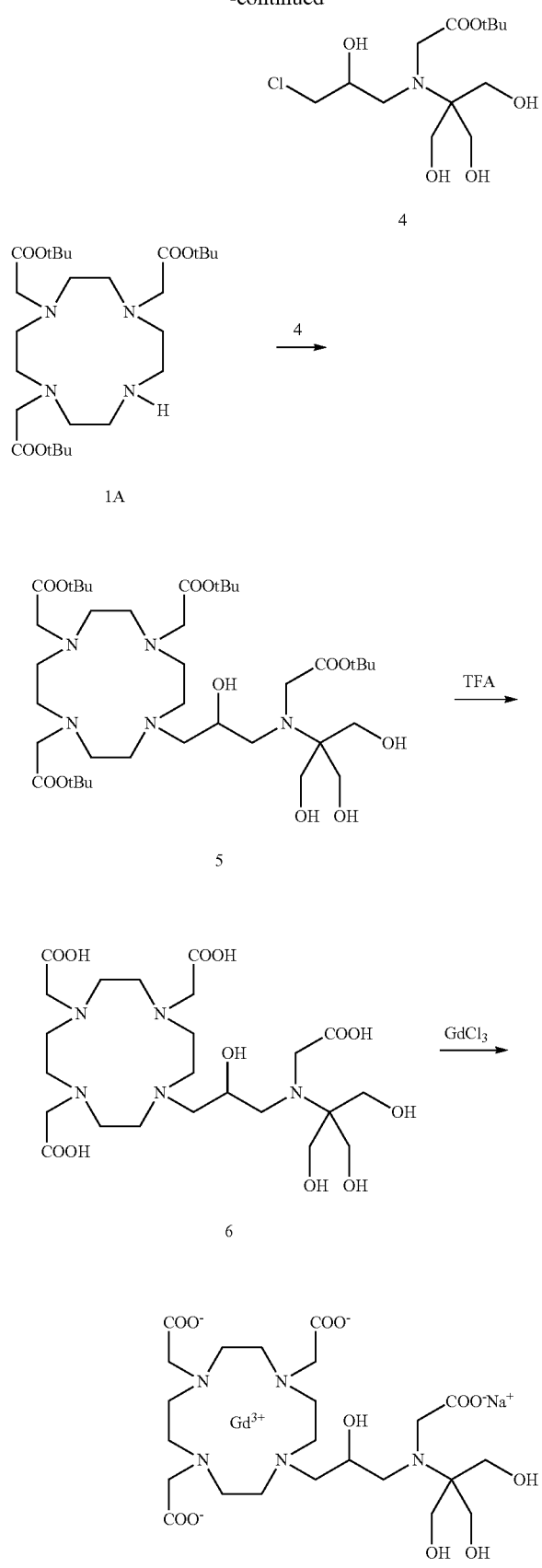

Including:

a) Preparation of 2

A solution of t-butyl bromoacetate (19.3 g; 99 mmol) in acetonitrile (50 mL) was added to a solution of 2-amino-2-(hydroxymethyl)-1,3-propandiol 1 (commercially available) (20 g; 165 mmol) in DMSO (70 mL). The mixture was stirred at room temperature for 72 h. Water (300 mL) was added and the mixture extracted with dichloromethane (4×300 mL). The organic phase was washed with water then all the aqueous phases were pooled and purified by chromatography on Amberlite XE 750 column (eluent: gradient of water/MeOH) obtaining compound 2 as a white solid (13.4 g). Yield 58%.

1H-NMR, 13C-NMR and mass spectrum were consistent with the expected structure.

b) Preparation of 4

Epichlorohydrin 3 (19.8 g; 214 mmol) was added to a solution of compound 2 (10.1 g; 43 mmol) in MeOH (150 mL). The mixture was heated at 55° C. and stirred for 48 h. The mixture was evaporated and the residue purified by chromatography on silica gel (eluent: CH$_2$Cl$_2$/MeOH=14: 1→4:1) to give compound 4 (11.8 g). Yield 84%.

1H-NMR, 13C-NMR and mass spectrum were consistent with the expected structure.

c) Preparation of 5

A mixture of substrate 1A (Org. Synth. 2008, 85, 10) (4 g; 7.8 mmol), compound 4 (4 g; 12.2 mmol), K$_2$CO$_3$ (2.2 g; 15.8 mmol) and acetonitrile (70 mL) was heated at 78° C. and stirred for 20 h. The mixture was filtered, evaporated and the residue purified by chromatography on silica gel (eluent: CH$_2$Cl$_2$/MeOH=50:1→4:1) to give intermediate 5 (3.6 g). Yield 57%.

1H-NMR, 13C-NMR and mass spectrum were consistent with the expected structure.

d) Preparation of 6

Trifluoroacetic acid (4.5 mL) was added to a solution of intermediate 5 (9.4 g; 12.5 mmol) in dichloromethane (30 mL). The mixture was stirred for 30 min then evaporated. The residue was dissolved in TFA (30 mL) and triisopropylsilane (0.1 mL) was added. The obtained mixture was maintained under stirring for 20 h then evaporated and the residue purified by chromatography on Amberlite XE 750 column (eluent: gradient of water/MeCN) obtaining the desired ligand 6 (5.7 g). Yield 78%.

1H-NMR, 13C-NMR and mass spectrum were consistent with the expected structure.

e) Complexation

Ligand 6 (4 g; 6.9 mmol) was dissolved in water (50 mL) and gadolinium chloride hexahydrate (2.55 g; 6.9 mmol) was added. The mixture was stirred at room temperature for 6 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (2.7 g). Yield 52%.

Mass spectrum and elemental analysis were consistent with the expected structure.

By application of the same synthetic strategy of Scheme 11 and employing 2-amino-1,3-propanoldiol (commercially available, e.g. from Sigma-Aldrich) the Chelate Complex 13 was analogously obtained.

Example 8

Preparation of the Chelate Complex 7

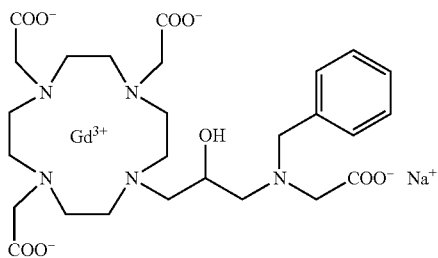

This complex compound was obtained by using the procedure shown in Scheme 12:

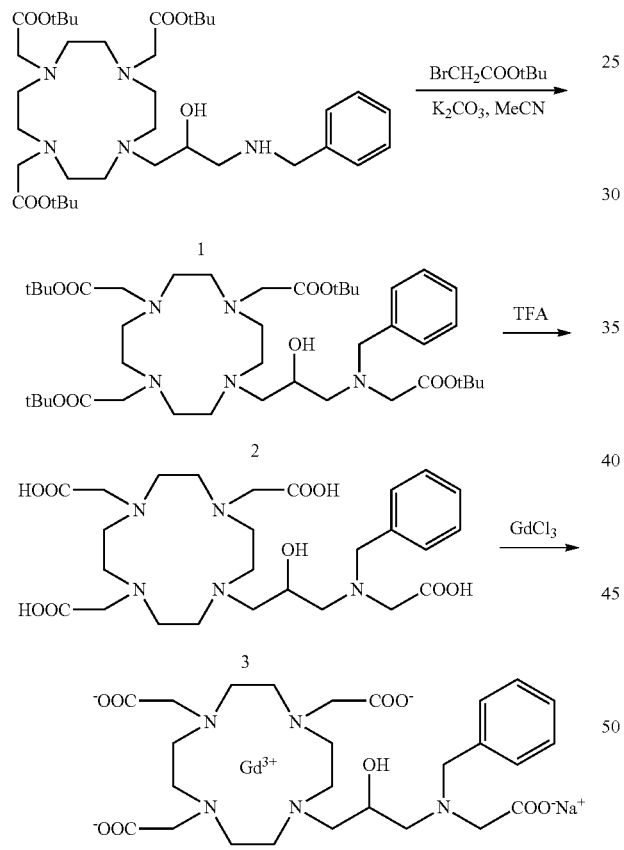

including as main steps:

a) Preparation of 2

A mixture of compound 1 (prepared as reported above in Example 4) (9 g; 13.3 mmol), t-butyl bromoacetate (2.6 g; 13.3 mmol) and $K_2CO_3$ (2.2 g; 16 mmol) in acetonitrile (100 mL) was stirred at room temperature for 20 h then at 40° C. for 4 h. More t-butyl bromoacetate (0.52 g; 2.7 mmol) and $K_2CO_3$ (0.45 g; 3.3 mmol) were added and the mixture was stirred at 40° C. for 3 h then at 55° C. for 2 h. The mixture was filtered and the solution was evaporated to give an oil that was dissolved with $CH_2Cl_2$ (100 mL). The solution was washed with water (3×100 mL), brine (100 mL) and evaporated. The crude oily residue was purified by flash chromatography on silica gel (eluent: $CH_2Cl_2$/MeOH=10:1) to give intermediate 2 as an oil (7.4 g) Yield 70%.

1H-NMR, 13C-NMR and mass spectrum were consistent with the expected structure.

b) Preparation of the Ligand 3

Trifluoroacetic acid (3.6 mL) was added to a solution of intermediate 2 (7.4 g; 9 mmol) in dichloromethane (10 mL) at 0° C. The mixture was then evaporated, the residue was solubilized in TFA (40 mL) and triisopropylsilane (0.1 mL) was added. The mixture was stirred for 24 h at room temperature, then evaporated and the residue purified by chromatography on Amberchrome CG161M column (eluent: gradient of water/EtOH) obtaining the desired chelating ligand 3 (4.14 g). Yield 81%.

1H-NMR, 13C-NMR and mass spectrum were consistent with the expected structure.

c) Complexation

Gadolinium chloride hexahydrate (6.8 g, 18.3 mmol) was added to a stirred solution of chelating ligand 3 (10.4 g; 18.3 mmol) in water (400 mL) and the pH of the mixture was slowly increased to pH 6.5-7 with 1 N NaOH. The obtained solution was stirred at room temperature for 5 h then filtered on Millipore HA 0.45 μm, concentrated and purified by chromatography on Amberchrome CG161M column (eluent: gradient of water/EtOH) obtaining 13 g of the gadolinium complex. Yield 95%.

Title HPLC 99% (area %)

Mass spectrum and elemental analysis were consistent with the expected structure.

Example 9

Preparation of the Chelate Complex 8

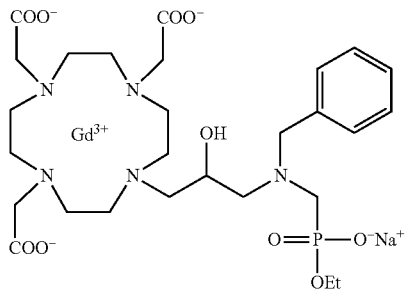

This complex compound was obtained by using the procedure schematized in the following Scheme 13:

Scheme 13

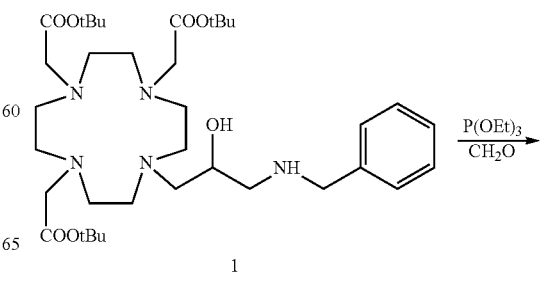

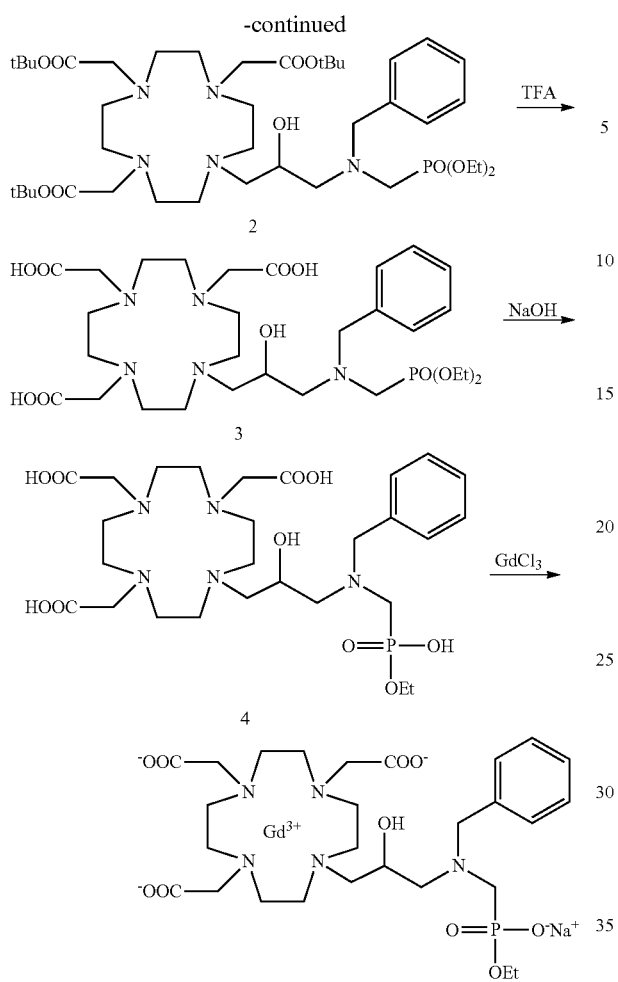

including as main steps:

a) Preparation of Intermediate 2

A mixture of compound 1 (prepared as reported above in Example 4) (10.6 g; 15.6 mmol), paraformaldehyde (0.733 g; 24.4 mmol), triethylphosphite (4.27 g; 25.7 mmol) and acetonitrile (10 mL) was stirred at 70-75° C. for 32 h. The mixture was evaporated and the residue was purified by flash chromatography on silica gel (eluent: $CH_2Cl_2$/MeOH=30:1-4:1) to give intermediate 2 as an orange oil (6.6 g) Yield 51%.

1H-NMR, 13C-NMR and mass spectrum are consistent with the expected structure.

b) Preparation of the Intermediate 3

Trifluoroacetic acid (2.9 mL) was added to a solution of intermediate 2 (6.1 g; 7.6 mmol) in dichloromethane (15 mL) at 0° C. The mixture was then evaporated, the residue was dissolved in TFA (25 mL) and triisopropylsilane (0.1 mL) was added. The mixture was stirred at room temperature for 48 h, then evaporated and the residue purified by chromatography on Amberlite XE750 column (eluent: gradient of water/MeCN) obtaining the intermediate 3 (3.19 g). Yield 63%.

1H-NMR, 13C-NMR and mass spectrum were consistent with the expected structure.

c) Preparation of Ligand 4

Intermediate 3 (3.45 g; 5.2 mmol) was dissolved in water (35 mL) and 1 M NaOH (31.4 mL; 31.4 mmol) was added. The solution was stirred at room temperature for 48 h, acidified with conc. HCl to pH 1.5 and purified by chromatography on Amberlite XE750 column (eluent: gradient of water/MeCN) obtaining the chelating ligand 4 (2.54 g). Yield 77%.

1H-NMR, 13C-NMR and mass spectrum were consistent with the expected structure.

d) Complexation

Gadolinium chloride hexahydrate (1.18 g, 3.2 mmol) was added to a stirred solution of chelating ligand 4 (2 g; 3.2 mmol) in water (40 mL) and the pH of the mixture was slowly increased to pH 6.5-7 with 1 N NaOH. After 2 h the obtained solution is filtered on Millipore HA 0.45 μm, concentrated and then purified by chromatography on Amberlite XE750 column (eluent: gradient of water/MeCN) obtaining 2.49 g of the gadolinium complex. Yield 96%.

Mass spectrum and elemental analysis were consistent with the expected structure.

Example 10

Preparation of Chelate Complex 5

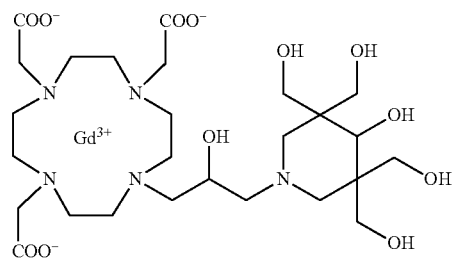

This compound was prepared using the procedure of the following general Scheme 14:

Scheme 14

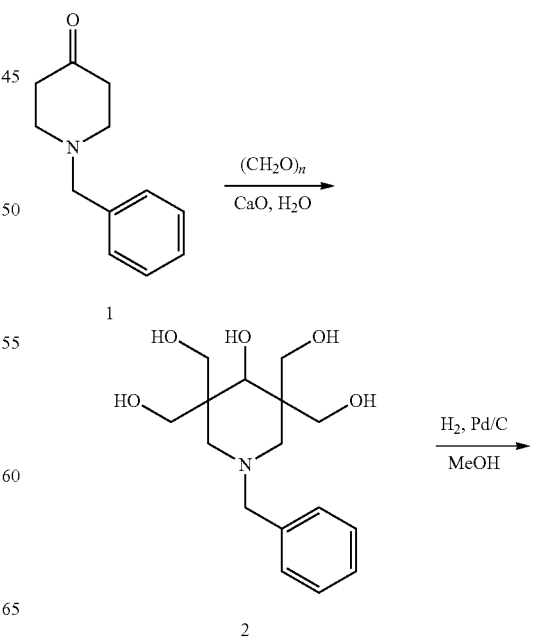

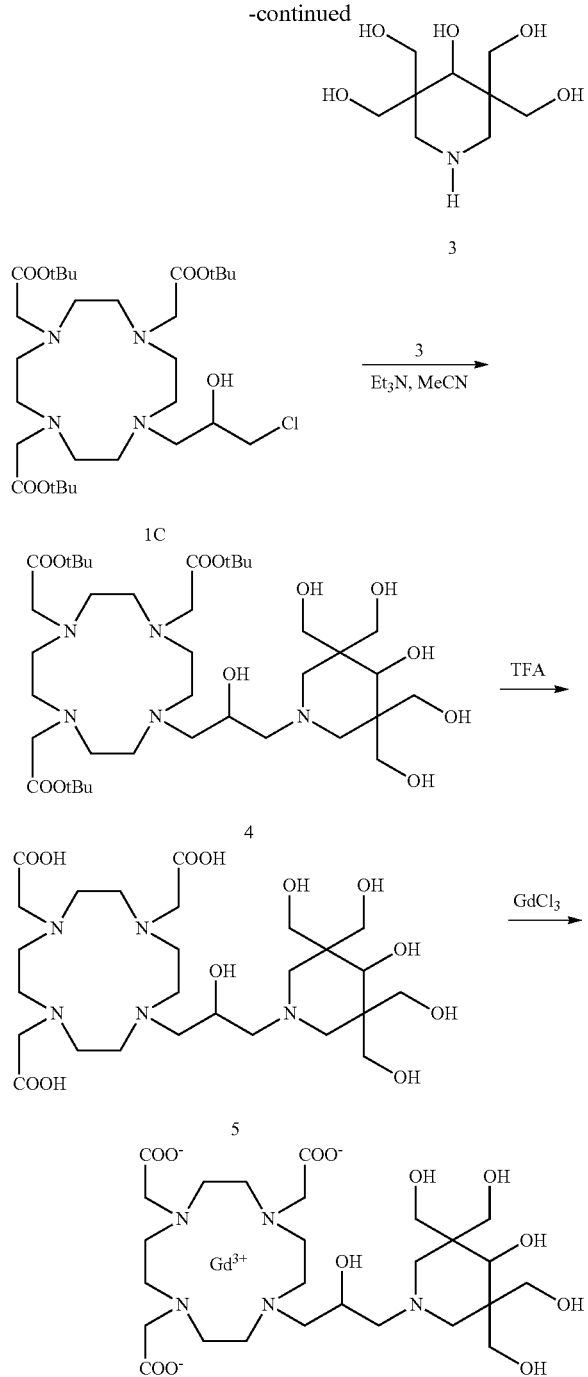

including as main steps a) Preparation of 2

Calcium oxide (3.37 g; 60 mmol) was added in small portions to a mixture of 1-benzyl-4-piperidone 1 (commercially available) (18 g; 95 mmol) and paraformaldehyde (15.7 g; 523 mmol) in water (180 mL). The mixture was stirred at 40° C. for 24 h then evaporated. The residue was purified by chromatography on silica gel (eluent: $CH_2Cl_2$/MeOH=100:1→4:1) to give intermediate 2 as a white sticky solid (4.15 g). Yield 14%.

1H-NMR, 13C-NMR and mass spectrum were consistent with the expected structure.

b) Preparation of the Piperidine Derivative 3

A solution of intermediate 2 (4 g; 12.8 mmol) in methanol (50 mL) was added with 5% palladium on carbon (wet with about 50% water) (2.1 g) and hydrogenated at room pressure and 45° C. for 5 h. The catalyst was filtered and the solution evaporated to give intermediate 3 as a white solid (2.54 g). Yield 89%.

1H-NMR, 13C-NMR and mass spectrum were consistent with the expected structure.

c) Preparation of 4

A solution of substrate 1C (5 g; 8.2 mmol) in acetonitrile (10 mL) obtained as disclosed in Example 2 was added to a mixture of piperidine derivative 3 (2.3 g; 10.4 mmol), $Et_3N$ (2 mL) and acetonitrile (25 mL) at 55° C. After 7 h DMSO (10 mL) was added and the mixture heated at 65° C. for 20 h. The mixture was evaporated and the residue dissolved with $CH_2Cl_2$ (100 mL) and washed with brine (3×100 mL). The organic phase was evaporated to give intermediate 4 as a white solid (3.8 g). Yield 58%.

1H-NMR, 13C-NMR and mass spectrum were consistent with the expected structure.

d) Preparation of Ligand 5

Trifluoroacetic acid (10 mL) was added to a solution of intermediate 4 (4.84 g; 6.1 mmol) in dichloromethane (50 mL). The mixture stirred for 30 min then was evaporated. The residue was dissolved in TFA (20 mL) and triisopropylsilane (0.1 mL) was added. The obtained mixture was maintained under stirring for 24 h then evaporated and the residue purified by chromatography on Amberlite XE 750 column (eluent: gradient of water/MeCN) obtaining the desired ligand 5 (2.7 g). Yield 71%.

1H-NMR, 13C-NMR and mass spectrum were consistent with the expected structure.

e) Complexation

Ligand 5 (2.2 g; 3.5 mmol) was dissolved in water (20 mL) and gadolinium chloride hexahydrate (1.31 g; 3.5 mmol) was added. The mixture was stirred at room temperature for 6 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (1.54 g). Yield 56%.

Mass spectrum and elemental analysis were consistent with the expected structure.

Example 11

Preparation of the Chelate Complex 18

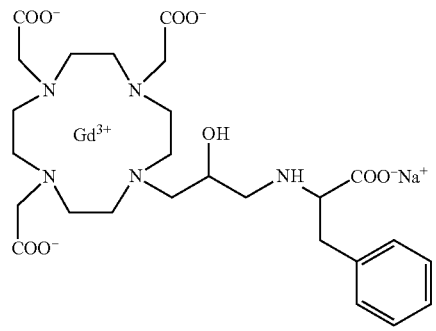

This compound was prepared using the procedure of the following general Scheme 15:

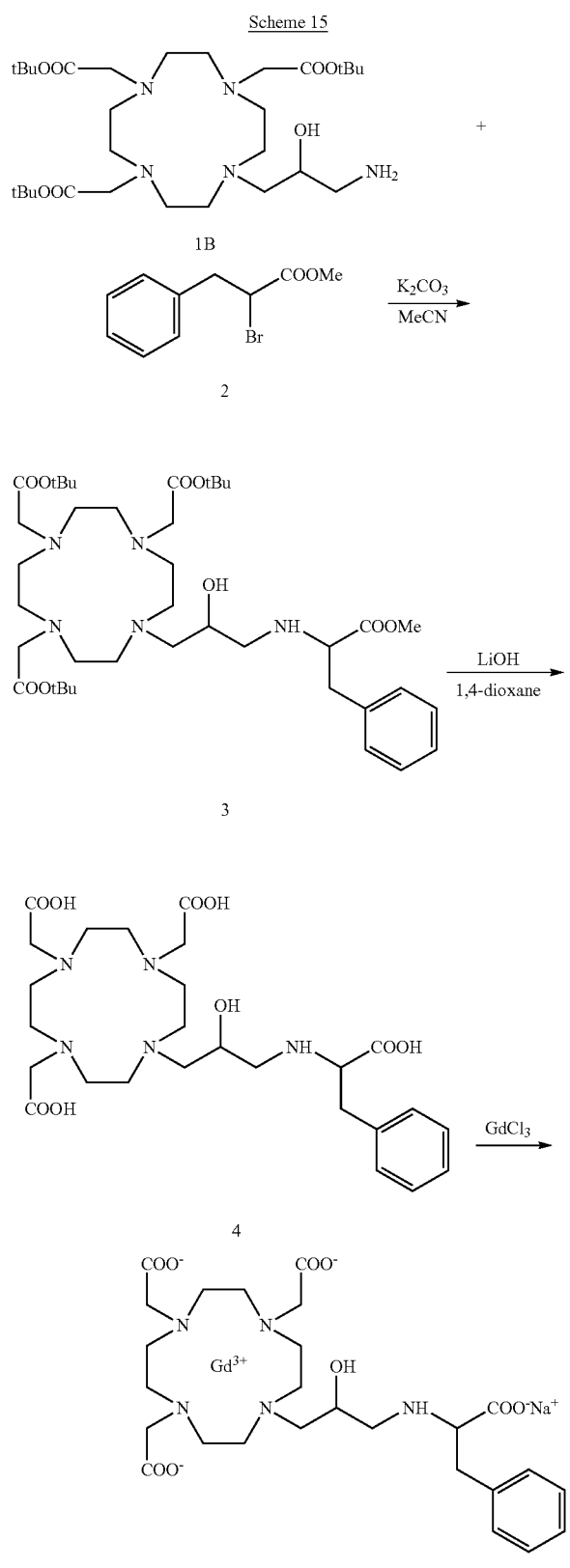

including the following main steps a) Preparation of Intermediate 3

Methyl 2-bromo-3-phenylpropanoate (prepared as reported in *Eur. J. Org. Chem.* 2011, 1300) (2.43 g; 10 mmol) was added to a mixture of Substrate 1B (17.6 g; 30 mmol) and $K_2CO_3$ (4.1 g; 30 mmol) in MeCN (100 mL). The reaction was stirred at room temperature for 72 h then filtered and evaporated. The residue was dissolved with $CH_2Cl_2$ (200 mL). The solution was washed with water (3×100 mL), brine (100 mL) and evaporated. The residue was purified by flash chromatography on silica gel (eluent: $CH_2Cl_2$/MeOH) to give intermediate 1 (4.3 g) Yield 57%.

1H-NMR, 13C-NMR and mass spectrum are consistent with the expected structure.

b) Preparation of Ligand 4

A 2 M LiOH (53 mL; 106 mmol) aqueous solution was added to a solution of intermediate 3 (4 g; 5.3 mmol) in 1,4-dioxane (50 mL). The mixture was stirred for 72 h then acidified to pH 6 by slow addition of 37% HCl. The solution was evaporated, the solid residue was purified by chromatography on Amberlite XAD 16.00 column (eluent:gradient of water/MeCN) obtaining the chelating ligand 2 (2.7 g). Yield 90%.

1H-NMR, 13C-NMR and mass spectrum were consistent with the expected structure.

c) Complexation

Gadolinium chloride hexahydrate (1.64 g, 4.4 mmol) was added to a solution of chelating ligand 2 (2.5 g; 4.4 mmol) in water (100 mL) and the pH of the mixture was slowly increased to pH 6.5-7 with 1 N NaOH. The obtained solution was stirred at room temperature then filtered on Millipore HA 0.45 μm, concentrated and purified by chromatography on Amberchrome CG161M column (eluent: gradient of water/EtOH) obtaining 3.1 g of the gadolinium complex. Yield 94%.

Mass spectrum and elemental analysis were consistent with the expected structure.

Applying the same synthetic strategy and employing methyl 2-bromo-3-cyclohexylpropanoate (prepared as reported in *Eur. J. Org. Chem.* 2011, 1300) the Chelate Complex 9 was prepared.

Applying the same synthetic strategy and employing 2-phenyl-1-(methanesulfonyloxy) ethylphosphonic acid diethyl ester (prepared as reported in Synthesis 1996, 507) the Chelate Complex 6 was prepared.

Example 12

Preparation of the Chelate Complex 12

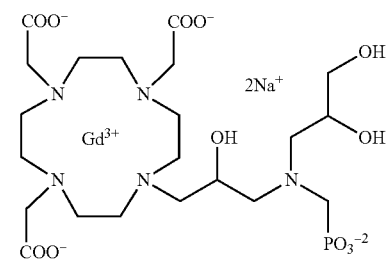

This compound was prepared using the procedure of the following general Scheme 16:

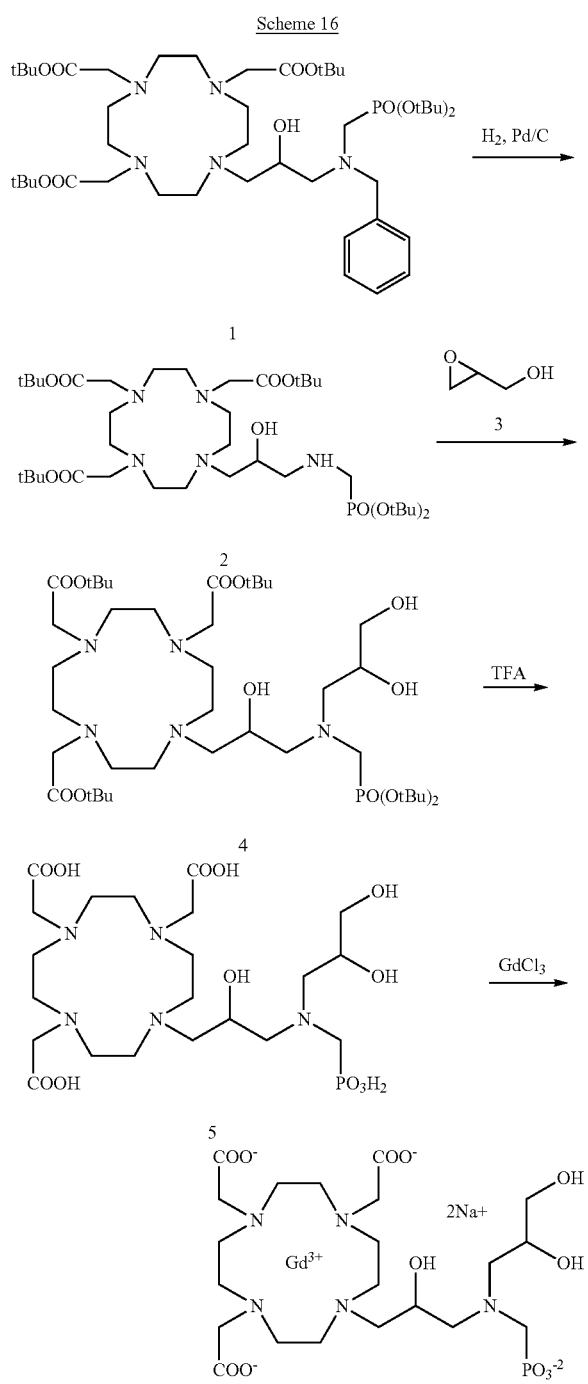

including:

a) Preparation of 2

Palladium 5% carbon (wet with about 50% water) (4 g) was added to a solution of intermediate 1 (prepared as reported in Scheme 8) (20 g; 22.6 mmol) in MeOH (250 mL). The mixture was stirred and hydrogenated at room temperature and atmospheric pressure for 8 h. The mixture was filtered and evaporated to give intermediate 2 (17.6 g). Yield 98%.

1H-NMR, 13C-NMR and mass spectrum were consistent with the expected structure.

b) Preparation of 4

2,3-Epoxy-1-propanol 3 (commercially available) (1.5 g; 20.2 mmol) was added to a solution of intermediate 2 (15 g; 18.9 mmol) in acetonitrile (150 mL). The solution was refluxed for 16 h then evaporated. The residue was purified by flash chromatography on silica gel (eluent: gradient of EtOAc/MeOH) to give intermediate 4 (9.52 g). Yield 58%.

1H-NMR, 13C-NMR and mass spectrum were consistent with the expected structure.

c) Preparation of the Chelating Ligand 5

Trifluoroacetic acid (10 mL) was added to a solution of intermediate 4 (8.7 g; 10 mmol) in dichloromethane (50 mL) at 0° C. The mixture was stirred for 8 h then evaporated and the residue was dissolved in TFA (50 mL). The mixture was stirred at room temperature for 16 h, then evaporated. The residue was purified by chromatography on Amberchrome CG161M column (eluent: gradient of water/MeCN) obtaining the chelating ligand 5 (5.3 g). Yield 90%.

1H-NMR, 13C-NMR and mass spectrum were consistent with the expected structure.

d) Complexation

Gadolinium chloride hexahydrate (3.16 g, 8.5 mmol) was added to a solution of chelating ligand 5 (5 g; 8.5 mmol) in water (100 mL) and the pH of the mixture was slowly increased to pH 6.5-7 with 1 N NaOH. The obtained solution was filtered on Millipore HA 0.45 µm, concentrated and then purified by chromatography on Amberchrome CG161M column (eluent: gradient of water/MeCN) obtaining 6.48 g of the corresponding gadolinium complex. Yield 97%.

Mass spectrum and elemental analysis were consistent with the expected structure.

Example 13

Preparation of the Chelate Complex 19

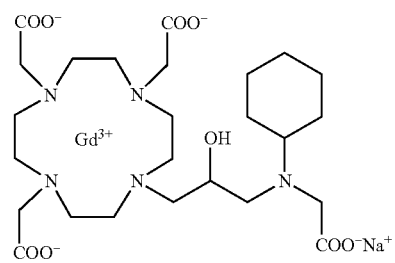

This compound was prepared using the procedure of the following general Scheme 17:

Scheme 17

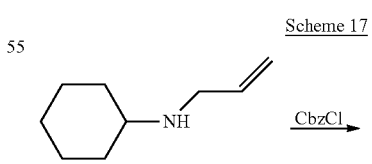

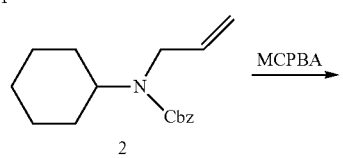

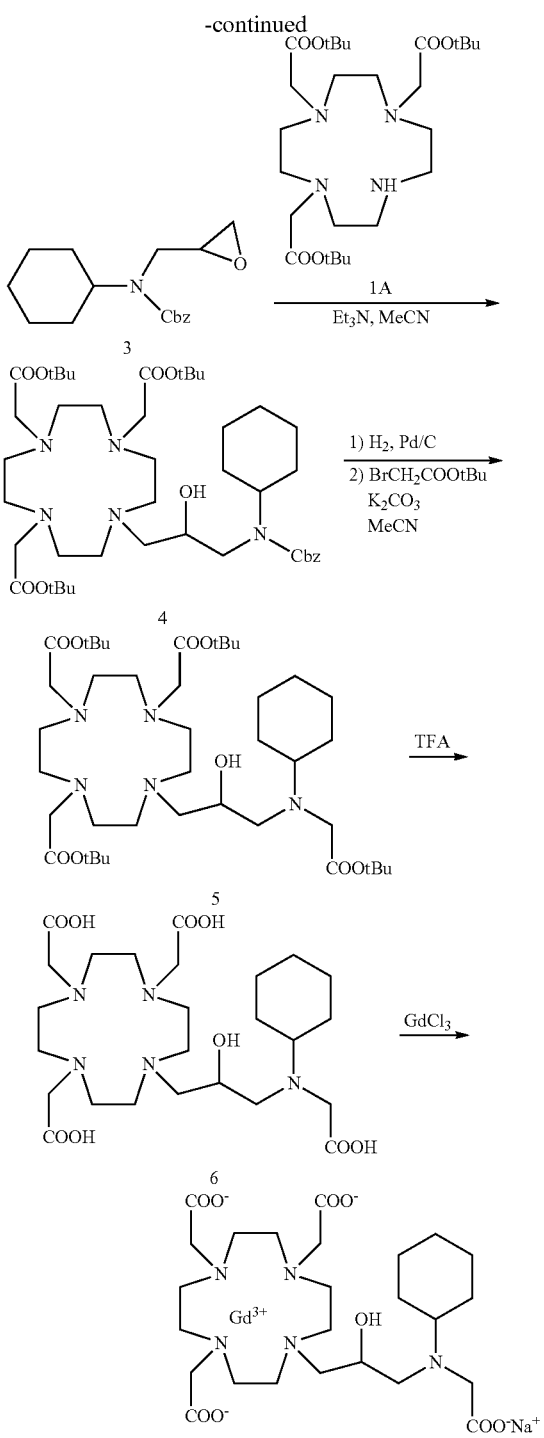

including:

a) Preparation of Intermediate 2

Benzyl chloroformate (95%; 19.75 g; 110 mmol) was added in 1 h to a mixture of allylcyclohexylamine 1 (commercially available) (13.9 g; 100 mmol), $K_2CO_3$ (27.6 g; 200 mmol), water (150 mL) and EtOAc (200 mL) at 0° C. After stirring for 6 h, the organic phase was separated and washed with 1 N HCl (2×100 mL), water (100 mL) and brine (100 mL). The organic phase was dried ($Na_2SO_4$) and evaporated to give intermediate 2 (26.2 g). Yield 96%.

1H-NMR, 13C-NMR and mass spectrum were consistent with the expected structure.

b) Preparation of Intermediate 3

A solution of 3-chloroperbenzoic acid (MCPBA) (75%; 23 g; 100 mmol) in dichloromethane (100 mL) was added dropwise to a solution of intermediate 2 (13.7 g; 50 mmol) in dichloromethane (100 mL). The solution was stirred at room temperature for 16 h. The mixture was filtered, washed with 10% aq. $Na_2SO_3$ (2×100 mL), 5% aq. $NaHCO_3$ (4×100 mL), $H_2O$ (100 mL) and brine (100 mL). The organic phase was separated, evaporated and the residue purified by chromatography on silica gel (eluent: gradient of n-heptane/EtOAc) to obtain intermediate 3 (13.0 g). Yield 90%.

1H-NMR, 13C-NMR and mass spectrum were consistent with the expected structure.

c) Preparation of Intermediate 4

A solution of epoxide 3 (10 g, 34.6 mmol), DO3A tri-t-butylester 1A (*Org. Synth.* 2008, 85, 10) (15.44 g; 30 mmol) and $Et_3N$ (3.54 g, 35 mmol) in MeCN (200 mL) was heated at 60° C. and stirred for 24 h. The reaction mixture was evaporated and the residue was purified by flash chromatography on silica gel (eluent: gradient of $CH_2Cl_2$/MeOH) to give compound 4 (16.1 g) Yield 67%.

1H-NMR, 13C-NMR and mass spectrum were consistent with the expected structure.

d) Preparation of Intermediate 5

Palladium 5% carbon (wet with about 50% water) (3 g) was added to a solution of intermediate 4 (15 g; 18.7 mmol) in MeOH (200 mL). The mixture was stirred and hydrogenated at room temperature and atmospheric pressure for 16 h. The mixture was filtered and evaporated to give a residue that was dissolved in acetonitrile (200 mL) then t-butyl bromoacetate (4.38 g; 22.4 mmol) and $K_2CO_3$ (6.9 g; 50 mmol) were added. The mixture was stirred for 24 h at room temperature then filtered and evaporated. The residue was dissolved in EtOAc (100 mL) and the solution washed with $H_2O$ (2×100 mL) and brine (100 mL). The organic phase was evaporated and the residue purified by column chromatography on silica gel (eluent: gradient of $CH_2Cl_2$/MeOH) to give intermediate 5 (8.06 g). Yield 55%.

1H-NMR, 13C-NMR and mass spectrum were consistent with the expected structure.

e) Preparation of the Chelating Ligand 6

Trifluoroacetic acid (10 mL) was added to a solution of intermediate 5 (7.84 g; 10 mmol) in dichloromethane (50 mL) at 0° C. The mixture was stirred for 8 h then evaporated and the residue was dissolved in TFA (50 mL). The mixture was stirred at room temperature for 24 h, then evaporated. The residue was purified by chromatography on Amberchrome CG161M column (eluent: gradient of water/MeCN) obtaining the chelating ligand 6 (5.2 g). Yield 93%.

1H-NMR, 13C-NMR and mass spectrum were consistent with the expected structure.

f) Complexation

Gadolinium chloride hexahydrate (2.97 g, 8 mmol) was added to a solution of chelating ligand 5 (4.5 g; 8 mmol) in water (80 mL) and the pH of the mixture was slowly increased to pH 6.5-7 with 1 N NaOH. The obtained solution was filtered on Millipore HA 0.45 μm, concentrated and then purified by chromatography on Amberchrome CG161M column (eluent: gradient of water/MeCN) obtaining 5.65 g of the corresponding gadolinium complex. Yield 96%.

Mass spectrum and elemental analysis were consistent with the expected structure.

Using the same synthetic strategy and employing the triflate of hydroxymethylphosphonate di-t-butyl ester (synthesized as reported in US2014/0086846, page 33) the Chelate Complex 15 was prepared.

Example 14

Preparation of the Chelate Complex 10

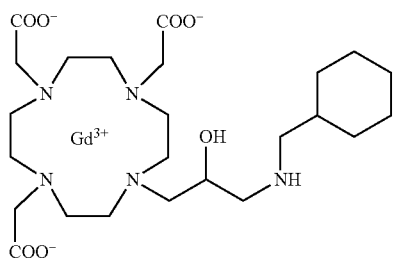

This compound was prepared using the procedure of the following general Scheme 18:

Scheme 18

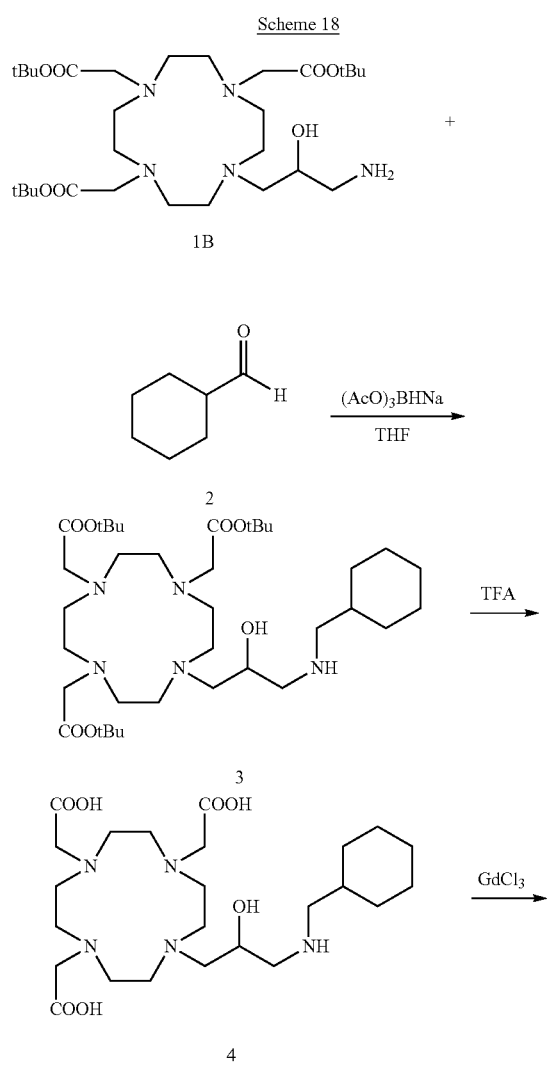

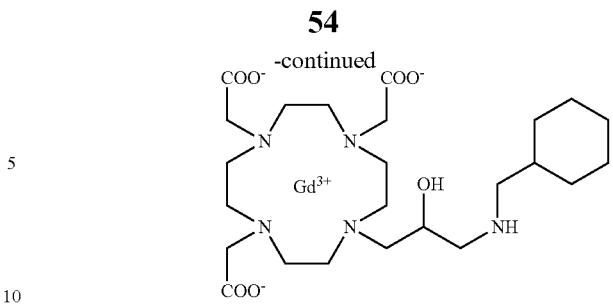

including:

a) Preparation of Intermediate 3

Sodium triacetoxyborohydride (4.77 g; 22.5 mmol) was added to a solution of Substrate 1B (9.7 g; 15 mmol), cyclohexanecarboxaldehyde (1.68 g; 15 mmol) and AcOH (1.8 g; 30 mmol) in THF (80 mL). The reaction mixture was stirred for 24 h then diluted with water (100 mL). The organic solvent was evaporated and the pH of the remaining aqueous solution was increased to pH 11 with 2N NaOH then extracted with dichloromethane. After evaporation of the organic solvent the intermediate 3 was obtained as a residue (8.2 g). Yield 80%.

1H-NMR, 13C-NMR and mass spectrum were consistent with the expected structure.

b) Preparation of the Chelating Ligand 4

Trifluoroacetic acid (15 mL) was added to a solution of intermediate 3 (8 g; 11.7 mmol) in dichloromethane (50 mL) at 0° C. The mixture was stirred for 8 h then evaporated and the residue was dissolved in TFA (50 mL). The mixture was stirred at room temperature for 24 h, then evaporated. The residue was purified by chromatography on Amberchrome CG161M column (eluent: gradient of water/MeCN) obtaining the chelating ligand 4 (5.5 g).

Yield 91%.

1H-NMR, 13C-NMR and mass spectrum were consistent with the expected structure.

c) Complexation

Gadolinium chloride hexahydrate (3.6 g, 9.7 mmol) was added to a solution of chelating ligand 4 (5 g; 9.7 mmol) in water (100 mL) and the pH of the mixture was slowly increased to pH 6.5-7 with 1 N NaOH. The obtained solution was filtered on Millipore HA 0.45 µm, concentrated and then purified by chromatography on Amberchrome CG161M column (eluent: gradient of water/MeCN) obtaining 5.98 g of the corresponding gadolinium complex. Yield 92%.

Mass spectrum and elemental analysis were consistent with the expected structure.

Example 15

Preparation of the Chelate Complex 13

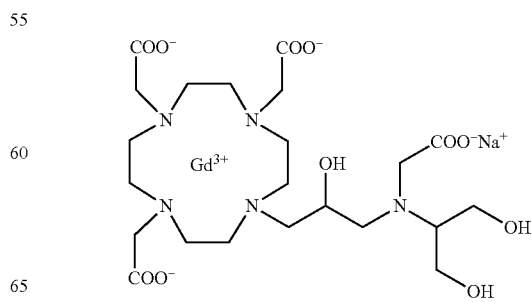

This complex compound was obtained by using the procedure shown in Scheme 19:

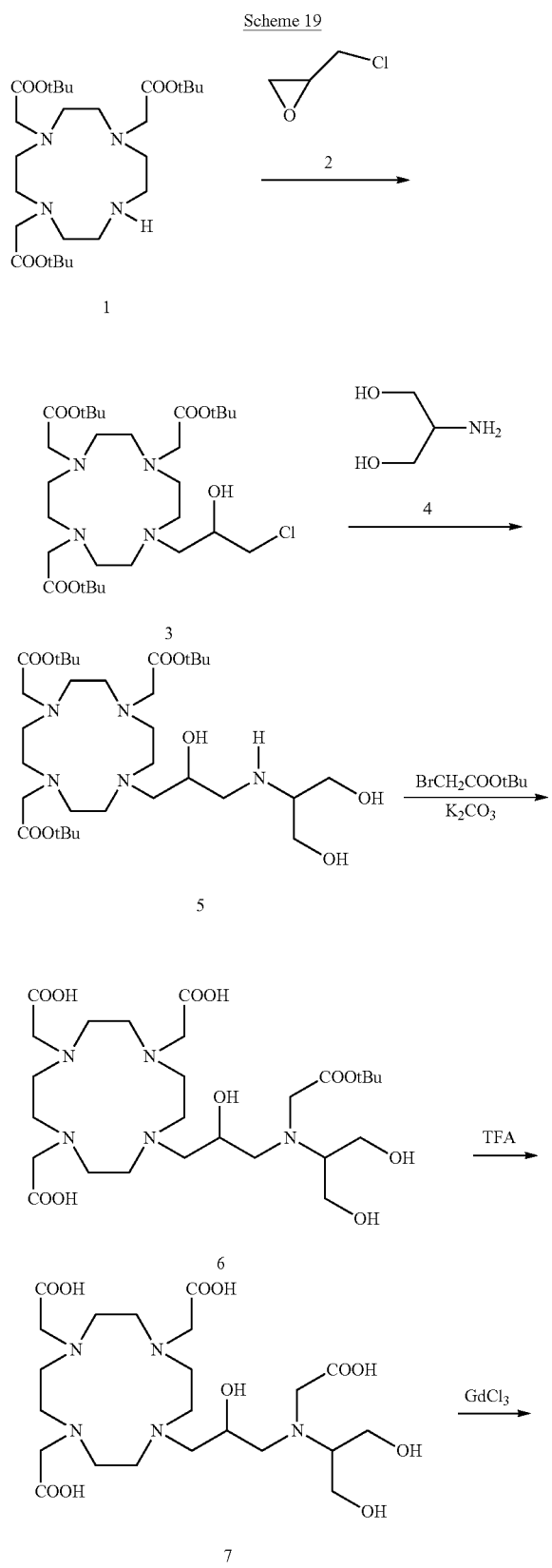

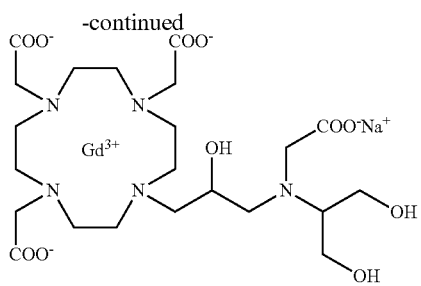

including:

a) Preparation of 3

Epichlorohydrin 2 (10.5 mL; 137 mmol) was dissolved in acetonitrile (300 mL) and the resulting solution was slowly added at room temperature to a solution of DO3A tris-t-butyl ester 1A (*Org. Synth.* 2008, 85, 10) (14.1 g; 27.4 mmol) in acetonitrile (100 mL). The mixture was stirred for 24 h then more epichloridrin 5 (5.2 mL; 68 mmol) was added. After 24 h the mixture was evaporated and the residue purified by chromatography on silica gel (eluent: $CH_2Cl_2/MeOH=50:1\rightarrow4:1$) to give intermediate 3 (10.6 g). Yield 64%.

1H-NMR, 13C-NMR and mass spectrum were consistent with the expected structure.

b) Preparation of 5

A solution of serinol 4 (10.8 g; 118 mmol) in DMSO (30 mL) was added to a solution of compound 3 (9 g; 14.8 mmol) in acetonitrile (100 mL). The mixture was heated at 75° C. for 72 h then the solvent was evaporated. The residue was dissolved in dichloromethane (100 mL) and the solution washed with water (4×100 mL) then brine (3×100 mL). The organic phase was evaporated and the residue purified by flash chromatography on silica gel (eluent: $CH_2Cl_2/MeOH=200:1\rightarrow4:1$) to give compound 5 (6.6 g). Yield 67%.

1H-NMR, 13C-NMR and mass spectrum were consistent with the expected structure.

c) Preparation of 6

A mixture of compound 5 (5.21 g; 8 mmol), t-butyl bromoacetate (1.85 g; 9.5 mmol), $K_2CO_3$ (2.2 g; 15.8 mmol) and acetonitrile (100 mL) was stirred at 45° C. for 24 h. More t-butyl bromoacetate (0.9 g; 4.75 mmol) was added and the mixture stirred at 45° C. for other 12 h. The mixture was filtered and the solution was evaporated. The residue was dissolved in dichloromethane (100 mL) and the solution washed with water (100 mL) then brine (3×100 mL). The organic phase was evaporated and the residue purified by flash chromatography on silica gel (eluent: $CH_2Cl_2/MeOH=100:1\rightarrow4:1$)) to give compound 6 (5.42 g). Yield 89%.

1H-NMR, 13C-NMR and mass spectrum were consistent with the expected structure.

d) Preparation of Ligand 7

Trifluoroacetic acid (2 mL; 26 mmol) was added to a solution of compound 6 (3.8 g, 4.9 mmol) in dichloromethane (20 mL). The mixture was stirred for 30 min then evaporated. The residue was dissolved in TFA (26 mL) and triisopropylsilane (0.1 mL) was added. The obtained mixture was maintained under stirring for 24 h then evaporated. The residue was purified by chromatography on Amberchrome CG161M column (eluent: gradient of water/acetonitrile) obtaining the desired ligand 7 (2.3 g). Yield 85%.

1H-NMR, 13C-NMR and mass spectrum were consistent with the expected structure.

e) Complexation

Ligand 7 (2.03 g; 3.7 mmol) was dissolved in water (15 mL) and 2 M NaOH (7 mL) was added until pH 10. The solution was stirred at 45° C. for 4 h keeping the pH at 10 by addition of 2 M NaOH. The solution was cooled to room temperature, 2M HCl was added until pH 8 and gadolinium chloride hexahydrate (1.37 g; 3.7 mmol) was added. The suspension was stirred at 50° C. for 6 h. The solution was then filtered on Millipore HA 0.25 μm filters and evaporated under reduced pressure. The crude product was purified on Amberchrome CG161M column (eluent: gradient of water/acetonitrile). The fractions containing the pure product were pooled and evaporated. The solid product was dried under vacuum to obtain the gadolinium complex as a white powder (1.56 g). Yield 58%.

Example 16

Preparation of the Chelate Complex 14

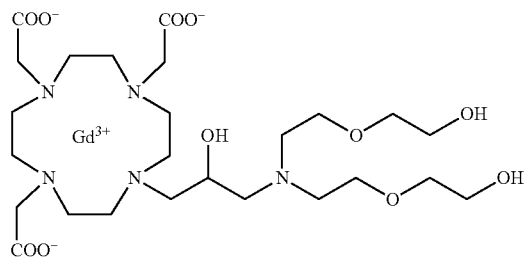

This compound was prepared using the procedure of the following general Scheme 20

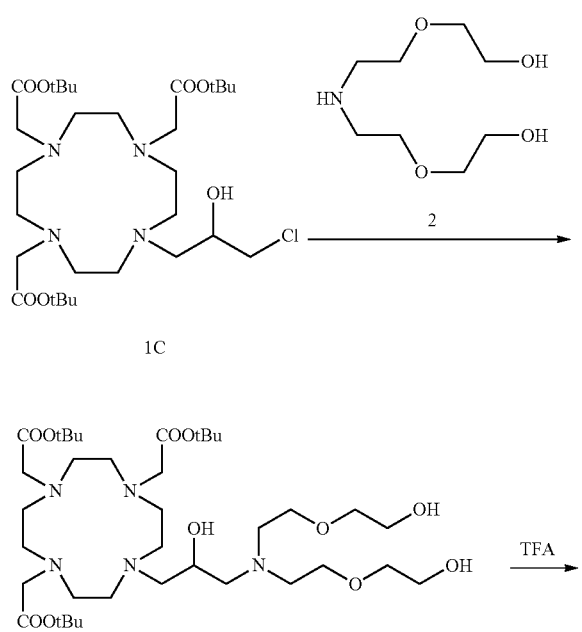

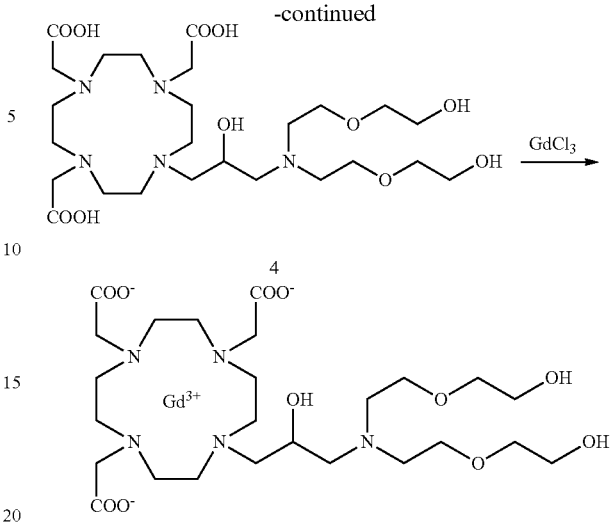

including:

a) Preparation of 3

Substrate 1C (25.2 g) prepared as reported in Example 2 was dissolved in DMSO (10 mL) and 3,9-dioxa-6-azaundecane-1,11-diol 2 (prepared as reported in *J. Org. Chem.* 1995, 60, 6097-6102) (20 g; 100 mmol) was added. The mixture was heated at 80° C. for 8 h then the solvent was evaporated and the residue was purified by flash chromatography on silica gel (eluent: $CH_2Cl_2$/MeOH=98:2) to give compound 3 as pale yellow oil (14 g). Yield 45%.

1H-NMR, 13C-NMR and mass spectrum were consistent with the expected structure.

b) Preparation of the Ligand 4

Trifluoroacetic acid (40 mL; 235 mmol) was added dropwise to a solution of compound 3 (13.5 g, 18 mmol) in dichloromethane (15 mL). The solution was stirred at room temperature overnight. The solvent was evaporated and the residue dissolved in MeOH (5 mL) then diethyl ether (50 mL) was added. The solid precipitated was isolated by centrifugation, the mother liquor removed and the precipitate washed thoroughly with diethyl ether (35 mL). The sticky light brown solid obtained was purified by elution on an ion exchange resin column (Amberlite IR 120, H-form). The free ligand was retained onto the resin and the impurities washed out with water. The product was eluted adding an aqueous solution of $NH_4OH$ (2N) and the acidic fraction was collected and evaporated. The amorphous solid obtained was dissolved in water (2 mL) and precipitated by addition of acetone (40 mL). Ligand 6 was obtained as a sticky white solid (3.1 g). Yield 29%.

1H-NMR, 13C-NMR and mass spectrum were consistent with the expected structure.

c) Complexation

The chelating Ligand 4 (2.3 g; 3.8 mmol) was suspended in water (50 mL) and gadolinium chloride hexahydrate (1.4 g; 3.8 mmol) was added. The suspension was stirred at 60° C. for 6 h. The solution was then filtered on Millipore HA 0.25 μm filters and evaporated under reduced pressure. The crude product was purified on resin Amberlite XAD 1600 (eluent: water). The fractions containing the pure product were pooled and evaporated. The solid product was dried under vacuum to obtain the gadolinium complex as a white powder (1.1 g). Yield 38%.

Mass spectrum and elemental analysis were consistent with the expected structure.

Using the same procedure and 3,6,12,15-tetraoxa-9-azaheptadecane-1,17-diol (prepared as reported in *Tetrahedron* 1982, 38, 3359-3362) Chelate Complex 20 was synthesized.

Example 17

Preparation of the Chelate Complex 21

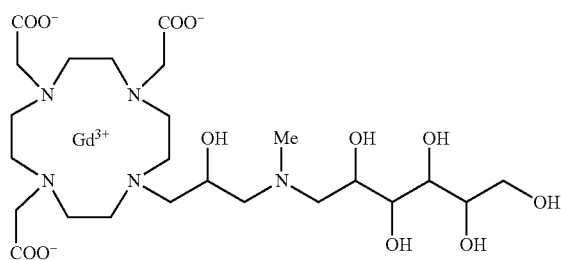

This compound was prepared using the procedure of the following general Scheme 21:

Scheme 21

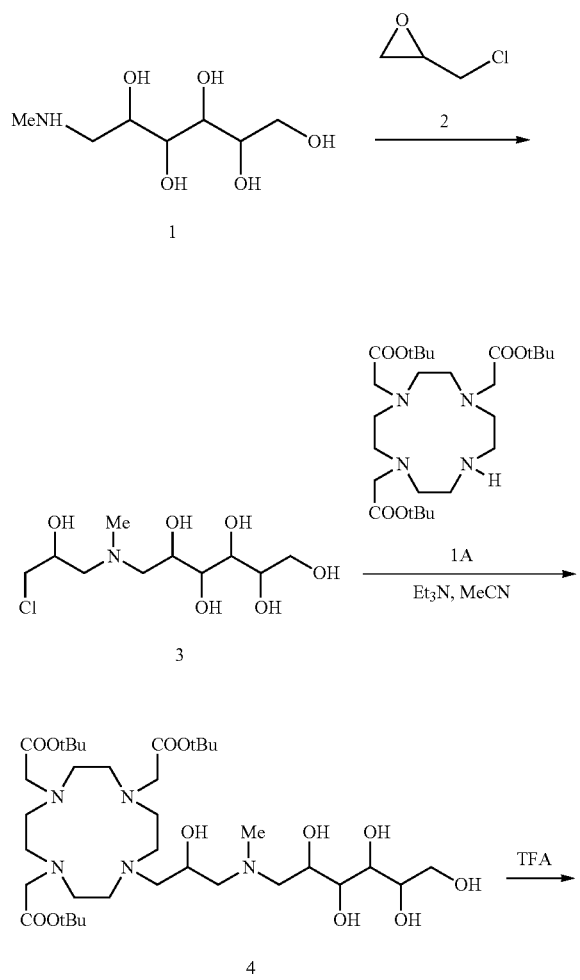

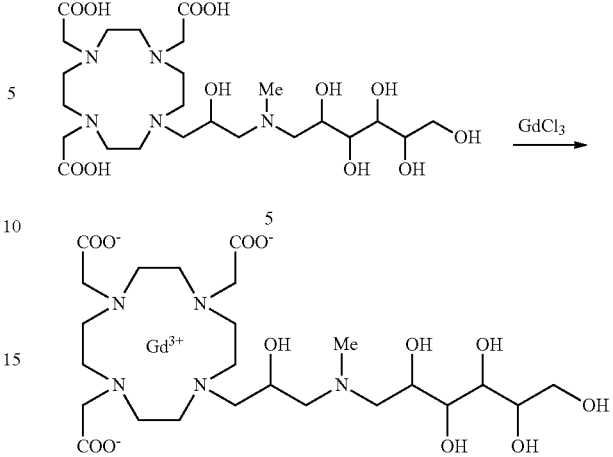

including:

a) Preparation of the Alkylating Molecule 3

Epichlorohydrin 2 (2.96 g; 32 mmol) was added to a suspension of N-methyl-D-glucamine 1 (2.5 g; 12.8 mmol) in methanol (150 mL). The mixture was stirred at room temperature for 72 h then evaporated under vacuum to give the alkylating molecule 3 (3.7 g) as colourless oil. Quantitative yield.

1H-NMR, 13C-NMR and mass spectrum were consistent with the expected structure.

b) Preparation of Intermediate 4

A solution of the alkylating molecule 3 (3.59 g; 12.5 mmol) in DMSO (20 mL) was added to a solution of substrate 1A (2.83 g; 5.5 mmol), and Et$_3$N (3 mL) in acetonitrile (10 mL). The mixture was stirred at 65° C. for 72 h then was evaporated to a residue which was dissolved in water (20 mL). The solution was purified by chromatography on Amberlite XE750 column (eluent: gradient of water/MeCN) to give intermediate 4 (3.8 g). Yield 90%.

1H-NMR, 13C-NMR and mass spectrum were consistent with the expected structure.

c) Preparation of the Ligand 5

A solution of intermediate 4 (4 g; 5.2 mmol) in trifluoroacetic acid (40 mL) was stirred at room temperature for 24 h. Diethyl ether (100 mL) was added and the suspension was stirred for 2 h then filtered. The solid was dissolved in water (20 mL) and the solution was purified by chromatography on Amberlite XE750 column (eluent: gradient of water/acetone) to give ligand 5 (2.7 g). Yield 87%.

1H-NMR, 13C-NMR and mass spectrum were consistent with the expected structure.

d) Complexation

Gadolinium chloride hexahydrate (2.3 g, 6.2 mmol) was added to a solution of chelating ligand 5 (3.7 g; 6.2 mmol) in water (50 mL) and the pH of mixture was slowly increased to pH 7 with 1 N NaOH. The obtained solution was stirred at room temperature for 4 h then filtered on Millipore HA 0.45 μm, concentrated and purified by chromatography on Amberlite XE750 column (eluent: gradient of water/acetonitrile) obtaining 4 g of the gadolinium complex. Yield 86%.

Mass spectrum and elemental analysis were consistent with the expected structure.

Example 18

Preparation of the Chelate Complex 11

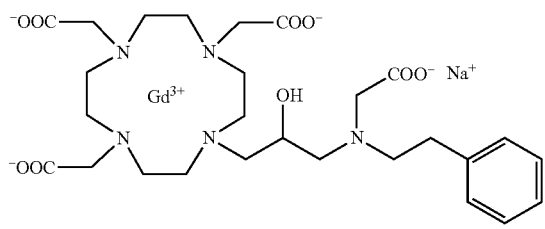

This compound was prepared using the procedure of the following general Scheme 22:

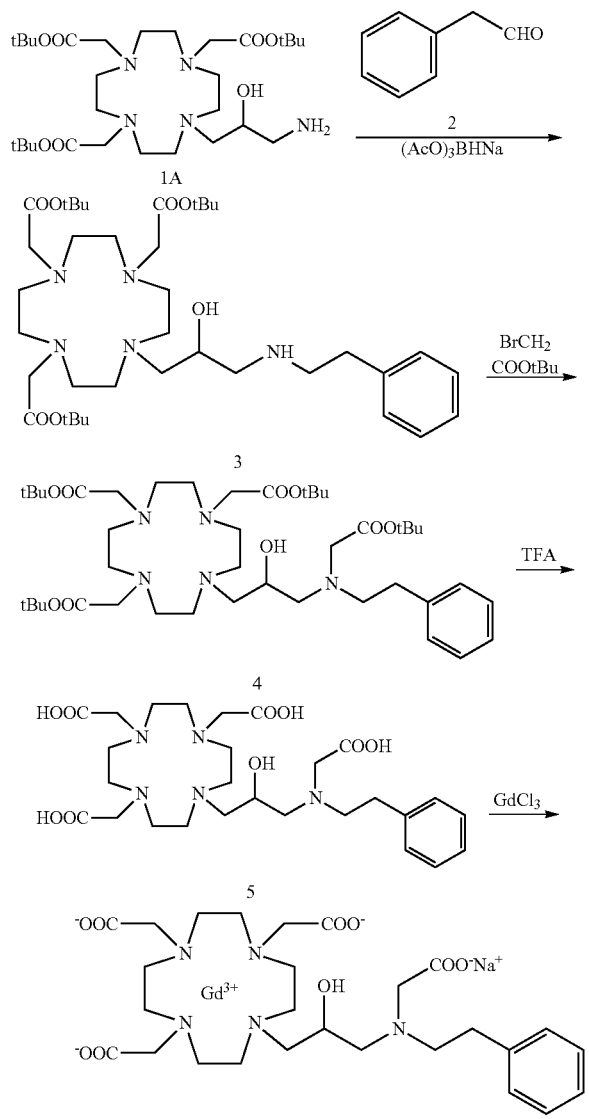

including as main steps:

a) Preparation of Intermediate 3

Phenylacetaldehyde (11.6 g; 0.097 mol) and acetic acid (12 mL) were added to a solution of Substrate 1A (70 g; 0.102 mol) in THF (600 mL) and the reaction mixture was stirred for 2 h. The solution was then cooled to 0° C. and sodium triacetoxyborohydride (32.4 g; 0.153 mol) was added in small portions. The reaction was maintained at room temperature for 16 h then water (150 mL) was added. The organic solvent was evaporated and the pH of the remaining aqueous solution was increased to pH 11 with 2N NaOH then extracted with dichloromethane (5×200 mL). After evaporation of the organic solvent the monoalkylated intermediate 3 was obtained as a residue (54 g). Yield 80%.

1H-NMR, 13C-NMR and mass spectrum were consistent with the expected structure.

b) Preparation of Intermediate 4

A mixture of compound 3 (54 g; 0.078 mol), t-butyl bromoacetate (19.8 g; 0.101 mol) and $K_2CO_3$ (21.6 g; 0.156 mol) in acetonitrile (350 mL) was stirred at room temperature for 48 h. The mixture was filtered and the solution was evaporated to give an oil that was dissolved with EtOAc (400 mL). The solution was washed with water (3×150 mL), brine (100 mL) and evaporated. The crude oily residue was purified by flash chromatography on silica gel (eluent: $CH_2Cl_2$/MeOH=100:1→4:1). The fractions containing the product were pooled and evaporated to give intermediate 4 (42.9 g) Yield 68%.

1H-NMR, 13C-NMR and mass spectrum were consistent with the expected structure.

c) Preparation of the Ligand 5

Trifluoroacetic acid (10 mL) was slowly added to a solution of intermediate 4 (42.5 g; 0.049 mol) in $CH_2Cl_2$ (300 mL) and the mixture was stirred at room temperature for 1 h. The solvent was evaporated and the residue was dissolved in trifluoroacetic acid (200 mL) and triisopropylsilane (2 mL) was added. The obtained mixture was maintained under stirring for 48 h then evaporated. Diethyl ether (500 mL) was added and the suspension was stirred for 2 h then filtered. The solid was dissolved in water (20 mL) and the solution was purified by chromatography on Amberlite XE750 column (eluent: gradient of water/acetonitrile) to give ligand 5 (16.1 g). Yield 56%.

1H-NMR, 13C-NMR and mass spectrum were consistent with the expected structure.

d) Complexation

Gadolinium chloride hexahydrate (8.25 g, 0.222 mol) was added to a solution of chelating ligand 5 (12.9 g; 0.222 mol) in water (400 mL) and the pH of mixture was slowly increased to pH 7 with 2 N NaOH. The obtained solution was stirred at room temperature for 8 h then filtered on Millipore HA 0.45 μm, concentrated and purified by chromatography on Amberlite XE750 column (eluent: gradient of water/acetonitrile) obtaining 16 g of the gadolinium complex. Yield 95%.

Mass spectrum and elemental analysis were consistent with the expected structure.

Example 19

Preparation of the Chelate Complex 6

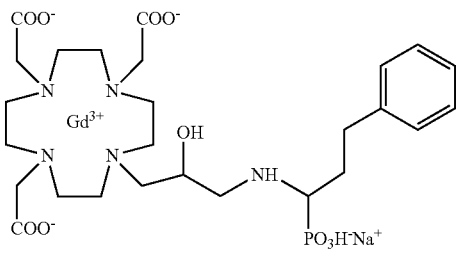

This compound was prepared using the procedure of the following general Scheme 23:

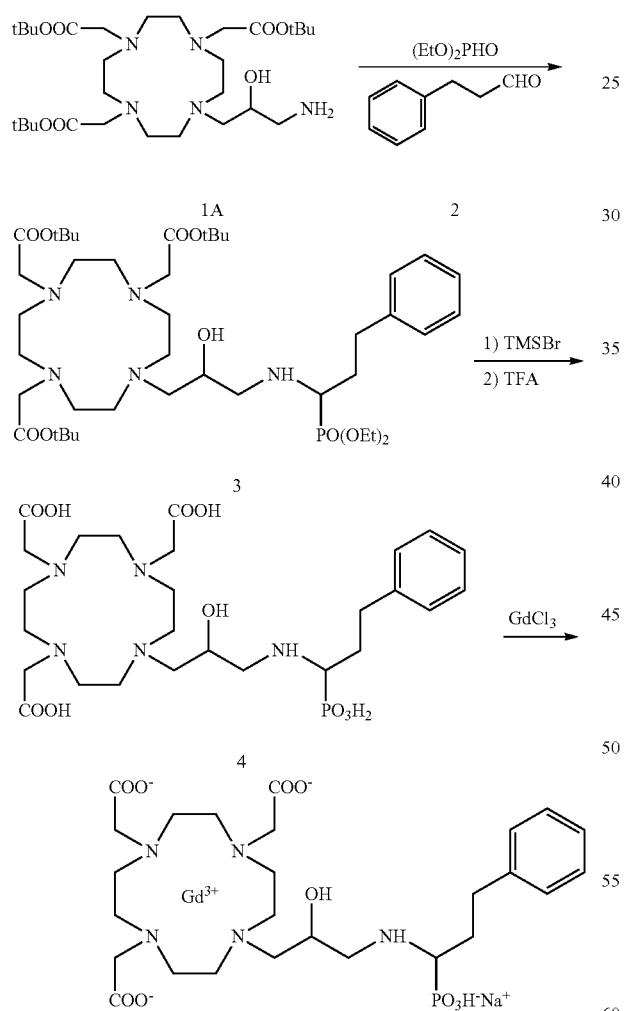

including as main steps:

a) Preparation of Intermediate 3

A mixture of substrate 1A (15 g; 0.025 mol), 3-phenyl-propionaldehyde 2 (3.3 mL; 0.026 mol) and diethylphosphite (3.9 mL; 0.030 mol) was heated at 80° C. for 8 h. The crude reaction mixture was purified by flash chromatography on silica gel (eluent: $CH_2Cl_2$/2-propanol=95/5). The fractions containing the product were collected and evaporated to give intermediate 3 as a colorless oil (17 g) Yield 80%.

1H-NMR, 13C-NMR and mass spectrum were consistent with the expected structure.

b) Preparation of Intermediate 4

A solution of bromotrimethylsilane (25.9 mL; 196 mmol) in $CH_2Cl_2$ (50 mL) was slowly added to a solution of compound 3 (16.5 g; 19.6 mmol) in $CH_2Cl_2$ (100 mL). The mixture was stirred at room temperature for 16 h then the solvent was evaporated. The residue was treated with trifluoroacetic acid (50 mL) and the mixture stirred for 12 h. The solvent was evaporated and the residue was purified by chromatography on Amberlite XAD 1600 column (eluent: gradient of water/MeOH) to give ligand 4 (5.5 g). Yield 45%.

1H-NMR, 13C-NMR and mass spectrum were consistent with the expected structure.

c) Complexation

Gadolinium chloride hexahydrate (1.93 g, 5.2 mmol) was added to a solution of chelating ligand 4 (5.2 g; 5.2 mmol) in water (40 mL) and the pH of mixture was slowly increased to pH 7 with 2 N NaOH. The obtained solution was stirred at 80° C. for 24 h then filtered on Millipore HA 0.45 µm, concentrated and purified by chromatography on Amberlite XE750 column (eluent: gradient of water/acetonitrile) obtaining 2.3 g of the gadolinium complex. Yield 54%.

Mass spectrum and elemental analysis were consistent with the expected structure.

Example 20

Preparation of the Chelate Complex 16

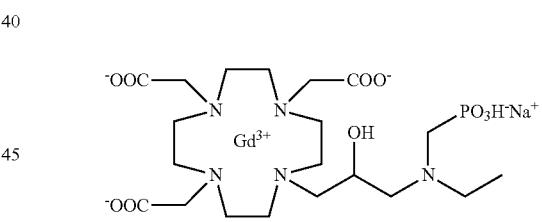

This compound was prepared using the procedure of the following general Scheme 24:

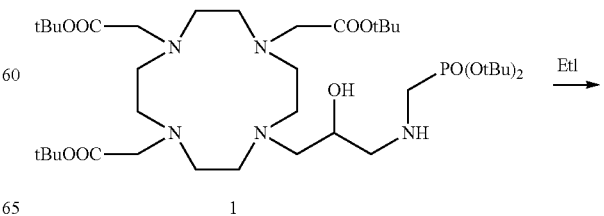

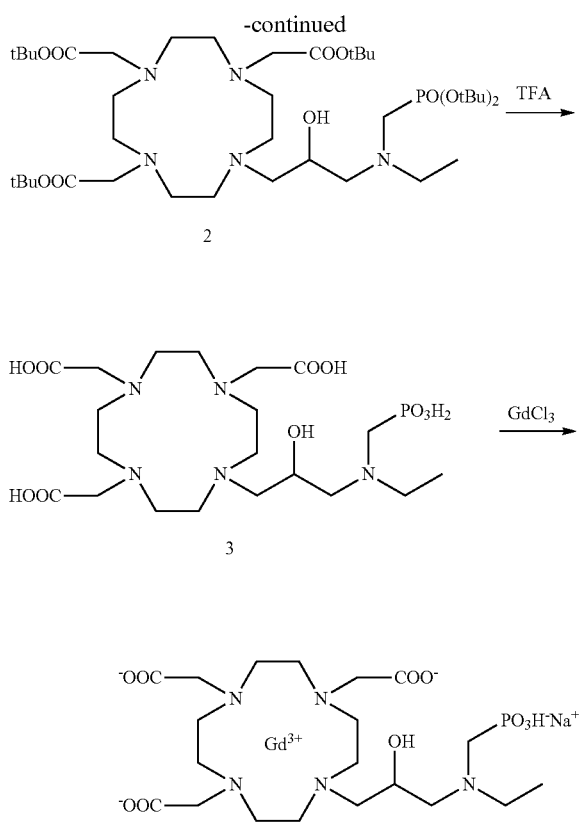

including as main steps:

a) Preparation of Intermediate 2

A mixture of compound 1 (prepared as reported in Example 12) (25 g; 31.5 mmol) and iodoethane (5.5 g; 35 mmol) in DMF (200 mL) was heated at 50° C. and stirred for 24 h. The solvent was evaporated and the residue was purified by flash chromatography on silica gel (eluent: $CH_2Cl_2$/MeOH=100:1→4:1).). The fractions containing the product were collected and evaporated to give intermediate 2 (17.3 g) Yield 67%.

1H-NMR, 13C-NMR and mass spectrum are consistent with the expected structure.

b) Preparation of the Ligand 3

Trifluoroacetic acid (10 mL) was slowly added to a solution of intermediate 2 (15 g; 18 mmol) in $CH_2Cl_2$ (100 mL) and the mixture was stirred at room temperature for 1 h. The solvent was evaporated and the residue was dissolved in trifluoroacetic acid (50 mL) and triisopropylsilane (0.1 mL) was added. The obtained mixture was maintained under stirring for 24 h then evaporated. The residue was purified by chromatography on Amberlite XE750 column (eluent: gradient of water/acetonitrile) to give ligand 3 (6.1 g). Yield 62%.

1H-NMR, 13C-NMR and mass spectrum were consistent with the expected structure.

c) Complexation

Gadolinium chloride hexahydrate (3.7 g, 10 mmol) was added to a solution of chelating ligand 3 (5.4 g; 10 mmol) in water (50 mL) and the pH of mixture was slowly increased to pH 7 with 2 N NaOH. The solution was stirred at 80° C. for 24 h then filtered on Millipore HA 0.45 μm, concentrated and purified by chromatography on Amberlite XE750 column (eluent: gradient of water/acetonitrile) obtaining 5.7 g of the gadolinium complex. Yield 79%.

Mass spectrum and elemental analysis were consistent with the expected structure.

Example 21

Relaxometric Properties

The relaxometric properties of some representative complex compounds according to the invention have been determined at different magnetic field strengths, e.g. including 0.47 and 1.41 T, at 37° C. and in different media (physiologic solution and human plasma) and compared with relaxivity values measured, at the same conditions, for some Gd-Complex of the market having an analogous cyclic coordination cage.

Materials

Apparatus

The longitudinal water proton relaxation rate ($R_1=1/T_1$) was measured at 0.47 T with a Minispec MQ-20 spectrometer (Bruker Biospin, Germany) operating at a proton Larmor frequency of 20 MHz; MR experiments at 1.41 T were performed using a Minispec MQ-60 spectrometer (Bruker Biospin, Germany) operating at a proton Larmor frequency of 60 MHz.

Methods

Sample Preparation

All test articles were used as supplied and diluted in the selected medium (physiologic solution or human plasma) by weighting the required amount of paramagnetic chelated complex to get a 5 or 10 mM starting solution.

Relaxivity Measurements

Five different concentration samples (0.1, 0.25, 0.5, 0.75 and 1 mM) for each medium have been prepared by further dilution of the starting 5 or 10 mM solution.

Relaxation Measurement

Relaxivity measurements were performed at 0.47 T and 1.41 T at a preset temperature sample of 37° C., kept constant by means of a thermostatic bath connected to the sample holder of the spectrometer. The five sample solutions have been preliminary pre-heated at 37° C. in an external thermostatic bath and then left 10 minutes inside the internal bath to assure the stabilization of the temperature. Longitudinal relaxation time $T_1$ was measured by means of a standard inversion recovery sequence, where the inversion time (TI) was varied from 10 ms to at least 5 times $T_1$ in 15 steps. Statistical analysis (mono-exponential fitting for $T_1$ measurement, linear fitting for the evaluation of longitudinal relaxivity) was performed by Mathematica® (Wolfram, USA). Errors on the estimated parameters were evaluated by the fitting procedure.

Results

The relaxivity values $r_{1p}$ obtained from some representative compounds according to the invention, both in physiologic solution and in human plasma, at 37° C., are summarized in the following Table A, together with the structure of tested compounds and the strength of the applied magnetic field (in T), and compared with corresponding values measured for some commercial contrast agents in clinical practice.

TABLE A
| | $r_{1p}$ [mM$^{-1}$s$^{-1}$] | | | |
|---|---|---|---|---|
| Complex | $r_{1p}$ at 0.47 T 37° C., saline | $r_{1p}$ at 0.47 T 37° C., human plasma | $r_{1p}$ at 1.41 T 37° C., saline | $r_{1p}$ at 1.41 T 37° C., human plasma |
| 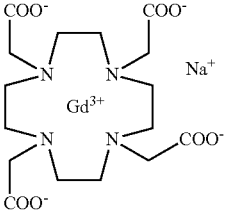 Dotarem ® | 3.6 | 4.5 | 3.2 | 3.6 |
| 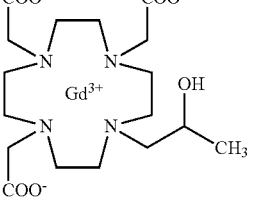 ProHance ® | 3.5 | 4.9 | 3.1 | 4.15 |
| 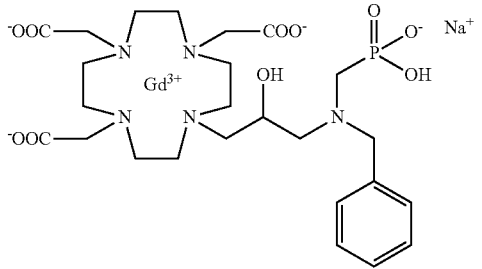 Comparative 1 | 4.3 | 6.25 | 3.8 | 5.3 |
| 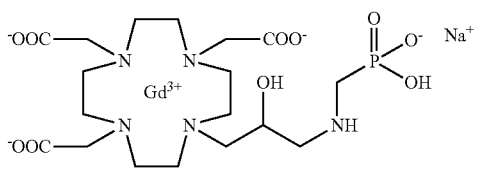 Chelate Complex 1 | 7.1 | 10.9 | 6.7 | 9.5 |
| Chelate Complex | 7.0 | 8.5 | 6.5 | 7.5 |

TABLE A-continued
| Complex | $r_{1p}$ at 0.47 T 37° C., saline | $r_{1p}$ at 0.47 T 37° C., human plasma | $r_{1p}$ at 1.41 T 37° C., saline | $r_{1p}$ at 1.41 T 37° C., human plasma |
|---|---|---|---|---|
| Chelate Complex 2 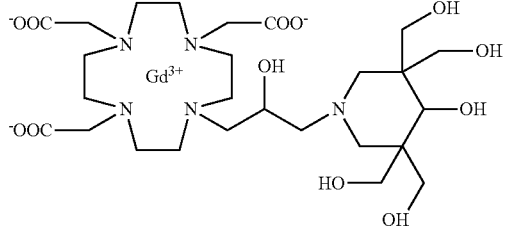 | 7.7 | 9.6 | 7.7 | 8.9 |
| Chelate Complex 5 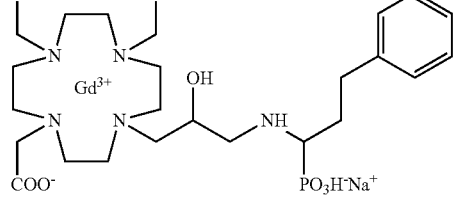 | 8.3 | 13.8 | 8.2 | 11.9 |
| Chelate Complex 6 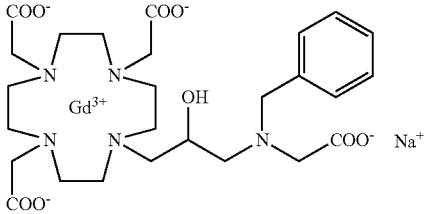 | 6.4 | 9.4 | 6.0 | 8.1 |
| Chelate Complex 7 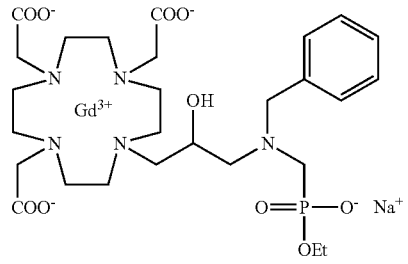 | 7.4 | 10.2 | 7.3 | 9.0 |
| Chelate Complex 8 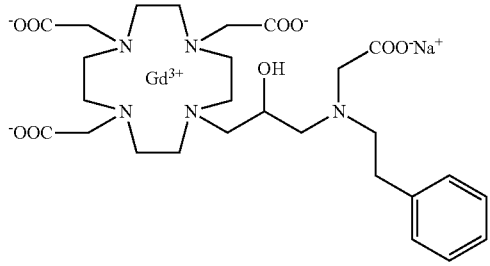 | 6.6 | 10.1 | 6.5 | 9.0 |

TABLE A-continued

| Complex | $r_{1p}$ [mM$^{-1}$s$^{-1}$] | | | |
|---|---|---|---|---|
| | $r_{1p}$ at 0.47 T 37° C., saline | $r_{1p}$ at 0.47 T 37° C., human plasma | $r_{1p}$ at 1.41 T 37° C., saline | $r_{1p}$ at 1.41 T 37° C., human plasma |
| Chelate Complex 11 | 5.8 | 7.5 | 5.9 | 7.1 |
| Chelate Complex 13 | 5.8 | 6.9 | 5.5 | 6.4 |
| Chelate Complex 4 | 6.9 | 8.8 | 6.5 | 8.0 |
| Chelate Complex 14 | 6.7 | 8.7 | 6.4 | 7.75 |
| Chelate Complex 15 | 6.5 | 7.8 | 6.4 | 7.1 |
| Chelate Complex 16 | 6.5 | 9.1 | 6.1 | 8.05 |

TABLE A-continued

| | $r_{1p}$ [mM$^{-1}$s$^{-1}$] | | | |
|---|---|---|---|---|
| Complex | $r_{1p}$ at 0.47 T 37° C., saline | $r_{1p}$ at 0.47 T 37° C., human plasma | $r_{1p}$ at 1.41 T 37° C., saline | $r_{1p}$ at 1.41 T 37° C., human plasma |
| Chelate Complex 19 | | | | |
| Chelate Complex 21 | 6.1 | 8.5 | 6.1 | 8.3 |

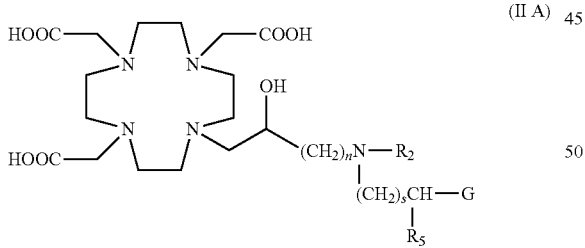

CONCLUSIONS

The relaxivity of the investigated contrast agents ranges between 4.3 (for the unsubstituted Comparative 1) and 8.3 (for the Chelate Complex 6) mM$^{-1}$s$^{-1}$ at 0.47 T in physiological solution, and from 6.25 to 13.8 mM$^{-1}$s$^{-1}$ in plasma, same magnetic field. Such values decrease, as expected, increasing the magnetic field strength. These results confirm that the particular selection represented by the paramagnetic complexes and, especially, the Gd$^{3+}$ complexes of the compounds of formula (I) of the invention show an increased relaxivity $r_{1p}$, which is at least about 1.5 up to 2 times the relaxivity shown, at the same conditions (i.e. in saline or in human plasma, at 37° C.), by the Non Specific contrast agents currently in use in the daily diagnostic practice, such as Dotarem® and ProHance®.

The invention claimed is:
1. A compound of formula (II A)

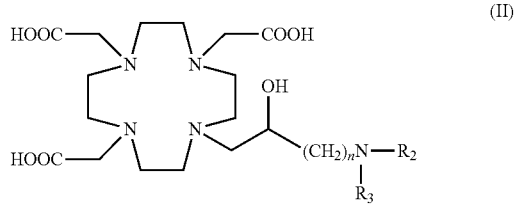

in which:
n is 1;
s is 0, 1 or 2;
G is a group of formula —PO(OR$_6$)$_2$ or —COOH, in which R$_6$ independently of one another is is H or C$_1$-C$_5$ alkyl;
R$_5$ is H, or an arylalkylene or cycloalkyl-alkylene having up to 3 carbon atoms in the alkylene chain; and
R$_2$ is a phenyl or a cyclohexyl ring, or a C$_1$-C$_7$ alkyl which is optionally substituted by one or more hydroxyl groups or by an optionally substituted phenyl or cyclohexyl ring or a physiologically acceptable salt thereof.

2. A compound of formula (II)

in which:
n is 1 or 2;
R$_2$ is selected from the group consisting of: an aryl ring, a cycloalkyl ring, and a C$_1$-C$_{10}$ alkyl optionally interrupted by one or more oxygen atoms and/or optionally substituted by one or more hydroxyl groups, or by an aryl or cycloalkyl ring; and
R$_3$ is a C$_2$-C$_{10}$ hydroxyalkoxyalkylene of formula —(CH$_2$)$_r$—[(O—(CH$_2$)$_r$]$_m$(CH$_2$)$_s$OH; where
s is 0, 1 or 2;
r is, independently of one another, 1 or 2; and
m is 1, 2 or 3
or a physiologically acceptable salt thereof.

3. The compound of claim 2 of formula (II B)

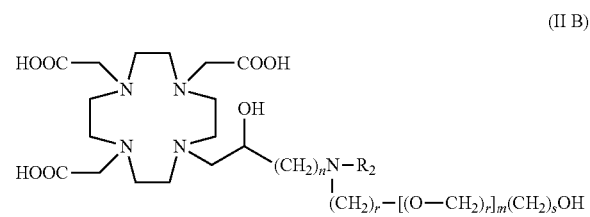

in which:
n is 1;
each r is independently 1 or 2
m is 1, 2 or 3;
s is 0, 1 or 2; and
R$_2$ is a second hydroxyalkoxyalkylene chain of formula —(CH$_2$)$_r$-[(O—(CH$_2$)$_r$]$_m$(CH$_2$)$_s$OH.

4. The compound of claim 3 in which in the formula (II B) the hydroxyalkoxyalkylene chains are each independently selected from groups of formula —$CH_2(OCH_2CH_2)_s$ $OCH_2OH$, —$(CH_2)_r$—$O(CH_2)_rOH$ and —$CH_2(CH_2OCH_2)_r$ $CH_2OH$.

5. The compound of claim 2 of formula (II C)

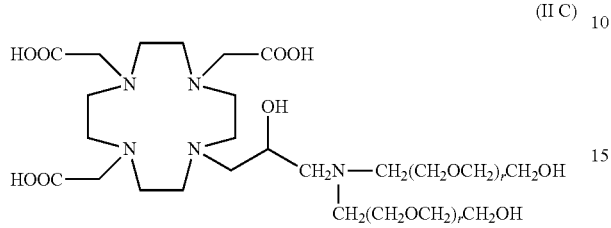

(II C)

in which r is 1 or 2.

6. A compound of formula (III A)

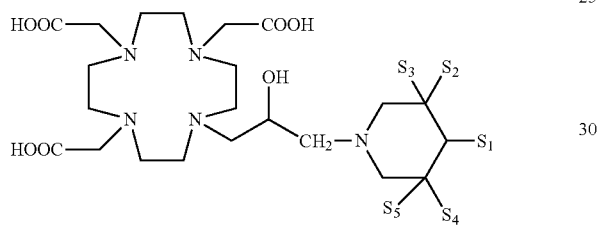

(III A)

in which the substituent groups $S_1$-$S_5$ are selected from the group consisting of:

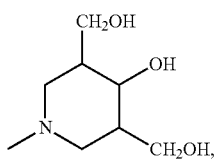

1

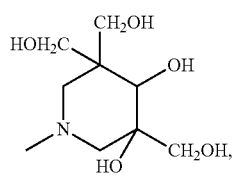

2

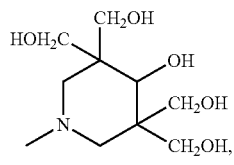

3

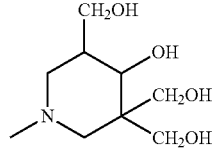

4

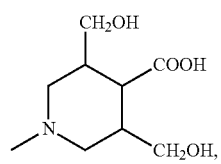

5

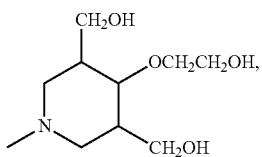

6

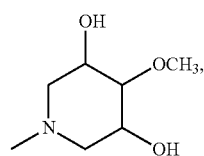

7

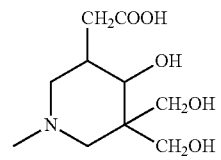

8

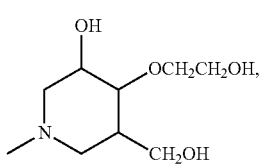

9

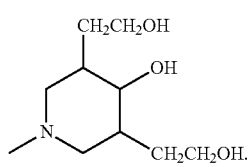

10

7. A compound of formula (III A)

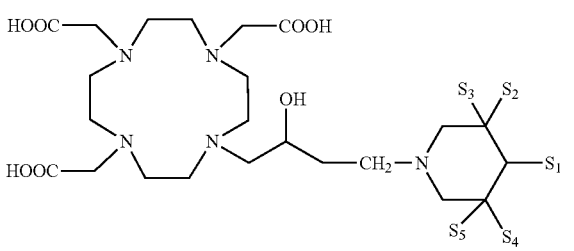

(IIIA)

in which $S_1$ is a hydroxyl group, $S_2$-$S_4$ are equal or different $C_1$-$C_3$ hydroxyalkyls, and $S_5$ is selected from the group consisting of: H, hydroxyl, carboxyl, $C_1$-$C_3$ hydroxyalkyl, $C_1$-$C_3$ hydroxyalkoxy and $C_1$-$C_3$ hydroxyalkoxy-alkylene, or a physiologically acceptable salt thereof.

8. A compound of formula (IV)

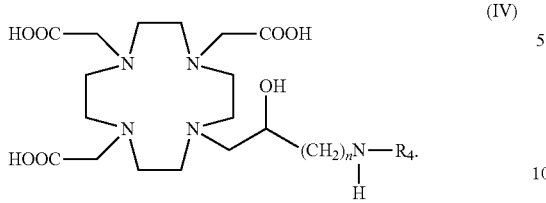

in which n is 1, and $R_4$ is selected from the group consisting of formula $-(CH_2)_mPO(OR_6)_2$, $-(CH_2)_mPO(R_7)(OR_6)$ and $-(CH_2)_sCH(R_8)G$; where:

m is 1, 2 or 3;
s is 0, 1 or 2;
$R_6$ independently of one another is H or $C_1$-$C_5$ alkyl;
$R_7$ is an optionally substituted phenyl or cyclohexyl, or $C_1$-$C_5$ alkyl which is optionally substituted by a phenyl or cyclohexyl ring;
$R_8$ is an optionally substituted arylalkylene or cycloalkyl-alkylene having up to 3 carbon atoms in the alkylene chain; and
G is a group selected from $-PO(OR_6)_2$, $-PO(R_7)(OR_6)$ and $-COOH$, where $R_6$ and $R_7$ are as above said.

9. The compound of claim 8 of formula (IV A)

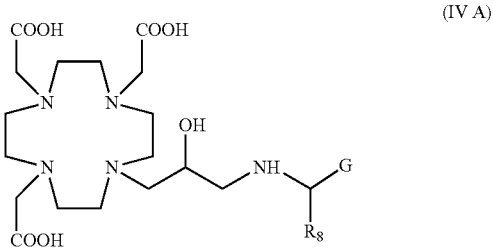

in which:
$R_8$ is selected from the group consisting of benzyl, phenyl-ethylene, cyclohexyl-methylene and cyclohexyl-ethylene; and
G is a group selected from $-PO(OR_6)_2$ and $-COOH$, where $R_6$ is H or tert-butyl.

10. A chelated complex of a compound according to claim 7 with a paramagnetic metal ion selected from the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ and $Mn^{2+}$, or a physiologically acceptable salt thereof.

11. The chelated complex of claim 10, wherein the paramagnetic metal ion is $Gd^{3+}$.

12. A compound according to claim 7, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

13. The chelated complex according to claim 10, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

14. A method of MR imaging comprising:
administering the chelated complex according to claim 10 to a patient;
submitting the patient to a radiation frequency selected to excite non-zero proton spin nuclei of the chelated complex; and
recording a MR signal from said nuclei.

15. A pharmaceutical composition comprising a chelated complex according to claim 10 in combination with one or more pharmaceutically acceptable carriers, diluents or excipients.

16. The compound of claim 6 in which the substituent groups $S_1$-$S_5$ are,

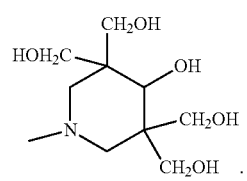

17. A chelated complex of a compound according to claim 1 with a paramagnetic metal ion selected from the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ and $Mn^{2+}$, or a physiologically acceptable salt thereof.

18. The chelated complex of claim 17, wherein the paramagnetic metal ion is $Gd^{3+}$.

19. A compound according to claim 1, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

20. The chelated complex according to claim 17, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

21. A method of MR imaging comprising:
administering the chelated complex according to claim 1 to a patient;
submitting the patient to a radiation frequency selected to excite non-zero proton spin nuclei of the chelated complex; and
recording a MR signal from said nuclei.

22. A pharmaceutical composition comprising a chelated complex according to claim 17 in combination with one or more pharmaceutically acceptable carriers, diluents or excipients.

23. A chelated complex of a compound according to claim 2 with a paramagnetic metal ion selected from the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ and $Mn^{2+}$, or a physiologically acceptable salt thereof.

24. The chelated complex of claim 23, wherein the paramagnetic metal ion is $Gd^{3+}$.

25. A compound according to claim 2, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

26. The chelated complex according to claim 23, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

27. A method of MR imaging comprising:
administering the chelated complex according to claim 2 to a patient;
submitting the patient to a radiation frequency selected to excite non-zero proton spin nuclei of the chelated complex; and
recording a MR signal from said nuclei.

28. A pharmaceutical composition comprising a chelated complex according to claim 23 in combination with one or more pharmaceutically acceptable carriers, diluents or excipients.

29. A chelated complex of a compound according to claim 6 with a paramagnetic metal ion selected from the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ and $Mn^{2+}$, or a physiologically acceptable salt thereof.

30. The chelated complex of claim 29, wherein the paramagnetic metal ion is $Gd^{3+}$.

31. A compound according to claim 6, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

32. The chelated complex according to claim 29, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

33. A method of MR imaging comprising:
administering the chelated complex according to claim 6 to a patient;
submitting the patient to a radiation frequency selected to excite non-zero proton spin nuclei of the chelated complex; and
recording a MR signal from said nuclei.

34. A pharmaceutical composition comprising a chelated complex according to claim 29 in combination with one or more pharmaceutically acceptable carriers, diluents or excipients.

35. A chelated complex of a compound according to claim 8 with a paramagnetic metal ion selected from the group consisting of $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ and $Mn^{2+}$, or a physiologically acceptable salt thereof.

36. The chelated complex of claim 35, wherein the paramagnetic metal ion is $Gd^{3+}$.

37. A compound according to claim 8, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

38. The chelated complex according to claim 35, wherein the physiologically acceptable salt is with a cation of (i) an inorganic base selected from an alkali metal and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

39. A method of MR imaging comprising:
administering the chelated complex according to claim 8 to a patient;
submitting the patient to a radiation frequency selected to excite non-zero proton spin nuclei of the chelated complex; and
recording a MR signal from said nuclei.

40. A pharmaceutical composition comprising a chelated complex according to claim 35 in combination with one or more pharmaceutically acceptable carriers, diluents or excipients.

* * * * *

UNITED STATES PATENT AND TRADEMARK OFFICE
CERTIFICATE OF CORRECTION

PATENT NO. : 10,781,188 B2
APPLICATION NO. : 16/060577
DATED : September 22, 2020
INVENTOR(S) : Lattuada et al.

Page 1 of 1

It is certified that error appears in the above-identified patent and that said Letters Patent is hereby corrected as shown below:

In the Specification

Column 3, Lines 58-59, "from -PO(OR6)2, -PO(R2) (OR6)" should read — from -PO(OR6)2, -PO(R7) (OR6) —.

In the Claims

Column 73, Line 60, Claim 1, "one another is is H" should read — one another is H —.

Signed and Sealed this
Eighth Day of December, 2020

Andrei Iancu
*Director of the United States Patent and Trademark Office*